United States Patent
Coffey

(10) Patent No.: US 11,246,930 B2
(45) Date of Patent: *Feb. 15, 2022

(54) REOVIRUSES HAVING MODIFIED SEQUENCES

(71) Applicant: Oncolytics Biotech Inc., Calgary (CA)

(72) Inventor: Matthew C. Coffey, Calgary (CA)

(73) Assignee: ONCOLYTICS BIOTECH INC., Calgary (CA)

( * ) Notice: Subject to any disclaimer, the term of this patent is extended or adjusted under 35 U.S.C. 154(b) by 2 days.

This patent is subject to a terminal disclaimer.

(21) Appl. No.: 16/790,114

(22) Filed: Feb. 13, 2020

(65) Prior Publication Data

US 2020/0237917 A1      Jul. 30, 2020

Related U.S. Application Data

(60) Continuation of application No. 16/027,206, filed on Jul. 3, 2018, now Pat. No. 10,596,260, which is a continuation of application No. 14/179,840, filed on Feb. 13, 2014, now Pat. No. 10,039,827, which is a continuation of application No. 12/848,684, filed on Aug. 2, 2010, now Pat. No. 8,691,241, which is a division of application No. 12/046,095, filed on Mar. 11, 2008, now Pat. No. 7,803,385.

(60) Provisional application No. 60/989,568, filed on Nov. 21, 2007, provisional application No. 60/894,425, filed on Mar. 12, 2007.

(51) Int. Cl.
| A61K 35/765 | (2015.01) |
| C12N 7/00 | (2006.01) |
| A61K 45/06 | (2006.01) |
| C07K 14/005 | (2006.01) |
| A61K 35/13 | (2015.01) |

(52) U.S. Cl.
CPC ............ *A61K 45/06* (2013.01); *A61K 35/765* (2013.01); *C07K 14/005* (2013.01); *C12N 7/00* (2013.01); *A61K 35/13* (2013.01); *C12N 2720/12221* (2013.01); *C12N 2720/12222* (2013.01); *C12N 2720/12232* (2013.01)

(58) Field of Classification Search
CPC ........ A61K 35/765; A61P 35/00; A61P 43/00; C12N 2720/12032; C12N 2720/12232
See application file for complete search history.

(56) References Cited

U.S. PATENT DOCUMENTS

| 6,110,461 | A | 8/2000 | Lee et al. |
| 6,136,307 | A | 10/2000 | Lee et al. |
| 6,261,555 | B1 | 7/2001 | Lee et al. |
| 6,344,195 | B1 | 2/2002 | Lee et al. |
| 6,528,305 | B2 | 3/2003 | Thompson et al. |
| 6,565,831 | B1 | 5/2003 | Coffey et al. |
| 6,576,234 | B2 | 6/2003 | Lee et al. |
| 6,808,916 | B2 | 10/2004 | Coffey et al. |
| 6,811,775 | B2 | 11/2004 | Lee et al. |
| 7,014,847 | B2 | 3/2006 | Coffey et al. |
| 7,049,127 | B2 | 5/2006 | Thompson et al. |
| 7,052,832 | B2 | 5/2006 | Coffey |
| 7,163,678 | B2 | 1/2007 | Norman et al. |
| 7,186,542 | B2 | 3/2007 | Coffey et al. |
| 7,374,752 | B2 | 5/2008 | Lee et al. |
| 7,452,723 | B2 | 11/2008 | Coffey et al. |
| 7,803,385 | B2 * | 9/2010 | Coffey .................. A61K 45/06 424/215.1 |
| 8,470,312 | B2 | 6/2013 | Coffey et al. |
| 8,691,241 | B2 * | 4/2014 | Coffey ................ C07K 14/005 424/215.1 |
| 9,044,498 | B2 | 6/2015 | Coffey et al. |
| 9,045,728 | B2 | 6/2015 | Coffey et al. |
| 9,610,309 | B2 | 4/2017 | Coffey et al. |
| 9,610,352 | B2 | 4/2017 | Coffey et al. |
| 10,039,827 | B2 * | 8/2018 | Coffey ................ A61K 35/765 |
| 10,596,260 | B2 * | 3/2020 | Coffey ................ C07K 14/005 |
| 2006/0165724 | A1 | 7/2006 | Thompson et al. |
| 2008/0014183 | A1 | 1/2008 | Okano et al. |
| 2009/0035278 | A2 | 2/2009 | Coffey |
| 2009/0214479 | A1 | 8/2009 | Kim et al. |

FOREIGN PATENT DOCUMENTS

| JP | 2004519431 | 7/2004 |
| WO | 0243647 | 6/2002 |
| WO | 2005111200 | 11/2005 |
| WO | 2007099401 | 9/2007 |
| WO | 2008009115 | 1/2008 |

OTHER PUBLICATIONS

GenBank Accession No. AF129822, Jul. 5, 1999, 1 page.
GenBank Accession No. AF461684, Apr. 12, 2002, 1 page.
GenBank Accession No. J03488, Aug. 3, 1993, 1 page.
GenBank Accession No. M10262, Aug. 3, 1993, 1 page.
GenBank Accession No. M20161, Mar. 7, 1995, 1 page.
GenBank Accession No. M24734, Jun. 16, 1994, 1 page.
GenBank Accession No. NP 694684, May 22, 2008, 1 page.
GenBank Accession No. X01627, Mar. 25, 2003, 1 page.
RNA-Directed RNA Polymerase Lambda-3, Database UniProt, Accession No. P:17376, XP002657657, Aug. 1, 1990, 4 pages.
U.S. Appl. No. 12/046,095, Non-Final Office Action dated Jan. 6, 2010, 21 pages.
U.S. Appl. No. 12/046,095, Non-Final Office Action dated Aug. 24, 2009, 7 pages.
U.S. Appl. No. 12/046,095, Notice of Allowance dated Jun. 8, 2010, 7 pages.
U.S. Appl. No. 12/848,684, Final Office Action dated Oct. 23, 2012, 9 pages.

(Continued)

*Primary Examiner* — Bao Q Li
(74) *Attorney, Agent, or Firm* — Kilpatrick Townsend & Stockton LLP

(57) ABSTRACT

The invention provides for modified reovirus nucleic acid sequences and modified reovirus polypeptide sequences as well as reoviruses containing such modified nucleic acid or polypeptide sequences. The invention also provides for pharmaceutical compositions that include reoviruses having a modified sequence as well as methods of making and using such reoviruses.

14 Claims, 12 Drawing Sheets

Specification includes a Sequence Listing.

(56) References Cited

OTHER PUBLICATIONS

U.S. Appl. No. 12/848,684, Non-Final Office Action dated Jun. 20, 2013, 12 pages.
U.S. Appl. No. 12/848,684, Non-Final Office Action dated Jul. 19, 2012, 13 pages.
U.S. Appl. No. 12/848,684, Notice of Allowance dated Nov. 21, 2013, 11 pages.
U.S. Appl. No. 14/179,840, Advisory Action dated Sep. 15, 2016, 3 pages.
U.S. Appl. No. 14/179,840, Final Office Action dated Jul. 1, 2016, 11 pages.
U.S. Appl. No. 14/179,840, Final Office Action dated Dec. 19, 2016, 9 pages.
U.S. Appl. No. 14/179,840, Non-Final Office Action dated Apr. 21, 2017, 10 pages.
U.S. Appl. No. 14/179,840, Non-Final Office Action dated Sep. 19, 2017, 10 pages.
U.S. Appl. No. 14/179,840, Non-Final Office Action dated Jan. 25, 2016, 12 pages.
U.S. Appl. No. 14/179,840, Non-Final Office Action dated Aug. 19, 2015, 8 pages.
U.S. Appl. No. 14/179,840, Notice of Allowance dated Apr. 4, 2018, 8 pages.
Australian Application No. 2013201835, First Examination Report dated May 8, 2014, 5 pages.
Becker et al., Reovirus Sigma NS Protein is Required for Nucleation of Viral Assembly Complexes and Formation of Viral Inclusions, Journal of Virology, vol. 75, No. 3, Feb. 2001, pp. 1459-1475.
Canadian Application No. 2,678,721, Office Action dated Jan. 30, 2015, 4 pages.
Canadian Application No. 2,678,721, Office Action dated May 16, 2016, 4 pages.
Chappell et al., Sequence Diversity within the Reovirus S2 Gene: Reovirus Genes Reassort in Nature, and their Termini are Predicted to Form a Panhandle Motif, Journal of Virology, vol. 68, No. 2, Feb. 1994, pp. 750-756.
Chinese Application No. 201310353609.2, Office Action dated Jul. 31, 2017, 11 pages (5 pages of Original Document and 6 pages of English Translation).
Chinese Application No. 201310353609.2, Office Action dated Apr. 19, 2016, 13 pages (6 pages of Original Document and 7 pages of English Translation).
Chinese Application No. 201310353609.2, Office Action dated Dec. 13, 2016, 13 pages (5 pages of Original Document and 8 pages of English Translation).
Chinese Application No. 201310353609.2, Office Action dated Feb. 17, 2015, 7 pages (3 pages of Original Document and 4 pages of English Translation).
Chinese Application No. 201310353609.2, Office Action dated Oct. 8, 2015, 9 pages (4 pages of Original Document and 5 pages of English Translation).
Dermody et al., The S2 Gene Nucleotide Sequences of Prototype Strains of the Three Reovirus Serotypes Characterization of Reovirus Core Protein 2, Journal of Virology, vol. 61, No. 11, Nov. 1991, pp. 5721-5731.
Ebert et al., Adaptation of Reovirus to Growth in the Presence of Protease Inhibitor E64 Segregates with a Mutation in the Carboxy Terminus of Viral Outer-Capsid Protein Sigma3, Journal of Virology, vol. 75, No. 7, Apr. 2001, pp. 3197-3206.
Ebert et al., Orthoreovirus 3 Dearing-Derived E64-Adapted 3 (D-EA3) Sigma 3 Gene, Complete cds, GenBank Accession No. AF332137, Feb. 23, 2001, 1 page.
European Application No. 15176066.7, Extended European Search Report dated Nov. 5, 2015, 9 pages.
Giantini et al., Reovirus Serotype 3, Segment 4, Major Surface Protein Sigma-3 Gene, Complete Coding Sequence, GenBank Accession No. K02739.1, Aug. 3, 1993, 1 page.
Giantini et al., Reovirus Type 3 Genome Segment S4: Nucleotide Sequence of the Gene Encoding a Major Virion Surface Protein, Journal of Virology, vol. 52, No. 3, Dec. 1984, pp. 984-987.
Israel Application No. 200353, Office Action dated Jul. 31, 2014, 2 pages.
Israel Application No. 200353, Office Action dated Apr. 18, 2016, 3 pages.
Israel Application No. 221700, Office Action dated Aug. 10, 2014, 2 pages.
Israel Application No. 221700, Office Action dated Feb. 8, 2016, 2 pages.
Israel Application No. 221701, Office Action dated Aug. 11, 2014, 2 pages.
Israel Application No. 221701, Office Action dated Feb. 8, 2016, 2 pages.
Israel Application No. 221702, Office Action dated Aug. 11, 2014, 2 pages.
Israel Application No. 221702, Office Action dated Feb. 8, 2016, 2 pages.
Indian Application No. IN5769/DELNP/2009, First Examination Report dated Jan. 6, 2015, 4 pages.
Joklik et al., What Reassorts When Reovirus Genome Segments Reassort?, The Journal Biological Chemistry, vol. 270, No. 9, Mar. 3, 1995, pp. 4181-4184.
Kim et al., Accession No. A6Y8N9, Submitted (Nov. 2006) to the EMBL/GenBank/DDBJ databases, 2006, 3 pages.
Kim et al., Sigma 3, Database UniProt, Accession No. Q06BD2, Oct. 31, 2006, 1 page.
Korean Application No. 10-2009-7019418, Office Action dated Nov. 20, 2014, 11 pages.
Korean Application No. 10-2009-7019418, Office Action dated Jul. 28, 2015, 3 pages.
Korean Application No. 10-2009-7019418, Office Action dated Jan. 27, 2016, 5 pages.
McCutcheon et al., Mammalian Orthoreovirus 3 Strain Dearing Sigma 3 (S4) mRNA, Partial Eds, Database GenBank, Accession No. DQ915165, vol. 264, No. 1, Sep. 26, 2006, 1 page.
McCutcheon et al., Mammalian Reovirus M3 Gene Sequences and Conservation of Coiled-Coil Motifs Near the Carboxyl Terminus of the MicroNS Protein, Virology, vol. 264, No. 1, Nov. 1999, pp. 16-24.
Nibert et al., Nonrandom Segregation of Parental Alleles in Reovirus Reassortants, Journal of Virology, vol. 70, No. 10, Oct. 1996, pp. 7295-7300.
Richardson et al., Nucleotide Sequence of Reovirus Genome Segment S3, Encoding Non-Structural Protein Sigma NS, Nucleic Acids Research, vol. 11, No. 18, Sep. 24, 1983, pp. 6399-6408.
Roner et al., Identification of Signals Required for the Insertion of Heterologous Genome Segments into the Reovirus Genome, PNAS, vol. 92, Dec. 1995, pp. 12362-12366.
Rudd et al., Correlation Between Interferon Sensitivity of Reovirus Isolates and Ability to Discriminate Between Normal and Ras-Transformed Cells, Journal of General Virology, vol. 86, May 2005, pp. 1489-1497.
Wenske et al., Genetic Reassortment of Mammalian Reoviruses in Mice, Journal of Virology, vol. 56, No. 2, American Society for Microbiology, Nov. 1985, pp. 613-616.
Wetzel et al., Reovirus Variants Selected During Persistent Infections of L Cells Contain Mutations in the Viral S1 and S4 Genes and are Altered in Viral Disassembly, Journal of Virology, vol. 71, No. 2, Feb. 1997, pp. 1362-1369.
Wiener et al., The Sequences of the Reovirus Serotype 1,2, and 3 L 1 Genome Segments and Analysis of the Mode of Divergence of the Reovirus Serotypes, Virology, vol. 169, No. 1, Mar. 1989, pp. 194-203.
Wiener et al., The Sequences of the S2 Genome Segments of Reovirus Serotype 3 and of the dsRNA-Negative Mutant ts447, Virology, vol. 170, No. 1, May 1989, pp. 340-341.
Wilson et al., A Single Mutation in the Carboxy Terminus of Reovirus Outer-Capsid Protein Sigma Confers Enhanced Kinetics of Sigma 3 Proteolysis, Resistance to Inhibitors of Viral Disassembly, and Alterations in Sigma 3 Structure, Journal of Virology, vol. 76, No. 19, Oct. 2002, pp. 9832-9843.

(56) References Cited

OTHER PUBLICATIONS

Yin et al., Comparisons of the M1 Genome Segments and Encoded µ2 Proteins of Different Reovirus Isolates, Virology Journal, vol. 1, No. 6, Sep. 23, 2004, pp. 1-17.

* cited by examiner

Figure 1A

S1:
GCTATTGGTCGGATGGATCCTCGCCTACGTGAAGAAGTAGTACGGCTGATAATCGCATTAACGAGTGATAA
TGGAGCATCACTGTCAAAAGGGCTTGAATCAAGGGTCTCGGCGCTCGAGAAGACGTCTCAAATACACTCTG
ATACTATCCTCCGGATCACCCAGGGACTCGATGATGCAAACAAACGAATCATCGCTCTTGAGCAAAGTCGG
GATGACTTGGTTGCATCAGTCAGTGATGCTCAACTTGCAATCTCCAGATTGGAAAGCTCTATCGGAGCCCT
CCAAACAGTTGTCAATGGACTTGATTCGAGTGTTACCCAGTTGGGTGCTCGAGTGGGACAACTTGAGACAG
GACTTGCAGAGCTACGCGTTGATCACGACAATCTCGTTGCGAGAGTGGATACTGCAGAACGTAACATTGGA
TCATTGACCACTGAGCTATCAACTCTGACGTTACGAGTAACATCCATACAAGCGGATTTCGAATCTAGGAT
ATCCACGTTAGAGCGCACGGCGGTCACTAGCGCGGGAGCTCCCCTCTCAATCCGTAATAACCGTATGACCA
TGGGATTAAATGATGGACTCACGTTGTCAGGGAATAATCTCGCCATCCGATTGCCAGGAAATACGGGTCTG
AATATTCAAAATGGTGGACTTCAGTTTCGATTTAATACTGATCAATTCCAGATAGTTAATAATAACTTGAC
TCTCAAGACGACTGTGTTTGATTCTATCAACTCAAGGATAGGCGCAACTGAGCAAAGTTACGTGGCGTCGG
CAGTGACTCCCTTGAGATTAAACAGTAGCACGAAGGTGCTGGATATGCTAATAGACAGTTCAACACTTGAA
ATTAATTCTAGTGGACAGCTAACTGTTAGATCGACATCCCCGAATTTGAGGTATCCGATAGCTGATGTTAG
CGGCGGTATCGGAATGAGTCCAAATTATAGGTTTAGGCAGAGCATGTGGATAGGAATTGTCTCCTATTCTG
GTAGTGGGCTGAATTGGAGGGTACAGGTGAACTCCGACATTTTTATTGTAGATGATTACATACATATATGT
CTTCCAGCTTTTGACGGTTTCTCTATAGCTGACGGTGGAGATCTATCGTTGAACTTTGTTACCGGATTGTT
ACCACCGTTACTTACAGGAGACACTGAGCCCGCTTTTCATAATGACGTGGTCACATATGGAGCACAGACTG
TAGCTATAGGGTTGTCGTCGGGTGGTGCGCCTCAGTATATGAGTAAGAATCTGTGGGTGGAGCAGTGGCAG
GATGGAGTACTTCGGTTACGTGTTGAGGGGGGTGGCTCAATTACGCACTCAAACAGTAAGTGGCCTGCCAT
GACCGTTTCGTACCCGCGTAGTTTCACGTGAGGATCAGACCACCCCGCGGCACTGGGGCATTTCATC
(SEQ ID NO:1)

S2:
GCTATTCGCTGGTCAGTTATGGCTCGCGCTGCGTTCCTATTCAAGACTGTTGGGTTTGGTGGTCTGCAAAA
TGTGCCAATTAACGACGAACTATCTTCACATCTACTCCGAGCTGGTAATTCACCATGGCAGTTAACACAGT
TTTTAGACTGGATAAGCCTTGGGAGGGGTTTAGCTACATCGGCTCTCGTTCCGACGGCTGGGTCAAGATAC
TATCAAATGAGTTGCCTTCTAAGTGGCACTCTCCAGATTCCGTTCCGTCCTAACCACCGATGGGGAGACAT
TAGGTTCTTACGCTTAGTGTGGTCAGCTCCTACTCTCGATGGATTAGTCGTAGCTCCACCACAAGTTTTGG
CTCAGCCCGCTTTGCAAGCACAGGCAGATCGAGTGTACGACTGCGATGATTATCCATTTCTAGCGCGTGAT
CCAAGATTCAAACATCGGGTGTATCAGCAATTGAGTGCTGTAACTCTACTTAACTTGACAGGTTTTGGCCC
GATTTCCTACGTTCGAGTGGATGAAGATATGTGGAGTGGAGATGTGAACCAGCTTCTCATGAACTATTTCG
GGCACACGTTTGCAGAGATTGCATACACATTGTGTCAAGCCTCGGCTAATAGGCCTTGGGAATATGACGGT
ACATATGCTAGGATGACTCAGATTGTGTTATCCTTGTTCTGGCTATCGTATGTCGGTGTAATTCATCAGCA
GAATACGTATCGGACATTCTATTTTCAGTGTAATCGGCGAGGTGACGCCGCTGAGGTGTGGATTCTTTCTT
GTTCGTTGAACCATTCCGCACAAATTAGACCGGGTAATCGTAGCTTATTCGTTATGCCAACTAGCCCAGAT
TGGAACATGGACGTCAATTTGATCCTGAGTTCAACGTTGACGGGGTGTTTGTGTTCGGGTTCACAGCTGCC
ACTGATTGACAATAATTCAGTACCTGCAGTGTCGCGTAACATCCATGGCTGGACTGGTAGAGCTGGTAACC
AATTGCATGGGTTCCAGGTGAGACGAATGGTGACTGAATTTTGTGACAGGTTGAGACGCGATGGTGTCATG
ACCCAAGCTCAGCAGAATCAAGTTGAAGCGTTGGCAGATCAGACTCAACAGTTTAAGAGGGACAAGCTCGA
AACGTGGGCGAGAGAAGACGATCAATATAATCAGGCTCATCCCAACTCCACAATGTTCCGTACGAAACCAT
TTACGAATGCGCAATGGGACGAGGTAATACGGGGCGACTAGTGCCGCGATTGCAGCCCTTATCTGATCG
TCTTGGAGTGAGGGGGTCCCCCCACACACCTCACGACTGACCACACATTCATC (SEQ ID NO:2)

S3:
GCTAAAGTCACGCCTGTCGTCGTCACTATGGCTTCCTCACTCAGAGCTGCGATCTCCAAGATCAAGAGGGA
TGACGTCGGTCAGCAAGTTTGTCCTAATTATGTCATGCTGCGGTCCTCTGTCACAACAAAGGTGGTACGAA
ATGTGGTTGAGTATCAAATTCGTACGGGCGGATTCTTTTCGTGCTTAGCTATGCTAAGGCCACTCCAGTAC
GCTAAGCGTGAGCGTTTGCTTGGTCAGAGGAATCTGGAACGTATATCGACTAGGGATATCCTTCAGACTCG
TGATTTACACTCACTATGTATGCCAACTCCTGATGCGCCAATGTCTAATCATCAAGCATCCACCATGAGAG
AGCTGATTTGCAGTTACTTCAAGGTCGATCATGCGGATGGGTTGAAATATATACCCATGGATGAGAGATAC

Figure 1B

TCTCCGTCATCACTTGCCAGATTGTTTACCATGGGCATGGCTGGGCTGCACATTACCACTGAGCCATCTTA
TAAGCGTGTTCCGATTATGCACTTAGCTGCGGACTTGGACTGTATGACGCTGGCTCTACCTTACATGATTA
CGCTTGATGGTGATACTGTGGTTCCTGTCGCTCCAACACTGTCAGCGGAACAGCTTCTGGACGACGGACTC
AAAGGATTAGCATGCATGGATATCTCCTATGGATGTGAGGTGGACGCGAATAGCCGGCCGGCTGGTGATCA
GAGTATGGACTCTTCACGCTGCATCAACGAGTTGTATTGCGAGGAGACAGCAGAAGCCATCTGTGTGCTTA
AGACATGCCTTGTGTTAAATTGCATGCAGTTTAAACTTGAGATGGATGACCTAGCACATAACGCTGCTGAG
CTGGACAAGATACAGATGATGATACCCTTCAGTGAGCGTGTTTTAGGATGGCCTCGTCCTTTGCGACTAT
TGATGCCCAGTGTTTTAGGTTTTGCGTGATGATGAAGGATAAAAATCTGAAAATAGATATGCGTGAAACGA
CGAGACTGTGGACTCGTTCAGCATCAGATGATTCTGTGGCCACGTCATCTTTAAGTATTTCCCTGGACCGG
GGTCGATGGGTGGCGGCTGACGCCAGTGATGCTAGACTGCTGGTTTTTCCGATTCGCGTGTAATGGGTGAG
TGAGCTGATGTGGTCGCCAAGACATGTGCCGGTGTCTTGGTGGTGGGTGACGCCTAATCATC (SEQ ID
NO:3)

S4:
GCTATTTTTGCCTCTTCCCAGACGTTGTCGCAATGGAGGTGTGCTTGCCCAACGGTCATCAGGTCGTGGAC
TTAATTAACAACGCTTTTGAAGGTCGTGTATCAATCTACAGCGCGCAAGAGGGATGGGACAAAACAATCTC
AGCACAGCCAGATATGATGGTATGTGGTGGCGCCGTCGTTTGCATGCATTGTCTAGGTGTTGTTGGATCTC
TACAACGCAAGCTGAAGCATTTGCCTCACCATAGATGTAATCAACAGATCCGTCATCAGGATTACGTCGAT
GTACAGTTCGCAGACCGTGTTACTGCTCACTGGAAGCGGGGTATGCTGTCCTTCGTTGCGCAGATGCACGA
GATGATGAATGACGTGTCGCCAGATGACCTGGATCGTGTGCGTACTGAGGGAGGTTCACTAGTGGAGCTGA
ACCGGCTTCAGGTTGACCCAAATTCAATGTTTAGATCAATACACTCAAGTTGGACAGATCCTTTGCAGGTG
GTGGACGACCTTGACACTAAGCTGGATCAGTACTGGACAGCCTTAAACCTGATGATCGACTCATCCGACTT
GATACCCAACTTTATGATGAGAGACCCATCACACGCGTTCAATGGTGTGAAACTGAAGGGAGATGCTCGTC
AAACCCAATTCTCCAGGACTTTTGATTCGAGATCGAGTTTGGAATGGGGTGTGATGGTTTATGATTACTCT
GAGCTGGATCATGATCCATCGAAGGCCGTGCTTACAGAAAGGAATTGGTGACGCCAGCTCGAGATTTCGG
TCACTTTGGATTATCCCATTATTCTAGGGCGACTACCCCAATCCTTGGAAAGATGCCGGCCGTATTCTCAG
GAATGTTGACTGGGAACTGTAAAATGTATCCATTCATTAAAGGAACGGCTAAGCTGAAGACAGTGCGCAAG
CTAGTGGAGGCAGTCAATCATGCTTGGGGTGTCGAGAAGATTAGATATGCTCTTGGGCCAGGTGGCATGAC
GGGATGGTACAATAGGACTATGCAACAGGCCCCATTGTGCTAACTCCTGCTGCTCTCACAATGTTCCCAG
ATACCATCAAGTTTGGGGATTTGAATTATCCAGTGATGATTGGCGATCCGATGATTCTTGGCTAAACACCC
CCATCTTCACAGCGCCGGGCTTGACCAACCTGGTGTGACGTGGGACAGGCTTCATTCATC (SEQ ID
NO:4)

Figure 2A

M1:
GCTATTCGCGGTCATGGCTTACATCGCAGTTCCTGCGGTGGTGGATTCACGTTCGAGTGAGGCTATTGGAC
TGCTAGAATCGTTTGGAGTAGACGCTGGGGCTGACGCGAATGACGTTTCATATCAAGATCATGACTATGTG
TTGGATCAGTTACAGTACATGTTAGATGGATATGAGGCTGGTGACGTTATCGATGCACTCGTCCACAAGAA
TTGGTTACATCACTCTGTCTATTGCTTGTTGCCACCCAAAAGTCAACTATTAGAGTATTGGAAAAGTAATC
CTTCAGCGATACCGGACAACGTTGATCGTCGGCTTCGTAAACGACTAATGCTAAAGAAAGATCTCAGGAAA
GATGATGAATACAATCAGCTAGCGCGTGCTTTCAAGATATCGGATGTCTACGCACCTCTCATCTCATCCAC
GACGTCACCGATGACAATGATACAGAACTTGAATCGAGGCGAGATCGTGTACACCACGACGGACAGGGTAA
TAGGGGCTAGAATCTTGTTATATGCTCCTAGAAAGTACTATGCGTCAACTCTGTCATTTACTATGACTAAG
TGCATCATTCCGTTTGGTAAAGAGGTGGGTCGTGTTCCTCACTCTCGATTTAATGTTGGCACATTTCCGTC
AATTGCTACCCCGAAATGTTTTGTCATGAGTGGGGTTGATATTGAGTCCATCCCAAATGAATTTATCAAGT
TGTTTTACCAGCGCGTCAAGAGTGTTCACGCTAACATACTAAATGACATATCTCCTCAGATCGTCTCTGAC
ATGATAAACAGAAAGCGTCTGCGCGTTCATACTCCATCAGATCGTCGAGCCGCGCAGTTGATGCATTTGCC
TTACCATGTTAAACGAGGAGCGTCTCACGTCGACGTTTACAAGGTGGATGTTGTAGACATGTTGTTCGAGG
TAGTGGATGTGGCCGATGGGTTGCGCAACGTATCTAGGAAACTAACTATGCATACCGTTCCTGTATGTATT
CTTGAAATGTTGGGTATTGAGATTGCGGACTATTGCATTCGTCAAGAGGATGGAATGCTCACAGATTGGTT
CCTACTTTTAACCATGCTATCTGATGGCTTGACTGATAGAAGGACGCATTGTCAATACTTGATTAATCCGT
CAAGTGTGCCTCCTGATGTGATACTTAACATCTCAATTACTGGATTTATAAATAGACATACAATCGATGTC
ATGCCTGACATATATGACTTCGTTAAACCCATTGGCGCTGTGCTGCCTAAGGGATCATTTAAATCAACAAT
TATGAGAGTTCTTGATTCAATATCAATATTAGGAATCCAAATCATGCCGCGCGCGCATGTAGTTGACTCAG
ATGAGGTGGGCGAGCAAATGGAGCCTACGTTTGAGCAGGCGGTTATGGAGATATACAAAGGGATTGCTGGC
GTTGACTCGCTGGATGATCTCATCAAGTGGGTGTTGAACTCGGATCTCATTCCGCATGATGACAGGCTTGG
TCAATTATTTCAAGCGTTTTTGCCTCTCGCAAAGGACTTATTAGCTCCAATGGCCAGAAAGTTTTATGATA
ACTCAATGAGTGAGGGTAGATTGCTAACATTCTCTCATGCCGACAGTGAGTTGCTGAACGCAAATTATTTT
GGTCATTTATTGCGACTAAAAATACCATATATTACAGAGGTTAATCTGATGATTCGCAAGAATCGTGAGGG
TGGAGAGCTATTTCAGCTTGTGTTATCTTATCTATATAAAATGTATGCTACTAGCGCGCAGCCTAAATGGT
TTGGATCATTATTGCGATTGTTAATATGTCCCTGGTTACATATGGAGAAATTAATAGGAGAAGCAGACCCG
GCATCTACGTCGGCTGAAATTGGGTGGCATATCCCTCGTGAACAGCTGATGCAAGATGGATGGTGTGGATG
TGAAGACGGATTCATTCCCTATGTTAGCATACGTGCGCCAAGACTGGTTATAGAGGAGTTGATGGAGAAGA
ACTGGGGCCAATATCATGCCCAAGTTATTGTCACTGATCAGCTTGTCGTAGGCGAACCGCGGAGGGTATCT
GCTAAGGCTGTGATCAAGGGTAACCACTTACCAGTTAAGTTAGTTTCACGATTTGCATGTTTCACATTGAC
GGCGAAGTATGAGATGAGGCTTTCGTGCGGCCATAGCACTGGACGTGGAGCTGCATACAGTGCGAGACTAG
CTTTCCGATCTGACTTGGCGTGATCCGTGACATGCGTAGTGTGACACCTGCTCCTAGGTCAATGGGGGTAG
GGGGCGGGCTAAGACTACGTACGCGCTTCATC (SEQ ID NO:5)

M2:
GGCTAATCTGCTGACCGTTACTCTGCAAAGATGGGGAACGCTTCCTCTATCGTTCAGACGATCAACGTCAC
TGGAGATGGCAATGTATTTAAACCATCAGCTGAAACTTCATCTACCGCTGTACCATCGTTAAGCTTATCAC
CTGGAATGCTGAATCCCGGAGGGGTACCATGGATTGCTGTTGGAGATGAGACATCTGTGACTTCACCAGGC
GCATTACGTCGAATGACGTCAAAGGACATCCCGGACACGGCAATAATCAACACAGACAATTCATCAGGCGC
CGTGCCAAGCGAATCAGCCTTGGTGCCCTACATCGATGAGCCGCTGGTAGTGGTTACAGAGCATGCTATTA
CCAACTTCACCAAAGCTGAGATGGCACTTGAATTCAATCGTGAGTTCCTTGACAAGATGCGTGTGCTGTCA
GTGTCACCAAAATATTCGGATCTTCTGACCTATGTTGACTGCTACGTCGGTGTGTCTGCTCGTCAGGCTTT
AAACAATTTTCAGAAACAAGTGCCTGTGATTACACCTACTAGGCAGACGATGTATGTCGACTCGATACAAG
CGGCCTTGAAAGCTTTAGAAAAGTGGGAGATTGATCTGAGAGTGGCTCAAACGTTGCTGCCTACGAACGTT
CCGATTGGAGAAGTCTCTTGTCCAATGCAGTCGGTAGTGAAACTGCTGGATGATCAGCTGCCAGATGACAG
CCTGATACGGAGGTATCCCAAGGAAGCCGCCGTCGCTTTGGCTAAACGAAACGGGGGAATACAATGGATGG
ACGTATCAGAAGGCACCGTGATGAACGAGGCTGTCAACGCTGTTGCAGCTAGTGCACTGGCACCTTCAGCA
TCAGCCCCACCCTTAGAAGAGAAGTCAAAGTTAACCGAACAAGCGATGGATCTCGTGACCGCGGCTGAGCC
TGAGATAATTGCCTCACTCGCGCCAGTTCCCGCACCCGTGTTTGCCATACCACCTAAACCAGCAGATTATA
ATGTGCGTACTCTGAGGATCGACGAGGCCACTTGGCTGCGAATGATTCCAAAATCAATGAACACACCTTTT
CAAATCCAGGTGACTGATAACACAGGAACTAATTGGCATCTCAATTTGAGGGGGGGGACTCGTGTAGTGAA

Figure 2B

TCTGGACCAAATCGCTCCGATGCGGTTTGTATTAGATCTAGGGGGAAAGAGTTATAAAGAGACGAGCTGGG
ATCCAAACGGCAAGAAGGTCGGATTCATCGTTTTTCAATCGAAGATACCATTCGAACTTTGGACTGCTGCT
TCACAGATCGGTCAAGCCACGGTGGTTAACTATGTCCAACTATACGCTGAAGACAGCTCATTTACCGCGCA
GTCTATCATTGCTACTACCTCTTTGGCTTATAACTATGAGCCTGAGCAGTTGAATAAGACTGACCCTGAGA
TGAATTATTATCTTTTGGCGACCTTTATAGACTCAGCCGCTATAACGCCAACGAATATGACACAGCCTGAT
GTTTGGGATGCCTTGCTGACGATGTCCCCACTATCAGCTGGCGAGGTGACAGTGAAGGGTGCGGTAGTGAG
TGAAGTAGTCCCTGCAGACTTGATAGGTAGCTACACTCCAGAATCCCTAAACGCCTCACTTCCGAATGATG
CTGCTAGATGCATGATCGATAGAGCTTCGAAGATAGCCGAAGCAATCAAGATTGATGATGATGCTGGACCA
GATGAATATTCCCCAAACTCTGTACCAATTCAAGGTCAGCTTGCTATCTCGCAACTCGAAACTGGATATGG
TGTGCGAATATTCAACCCTAAAGGGATCCTTTCTAAAATTGCATCTAGGGCAATGCAGGCTTTCATTGGTG
ACCCGAGCACAATCATCACGCAGGCGGCGCCAGTGTTATCAGACAAGAATAATTGGATTGCATTGGCACAG
GGAGTGAAAACTAGTCTGCGTACTAAAAGTCTATCAGCGGGAGTGAAGACTGCAGTGAGTAAGCTGAGCTC
ATCTGAGTCTATCCAGAATTGGACTCAAGGATTCTTGGATAAAGTGTCAGCGCATTTTCCAGCACCAAAGC
CCGATTGTCCGACTAGCGGAGATAGTGGTGAATCGTCTAATCGCCGAGTGAAGCGCGACTCATACGCAGGA
GTGGTCAAACGTGGGTACACACGTTAGGCCGCTCGCCCTGGTGACGCGGGGTTAAGGGATGCAGGCAAATC
ATC (SEQ ID NO:6)

M3:
GCTAAAGTGACCGTGGTCATGGCTTCATTCAAGGGATTCTCCGCCAACACTGTTCCAGTTTCTAAGGCCAA
GCGTGACATATCATCTCTTGCCGCTACTCCTGGACTTCGTTCACAATCCTTCACTCCGTCTGTGGATATGT
CTCAATCGCGTGAATTCCTCACAAAGGCAATTGAGCAAGGGTCCATGTCTATACCTTATCAGCATGTGAAT
GTACCGAAAGTTGATCGTAAAGTTGTTAGCCTGGTAGTGCGACCTTTCTCTTCAGGTGCTTTCTCTATCTC
TGGAGTGATTTCGCCAGCCCATGCCTATCTACTAGAGTGTCTACCCCAGCTTGAGCAGGCGATGGCTTTTG
TTGCTTCACCTGAGTCTTTCCAGGCTTCCGACGTCGCGAAGCGCTTTGCCATAAAGCCAGGTATGAGCCTC
CAGGATGCCATCACTGCCTTTATTAACTTTGTGTCCGCGATGCTGAAAATGACGGTGACTCGTCAAAACTT
TGACGTTATTGTGGCTGAGATCGAGAGGCTTGCTTCAACCAGCGTGTCCGTCAGGACTGAAGAAGCGAAGG
TTGCTGATGAGGAGCTAATGCTATTCGGGTTAGATCATAGAGGGCCACAGCAGCTGGATGTTTCTGACGCT
AAAGGGATAATGAAGGCTGCTGATATTCAGACAACTCATGATGTCCATTTGGCACCAGGCGTTGGTAATAT
TGATCCTGAAATCTATAACGAGGGCGGTTCATGTTCATGCAGCACAAGCCACTTGCGGCGGATCAATCGT
ATTTCACCTTGGAGACTGCGGATTATTTCAAGATTTATCCAACATACGATGAACATGATGGCAGGATGGCT
GACCAAAAGCAGTCGGGATTGATACTGTGTACTAAGGACGAGGTATTGGCTGAGCAAACTATATTTAAACT
GGACGCCCCTGATGACAAGACTGTTCATCTGTTGGATCGCGATGACGACCACGTTGTTGCCAGATTTACTA
AGGTATTTATAGAGGACGTGGCTCCCGGGCATCATGCTGCTCAAAGATCGGGACAACGCTCTGTGCTTGAT
GACCTATATGCGAATACGCAAGTGATTTCCATTACTTCTGCTGCTTTAAAGTGGGTGGTCAAGCACGGCGT
ATCTGATGGAATCGTGAACAGGAAGAATGTCAAAGTGTGTGTTGGTTTTGACCCCCTGTACACCTTGTCTA
CACATAACGGGGTGTCCTTATGTGCCCTGCTGATGGACGAAAAACTCTCTGTGCTGAACAGTGCGTGTCGT
ATGACGTTACGCTCACTCATGAAGACCGGACGCGACGTTGATGCACACAGAGCTTTTCAGCGAGTCCTCTC
TCAAGGATACACATCGCTAATGTGCTACTATCATCCTTCACGGAAGTTGGCATATGGTGAGGTGCTCTTTC
TAGAACGATCCAATGACGTGACAGATGGGATCAAGCTTCAGTTGGACGCATCTAGACAGTGTCATGAATGT
CCTGTGTTGCAGCAGAAAGTGGTTGAGTTAGAGAAACAGATTATTATGCAGAAGTCAATCCAGTCAGACCC
TACCCCAGTGGCGCTGCAACCATTGTTGTCTCAGTTGCGTGAGTTGTCTAGTGAAGTTACTAGGCTACAGA
TGGAGTTGAGTCGAGCTCAGTCCCTGAATGCTCAGTTGGAGGCGGATGTCAAGTCAGCTCAATCATGTAGC
TTGGATATGTATCTGAGACACCACACTTGCATTAATGGTCATGCTAAAGAAGATGAATTGCTTGACGCTGT
GCGTGTCGCGCCGGATGTGAGGAGAGAAATCATGGAAAAGAGGAGTGAAGTGAGACAAGGTTGGTGCGAAC
GTATTTCTAAGGAAGCAGCTGCCAAATGTCAAACTGTTATTGATGACCTGACTTTGATGAATGGAAAGCAA
GCACAAGAGATAACAGAATTACGTGATTCGGCTGAAAAATATGAGAAACAGATTGCAGAGCTGGTGAGTAC
CATCACCCAAAACCAGATAACGTATCAGCAAGAGCTACAAGCCTTGGTAGCGAAAAATGTGGAATTGGACG
CGTTGAATCAGCGTCAGGCTAAGTCTTTGCGTATTACTCCCTCTCTTCTATCAGCCACTCCTATCGATTCA
GTTGATGATGTTGCTGACTTAATTGATTTCTCTGTTCCAACTGATGAGTTGTAAATAATCCGTGATGCAGT
GTTGCCCTAATCCCTTAAGCCTTCCCGACCCCCATTCATC (SEQ ID NO:7)

Figure 3A

L1:
GCTACACGTTCCACGACAATGTCATCCATGATACTGACTCAGTTTGGACCGTTCATTGAGAGCATTTCAGG
TATCACTGATCAATCGAATGACGTGTTTGAAGATGCAGCAAAAGCATTCTCTATGTTTACTCGCAGCGATG
TCTACAAGGCGCTGGATGAAATACCTTTCTCTGATGATGCGATGCTTCCAATCCCTCCAACTATATATACG
AAACCATCTCACGATTCATATTATTACATTGATGCTCTAAACCGTGTGCGTCGCAAAACATATCAGGGCCC
TGATGACGTGTACGTACCTAATTGTTCTATTGTTGAATTGCTGGAGCCACATGAGACTCTGACATCTTATG
GGCGGTTGTCCGAGGCCATCGAGAATCGTGCCAAGGATGGGACAGCCAAGCCAGAATCGCCACAACGTAT
GGTAGAATCGCTGAATCTCAAGCTCGACAGATTAAGGCTCCATTGGAGAAGTTTGTGTTGGCACTATTAGT
GGCCGAAGCAGGGGGGTCTTTATATGATCCAGTTTTGCAGAAGTATGATGAGATTCCAGATCTATCGCATA
ATTGCCCTTTATGGTGTTTTAGAGAGATCTGTCGTCACATATCTGGTCCATTACCAGATCGGGCACCTTAT
CTTTACTTATCTGCAGGGGTTTTCTGGTTAATGTCACCACGAATGACGTCTGCAATCCCTCCGCTACTATC
CGATCTTGTTAATTTAGCTATTTTGCAACAAACTGCGGGTTTAGATCCATCATTAGTGAAATTGGGAGTAC
AGATATGCCTTCATGCAGCAGCTAGCTCAAGTTATGCATGGTTTATCTTAAAGACTAAGTCTATTTTTCCT
CAAAACACGTTGCACAGTATGTATGAATCTCTAGAAGGGGATACTGTCCTAATCTTGAATGGTTAGAGCC
TAGATCAGACTATAAGTTCATGTACATGGGAGTCATGCCATTGTCCGCTAAGTATGCTAGGTCGGCGCCGT
CCAATGATAAGAAAGCGCGGGAACTTGGCGAGAAATATGGACTGAGCTCAGTCGTCGGTGAGCTTCGTAAA
CGGACAAAGACGTATGTTAAACATGACTTTGCTTCAGTGAGGTACATTCGTGACGCTATGGCATGTACTAG
CGGTATTTTCTTGGTAAGAACACCCACCGAAACGGTATTGCAAGAATATACGCAGAGTCCGGAGATTAAGG
TTCCCATTCCCCAGAAAGACTGGACAGGCCCAATAGGTGAAATCAGAATTCTAAAAGATACAACAAGTTCC
ATCGCGCGTTACTTATATAGAACATGGTACTTGGCAGCGGCGAGAATGGCGGCTCAACCACGTACGTGGGA
TCCATTGTTTCAAGCGATTATGAGATCTCAATACGTGACAGCTAGGGTGGATCTGGCGCAGCACTCCGCG
AATCTTTGTATGCAATCAATGTGTCGTTACCTGATTTCAAGGGCTTACCAGTGAAGGCAGCAACTAAGATA
TTCCAGGCGGCACAATTAGCGAACTTGCCGTTCTCCCACACATCAGTGGCTATACTAGCTGACACTTCAAT
GGGATTGCGAAATCAGGTGCAGAGGCGGCCACGATCCATTATGCCATTAAATGTGCCCCAGCAGCAGGTTT
CGGCGCCCCATACATTGACAGCGGATTACATTAACTACCACATGAATCTATCAACCACGTCTGGTAGTGCG
GTCATTGAGAAGGTGATTCCTTTAGGTGTATACGCTTCGAGCCCTCCTAACCAGTCGATCAACATTGACAT
ATCTGCGTGTGACGCTAGTATTACTTGGGATTTCTTTCTGTCAGTGATTATGGCGGCTATACACGAAGGTG
TCGCTAGTAGCTCCATTGGAAAACCATTTATGGGGGTTCCTGCATCCATTGTAAATGATGAGTCTGTCGTT
GGAGTGAGAGCTGCTAGGCCGATATCGGGAATGCAGAACATGATTCAGCATCTATCGAAACTATATAAACG
TGGATTTTCATATAGAGTAAACGATTCTTTTTCTCCAGGTAACGATTTTACTCATATGACTACCACTTTCC
CGTCAGGTTCAACAGCCACCTCTACTGAGCATACTGCTAATAATAGTACGATGATGGAAACTTTCCTGACA
GTATGGGGACCCGAACATACTGACGACCCTGACGTCTTACGTTTAATGAAGTCTTTAACTATTCAAAGGAA
TTACGTATGTCAAGGTGATGATGGATTAATGATTATCGATGGGACTACTGCTGGTAAGGTGAACAGTGAAA
CTATTCAGAAGATGCTAGAATTAATCTCAAAATATGGTGAGGAATTCGGATGGAAATATGACATAGCGTAC
GATGGGACTGCCGAATACTTAAAGCTATACTTCATATTTGGCTGTCGAATTCCAAATCTTAGTCGCCATCC
AATCGTGGGGAAAGAACGGGCGAATTCTTCAGCAGAGGAGCCATGGCCAGCAATTCTAGATCAGATTATGG
GTGTCTTCTTTAATGGTGTTCATGATGGGTTACAGTGGCAGCGGTGGATACGTTATTCATGGGCTCTATGC
TGTGCTTTCTCACGTCAAAGAACAATGATTGGTGAGAGCGTGGGTTACCTTCAATATCCTATGTGGTCTTT
TGTCTACTGGGGATTACCACTGGTTAAAGCGTTTGGGTCAGACCCATGGATATTTTCTTGGTACATGCCTA
CTGGAGATCTGGGAATGTATAGTTGGATTAGCTTGATACGCCCTCTGATGACAAGATGGATGGTGGCTAAT
GGTTACGTAACTGACAGATGCTCACCCGTATTCGGGAACGCAGATTATCGCAGGTGTTTCAATGAACTTAA
ACTATATCAAGGTTATTATATGGCACAATTGCCCAGGAATCCTAAGAAGTCTGGACGAGCGGCCCCTCGGG
AGGTAAGAGAACAATTCACTCAGGCATTATCCGACTATCTACTGCAAAATCCAGAGCTGAAGTCACGTGTG
CTACGTGGTCGTAGTGAGTGGGAGAAATATGGAGCGGGATAATTCACAATCCTCCGTCATTATTCGATGT
GCCCCATAAATGGTATCAGGGTGCGCAAGAGGCAGCAATCGCTACGAGAGAAGAGCTGGCAGAAATGGATG
AGACATTAATGCGCGCTCGAAGGCACAGATATTCGAGCTTTTCAAAGTTATTAGAGGCGTATCTGCTCGTG
AAATGGCGAATGTGCGAGGCCCGCGAACCGTCGGTGGATTTGCGATTACCATTATGTGCGGGTATTGACCC
ATTAAACTCAGATCCTTTTCTCAAGATGGTAAGCGTTGGACCAATGCTCCAGAGTACGAGAAAGTACTTTG
CTCAGACACTATTCATGGCAAGACGGTGTCGGTCTTGACGTTAACGCGATTGATAGCGCGTTATTACGA
CTGCGAACATTAGGTGCTGATAAGAAAGCATTAACGGCGCAGTTATTAATGGTGGGCTTCAGGAGTCAGA
AGCGGACGCATTGGCCGGGAAGATAATGCTACAGGATGTGAATACTGTGCAATTAGCCAGAGTGGTTAACT
TAGCTGTGCCAGATACTTGGATGTCGTTAGACTTTGACTCTATGTTCAAACACCACGTCAAGCTGCTTCCC
AAAGATGGACGTCATCTAAATACTGATATTCCTCCTCGAATGGGATGGTTACGGGCCATTTTACGATTCTT

Figure 3B

AGGTGCCGGAATGGTAATGACTGCGACTGGAGTTGCTGTCGACATCTATCTGGAGGATATACATGGCGGTG
GTCGGTCACTTGGACAGAGATTCATGACTTGGATGCGACAGGAAGGACGGTCAGCGTGAGTCTACCATGGG
TCGTGGTGCGTCAACTCATC  (SEQ ID NO:8)

L2:
GCTAAATGGCGCGATGGCGAACGTTTGGGGGGTGAGACTTGCAGACTCGTTATCTTCACCCACTATTGAGA
CACGAACGCGTCAGTATACCTTACACGATCTTTGCTCAGACCTAGATGCTAATCCGGGGAGGGAACCGTGG
AAACCTCTGCGTAATCAGCGTACTAATAATATTGTGGCTGTGCAATTATTCAGACCATTGCAGGGTTTAGT
TTTAGATACCCAGCTTTATGGATTTCCAGGAGCATTTGATGACTGGGAGCGATTCATGAGAGAGAAGCTGC
GTGTGCTAAAGTATGAAGTATTGCGCATCTATCCAATCAGCAACTATAGCAATGAACATGTCAACGTCTTC
GTGGCCAATGCTTTGGTGGGCGCTTTCCTGTCGAATCAAGCTTTCTATGACCTGCTACCGTTGTTGATAAT
TAATGACACTATGATTGGTGATCTACTTGGCACGGGGGCATCGCTATCACAGTTCTTTCAATCTCATGGAG
ATGTGCTGGAAGTCGCAGCTGGTCGTAAGTATCTGCAGATGGAAAACTACTCCAACGATGACGATGATCCT
CCATTATTTGCGAAAGACCTGTCAGATTATGCTAAAGCATTCTACAGTGACACATATGAAGTGTTGGACAG
GTTCTTTTGGACGCATGACTCTTCAGCGGGGTCTTAGTGCATTATGATAAGCCAACGAATGGTCATCACT
ATCTGCTGGGTACTTTGACTCAGATGGTCAGTGCACCTCCTTATATTATTAACGCTACTGACGCAATGTTG
CTTGAATCCTGTCTAGAACAGTTCTCAGCTAATGTGCGTGCGAGACCTGCGCAACCCGTTACACGCTTAGA
CCAATGCTATCATTTAAGATGGGGAGCACAATATGTAGGAGAAGATTCACTGACATATCGGTTGGGGGTGT
TATCCTTGCTGGCTACCAATGGATATCAATTAGCTAGACCGATTCCAAGACAGTTGACGAATCGATGGTTG
TCGAGCTTTGTGAGTCAAATTATGTCTGACGGCGTCAACGAGACTCCACTGTGGCCCCAAGAAAGGTATGT
GCAGATCGCTTATGATTCACCATCCGTTGTTGATGGGGCTACGCAATATGGCTATGTCAGGAAGAATCAAC
TCAGACTCGGCATGAGAATATCGGCGCTGCAATCGCTGAGTGATACGCCCTCGCCGGTACAGTGGCTTCCA
CAATACACCATCGACCAGGCAGCGATGGACGAAGGCGATCTGATGGTTAGTCGGCTTACGCAACTCCCGTT
ACGTCCTGATTATGGTAATATCTGGGTCGGCGATGCGCTATCCTATTATGTGGACTACAATCGGAGTCATC
GAGTCGTGCTTTCATCGGAACTTCCTCAGCTTCCGGACACATATTTTGATGGCGATGAACAGTATGGGCGC
AGCCTGTTCTCACTAGCTCGTAAGATTGGTGACCGCTCGTTAGTGAAAGATACGGCTGTCTTGAAGCACGC
TTACCAAGCCATCGATCCAAATACTGGTAAGGAGTATCTGAGATCTCGGCAATCTGTCGCATATTTTGGTG
CATCAGCGGGTCATTCTGGTGCCGACCAGCCGTTAGTCATAGAGCCCTGGATTCAAGGGAAAATCAGTGGT
GTGCCGCCACCCTCCTCAGTGCGACAGTTCGGCTATGATGTTGCCCGTGGCGCGATCGTCGATCTGGCGAG
ACCATTTCCTTCTGGAGATTATCAATTTGTCTATTCGGATGTTGACCAGGTGGTCGATGGCCATGACGATC
TGAGTATATCATCTGGACTGGTGGAGAGCCTTTTGTCTTCATGCATGCACGCCACAGCACCCGGGGGCTCA
TTTGTTGTTAAGATAAATTTTCCGACTAGACCCGTATGGCACTACATCGAACAGAAGATCTTGCCCAATAT
TACGTCATACATGTTGATCAAGCCTTTCGTCACCAACAACGTCGAATTGTTCTTCGTCGCTTTCGGTGTGC
ATCAACACTCATCACTTACTTGGACATCTGGAGTGTACTTCTTCTTGGTGGACCATTTTTATCGTTATGAG
ACTTTATCTACGATCTCACGACAATTGCCGTCTTTTGGGTATGTTGATGATGGGTCTTCCGTGACTGGTAT
CGAGACAATTAGTATTGAGAACCCTGGCTTCTCGAATATGACCCAGGCCGCTCGCATTGGTATCTCAGGAT
TGTGTGCTAATGTAGGTAACGCGCGTAAGTCCATTGCCATTTACGAATCTCATGGGGCCAGAGTATTAACT
ATCACATCAAGGAGATCTCCGGCATCAGCTAGAAGAAAGTCTAGGTTGCGATATTTGCCATTAATAGACCC
TAGGTCGTTAGAGGTACAGGCGCGCACTATTCTGCCAGCTGATCCAGTGTTATTTGAAAACGTGAGCGGAG
CGTCACCCCATGTTTGTCTGACAATGATGTACAACTTCGAAGTGTCGTCAGCGGTATATGATGGAGACGTT
GTGCTAGATCTTGGGACGGGACCAGAGGCTAAAATCCTTGAACTGATACCCGCAACCTCTCCAGTCACATG
CGTGGACATACGGCCTACAGCGCAGCCTAGTGGATGTTGGAACGTTCGTACCACGTTCCTTGAGTTAGATT
ATTTGAGCGATGGATGGATCACTGGGGTGCGTGGGGACATAGTTACTTGTATGTTATCTTTGGGGCCGCT
GCCGCTGGAAAATCAATGACTTTTGACGCTGCGTTTCAGCAATTAATCAAAGTATTATCCAAGAGTACGGC
TAATGTTGTGCTGGTGCAGGTTAACTGCCCTACAGACGTGGTGAGGAGCATTAAGGGCTACCTAGAGATAG
ATTCGACTAACAAGAGGTATAGGTTCCCCAAATTTGGTCGAGACGAGCCGTACTCTGACATGGATGCGCTG
GAGAAAATATGTCGTACCGCCTGGCCAAACTGCTCAATTACCTGGGTTCCATTGTCATACGACTTGCGGTG
GACTAGACTGGCATTATTAGAGTCCACGACATTGAGTAGCGCGTCGATTAGAATTGCTGAGCTGATGTATA
AATACATGCCTATTATGAGGATTGATATTCATGGACTACCCATGGAAAAGCGAGGTAACTTCATAGTGGGG
CAGAACTGCTCATTAGTAATCCCTGGTTTTAATGCGCAGGATGTCTTTAACTGTTATTTCAATTCCGCCCT
CGCTTTCTCGACTGAAGATGTCAATGCTGCGATGATTCCCCAAGTGTCTGCGCAGTTTGATGCGACTAAGG
GTGAGTGGACGTTGGATATGGTCTTCTCCGACGCAGGAATCTATACCATGCAGGCTCTAGTGGGATCTAAT

Figure 3C

GCTAATCCAGTCTCTTTGGGTTCCTTTGTAGTTGATTCTCCAGATGTAGATATAACTGACGCTTGGCCAGC
TCAGTTAGACTTTACGATCGCGGGAACTGATGTCGATATAACAGTTAATCCTTATTACCGTCTGATGACCT
TTGTAAGGATCGATGGACAGTGGCAGATTGCCAATCCAGACAAATTTCAATTCTTTTCGTCGGCGTCTGGG
ACGTTAGTGATGAACGTCAAATTAGATATCGCAGATAAATATCTACTATACTATATACGAGATGTCCAGTC
TCGAGATGTTGGCTTTTACATTCAGCATCCACTTCAACTTTTGAATACGATCACATTGCCAACCAACGAGG
ACCTTTTTCTGAGCGCACCTGACATGCGAGAGTGGGCAGTTAAGGAAAGCGGTAACACGATATGTATACTC
AATAGTCAAGGGTTTGTGCTACCTCAAGATTGGGATGTGTTAACAGATACCATAAGTTGGTCCCCATCGAT
ACCCACATACATTGTGCCACCGGGTGATTATACCTTGACTCCTCTGTAACTCACTGTCCCTCGTGAGCGCG
CCTAATTCATC (SEQ ID NO:9)

L3:
GCTAATCGTCAGGATGAAGCGGATTCCAAGGAAGACAAAGGGCAAATCCAGCGGAAAGGGCAATGACTCAA
CAGAGAGAGCGGACGATGGCTCGAGCCAATTAAGAGACAAGCAAAACAATAAGGCTGGCCCCGCCACTACG
GAGCCTGGCACATCCAACCGAGAGCAATACAAAGCTCGACCAGGTATTGCATCTGTGCAGAGGGCCACTGA
AAGTGCAGAAATGCCCATGAAGAATAATGACGAAGGGACGCCAGATAAGAAAGGAAATACTAAGGGCGACC
TAGTTAATGAGCATAGTGAGGCTAAAGACGAGGCGGATGAAGCGACGAAGAAGCAGGCAAAGGATACAGAC
AAAAGTAAAGCGCAAGTCACATATTCAGACACTGGTATCAATAATGCTAATGAACTGTCAAGATCTGGGAA
TGTGGATAATGAGGGTGGAAGTAATCAGAAGCCGATGTCTACCAGAATAGCTGAGGCAACGTCTGCTATAG
TGTCGAAACATCCTGCGCGTGTTGGGCTGCCACCTACCGCTAGCAGTGGTCATGGGTATCAGTGCCATGTC
TGTTCTGCAGTCCTGTTTAGTCCTTTAGACCTAGATGCCCACGTCGCCTCACATGGTTTGCATGGTAACAT
GACATTAACATCGAGTGATATCCAGCGACATATAACTGAGTTCATCAGCTCATGGCAAAATCATCCTATTG
TTCAAGTTTCGGCTGATGTCGAAAATAAGAAAACTGCTCAATTGCTTCACGCTGACACTCCTCGACTCGTC
ACTTGGGATGCTGGTTTGTGTACTTCATTCAAAATCGTCCCGATTGTGCCAGCTCAGGTGCCGCAGGATGT
ACTGGCCTATACGTTTTTCACCTCTTCATACGCTATCCAATCACCGTTTCCAGAGGCGGCAGTGTCTAGGA
TTGTGGTGCATACGAGATGGGCATCTAATGTTGACTTTGACCGAGACTCGTCTGTCATCATGGCGCCACCT
ACAGAAAACAATATCCATTTGTTTAAACAGTTACTAAATACTGAAACCCTGTCTGTAAGGGGGCTAATCC
GCTAATGTTCAGGGCAATGTGTTGCATATGTTGCTAGAGTTCGTATTAGATAACTTGTATCTGAACAGAC
ATACGGGATTCTCTCAAGACCACACGCCATTTACTGAGGGTGCTAATTTGCGTTCACTTCCTGGCCCCGAT
GCTGAGAAATGGTACTCGATTATGTATCCAACGCGCATGGGAACGCCGAATGTATCCAAAATATGTAATTT
CGTCGCCTCTTGTGTGCGAAATCGGGTTGGACGGTTTGATCGAGCACAGATGATGAACGGAGCTATGTCAG
AGTGGGTGGATGTCTTCGAGACTTCAGACGCGCTAACCGTCTCCATTCGAGGTCGATGGATGGCTAGACTA
GCTCGCATGAACATAAATCCAACAGAGATCGAATGGGCATTGACTGAATGTGCACAAGGATATGTGACTGT
CACAAGTCCTTACGCTCCTAGCGTAAATAGATTGATGCCCTATCGTATCTCCAACGCTGAGCGGCAAATAT
CACAGATAATCAGGATCATGAACATTGGCAATAACGCGACGGTGATACAACCTGTTCTGCAAGATATTTCG
GTACTCCTTCAACGCATATCACCACTCCAAATAGATCCAACTATTATTTCCAACACTATGTCAACAGTCTC
GGAGTCTACTACTCAGACCCTCAGCCCCGCGTCCTCAATTTTGGGTAAACTACGACCAAGCAACTCAGATT
TTTCTAGTTTTAGAGTCGCGTTGGCTGGATGGCTTTATAATGGGGTTGTGACGACGGTGATTGATGATAGT
TCATATCCAAAAGACGGCGGCAGCGTGACCTCACTTGAAAATCTGTGGGATTTCTTCATCCTTGCGCTTGC
TCTACCACTGACAACTGACCCCTGTGCACCTGTGAAAGCATTCATGACCCTAGCCAACATGATGGTTGGTT
TCGAGACAATCCCTATGGATAATCAGATCTATACTCAATCGAGACGCGCGAGTGCTTTCTCAACGCCTCAC
ACGTGGCCACGATGCTTTATGAACATCCAGTTAATTTCTCCAATCGACGCTCCATCTTGCGACAGTGGGC
TGAAATTATTCATAGATACTGGCCTAACCCTTCACAGATTCGTTATGGTGCACCGAACGTTTTCGGCTCGG
CAAATTTGTTCACTCCACCTGAGGTGCTGTTATTGCCAATCGATCATCAACCAGCTAATGTAACAACGCCA
ACGCTGGACTTCACCAATGAGTTAACTAATTGGCGCGCTCGTGTCTGTGAGCTTATGAAGAATCTCGTTGA
TAACCAAAGATATCAACCTGGATGGACACAAAGTCTAGTCTCGTCAATGCGCGGAACGCTAGACAAATTGA
AGTTGATTAAATCGATGACACCAATGTATCTGCAACAGCTGGCTCCGGTAGAGTTAGCAGTGATAGCTCCC
ATGTTGCCTTTTCCACCTTTCCAGGTGCCATACGTCCGTCTCGATCGTGACAGAGTTCCAACAATGGTTGG
AGTAACACGACATTCACGAGATACTATTACTCAGCCGGCGCTATCGCTGTCGACAACCAATACTACTGTTG
GCGTGCCACTAGCTCTAGACGCGAGGGCTATCACCGTTGCGCTGTTGTCAGGGAAATATCCGCCGGATTTG
GTGACAAATGTATGGTACGCTGATGCCATTTACCCAATGTATGCAGACACGGAGGTGTTCTCTAATCTTCA
GAGAGACATGATTACCTGCGAGGCCGTGCAGACATTAGTGACTCTGGTGGCGCAAATATCAGAGACCCAGT
ATCCTGTAGATAGGTATCTTGATTGGATCCCATCACTGAGAGCATCGGCGGCGACGGCGGCGACATTTGCT

Figure 3D

```
GAGTGGGTTAATACTTCAATGAAGACGGCGTTTGATTTGTCTGATATGCTGTTAGAGCCTCTCCTAAGCGG
TGATCCGAGGATGACTCAACTAGCGATTCAGTATCAGCAGTACAATGGCAGAACGTTTAATATCATACCTG
AAATGCCAGGTTCAGTAATTGCTGACTGCGTTCAATTAACAGCAGAAGTCTTTAATCACGAATATAACCTG
TTTGGGATTGCGCGGGGTGATATCATCATTGGCCGTGTTCAGTCGACACATTTGTGGTCACCGCTGGCTCC
TCCACCTGACCTGGTGTTTGATCGTGATACCCCTGGTGTTCACATCTTCGGACGAGATTGCCGTATATCGT
TTGGAATGAATGGCGCCGCGCCAATGATTAGAGATGAGACTGGACTGATGGTGCCTTTTGAAGGAAATTGG
ATTTTCCCACTGGCGCTTTGGCAAATGAATACACGATATTTTAATCAACAGTTCGACGCGTGGATTAAGAC
AGGAGAGTTGCGAATCCGCATTGAGATGGGCGCGTATCCATATATGTTGCATTACTATGATCCACGTCAGT
ACGCTAATGCATGGAATTTAACATCCGCCTGGCTTGAAGAAATTACGCCGACGAGCATCCCATCCGTGCCT
TTCATGGTGCCCATTTCAAGTGATCATGACATTTCCTCTGCCCCAGCTGTCCAATATATCATTTCAACTGA
ATATAATGATCGGTCTCTGTTCTGCACTAACTCATCATCTCCCCAAACCATCGCTGGACCAGACAAACACA
TTCCAGTTGAGAGATATAACATTCTGACCAACCCCGACGCTCCACCCACGCAGATACAACTGCCTGAAGTC
GTTGACTTGTACAACGTCGTCACACGCTATGCGTATGAGACTCCGCCTATTACCGCTGTTGTTATGGGTGT
TCCTTGATCCTCATCCTCCCAACAGGTGCTAGAGCATTGCGCTCAATGCTAGTTGGGCCGATTCATC
(SEQ ID NO:10)
```

Figure 4

[1:
MDPRLREEVVRLIIALTSDNGASLSKGLESRVSALEKTSQIHSDTILRITQGLDDANKRIIALEQSRDDLV
ASVSDAQLAISRLESSIGALQTVVNGLDSSVTQLGARVGQLETGLAELRVDHDNLVARVDTAERNIGSLTT
ELSTLTLRVTSIQADFESRISTLERTAVTSAGAPLSIRNNRMTMGLNDGLTLSGNNLAIRLPGNTGLNIQN
GGLQFRFNTDQFQIVNNNLTLKTTVFDSINSRIGATEQSYVASAVTPLRLNSSTKVLDMLIDSSTLEINSS
GQLTVRSTSPNLRYPIADVSGGIGMSPNYRFRQSMWIGIVSYSGSGLNWRVQVNSDIFIVDDYIHICLPAF
DGFSIADGGDLSLNFVTGLLPPLLTGDTEPAFHNDVVTYGAQTVAIGLSSGGAPQYMSKNLWVEQWQDGVL
RLRVEGGGSITHSNSKWPAMTVSYPRSFT (SEQ ID NO:11)

[2:
MARAAFLFKTVGFGGLQNVPINDELSSHLLRAGNSPWQLTQFLDWISLGRGLATSALVPTAGSRYYQMSCL
LSGTLQIPFRPNHRWGDIRFLRLVWSAPTLDGLVVAPPQVLAQPALQAQADRVYDCDDYPFLARDPRFKHR
VYQQLSAVTLLNLTGFGPISYVRVDEDMWSGDVNQLLMNYFGHTFAEIAYTLCQASANRPWEYDGTYARMT
QIVLSLFWLSYVGVIHQQNTYRTFYFQCNRRGDAAEVWILSCSLNHSAQIRPGNRSLFVMPTSPDWNMDVN
LILSSTLTGCLCSGSQLPLIDNNSVPAVSRNIHGWTGRAGNQLHGFQVRRMVTEFCDRLRRDGVMTQAQQN
QVEALADQTQQFKRDKLETWAREDDQYNQAHPNSTMFRTKPFTNAQWGRGNTGATSAAIAALI (SEQ ID
NO:12)

[NS:
MASSLRAAISKIKRDDVGQQVCPNYVMLRSSVTTKVVRNVVEYQIRTGGFFSCLAMLRPLQYAKRERLLGQ
RNLERISTRDILQTRDLHSLCMPTPDAPMSNHQASTMRELICSYFKVDHADGLKYIPMDERYSPSSLARLF
TMGMAGLHITTEPSYKRVPIMHLAADLDCMTLALPYMITLDGDTVVPVAPTLSAEQLLDDGLKGLACMDMD
VRWTRIAGRLVIRVWTLHAASTSCIARRQQKPSVCLRHALC (SEQ ID NO:13)

MASSLRAAISKIKRDDVGQQVCPNYVMLRSSVTTKVVRNVVEYQIRTGGFFSCLAMLRPLQYAKRERLLGQ
RNLERISTRDILQTRDLHSLCMPTPDAPMSNHQASTMRELICSYFKVDHADGLKYIPMDERYSPSSLARLF
TMGMAGLHITTEPSYKRVPIMHLAADLDCMTLALPYMITLDGDTVVPVAPTLSAEQLLDDGLKGLACMDIS
YGCEVDANSRPAGDQSMDSSRCINELYCEETAEAICVLKTCLVLNCMQFKLEMDDLAHNAAELDKIQMMIP
FSERVFRMASSFATIDAQCFRFCVMMKDKNLKIDMRETTRLWTRSASDDSVATSSLSISLDRGRWVAADAS
DARLLVFPIRV (SEQ ID NO:14)

[3:
MEVCLPNGHQVVDLINNAFEGRVSIYSAQEGWDKTISAQPDMMVCGGAVVCMHCLGVVGSLQRKLKHLPHH
RCNQQIRHQDYVDVQFADRVTAHWKRGMLSFVAQMHEMMNDVSPDDLDRVRTEGGSLVELNRLQVDPNSMF
RSIHSSWTDPLQVVDDLDTKLDQYWTALNLMIDSSDLIPNFMMRDPSHAFNGVKLKGDARQTQFSRTFDSR
SSLEWGVMVYDYSELDHDPSKGRAYRKELVTPARDFGHFGLSHYSRATTPILGKMPAVFSGMLTGNCKMYP
FIKGTAKLKTVRKLVEAVNHAWGVEKIRYALGPGGMTGWYNRTMQQAPIVLTPAALTMFPDTIKFGDLNYP
VMIGDPMILG (SEQ ID NO:15)

Figure 5

μ2:
MAYIAVPAVVDSRSSEAIGLLESFGVDAGADANDVSYQDHDYVLDQLQYMLDGYEAGDVIDALVHKNWLHH
SVYCLLPPKSQLLEYWKSNPSAIPDNVDRRLRKRLMLKKDLRKDDEYNQLARAFKISDVYAPLISSTTSPM
TMIQNLNRGEIVYTTTDRVIGARILLYAPRKYYASTLSFTMTKCIIPFGKEVGRVPHSRFNVGTFPSIATP
KCFVMSGVDIESIPNEFIKLFYQRVKSVHANILNDISPQIVSDMINRKRLRVHTPSDRRAAQLMHLPYHVK
RGASHVDVYKVDVVDMLFEVVDVADGLRNVSRKLTMHTVPVCILEMLGIEIADYCIRQEDGMLTDWFLLLT
MLSDGLTDRRTHCQYLINPSSVPPDVILNISITGFINRHTIDVMPDIYDFVKPIGAVLPKGSFKSTIMRVL
DSISILGIQIMPRAHVVDSDEVGEQMEPTFEQAVMEIYKGIAGVDSLDDLIKWVLNSDLIPHDDRLGQLFQ
AFLPLAKDLLAPMARKFYDNSMSEGRLLTFSHADSELLNANYFGHLLRLKIPYITEVNLMIRKNREGGELF
QLVLSYLYKMYATSAQPKWFGSLLRLLICPWLHMEKLIGEADPASTSAEIGWHIPREQLMQDGWCGCEDGF
IPYVSIRAPRLVIEELMEKNWGQYHAQVIVTDQLVVGEPRRVSAKAVIKGNHLPVKLVSRFACFTLTAKYE
MRLSCGHSTGRGAAYSARLAFRSDLA (SEQ ID NO:16)

μ1:
MGNASSIVQTINVTGDGNVFKPSAETSSTAVPSLSLSPGMLNPGGVPWIAVGDETSVTSPGALRRMTSKDI
PDTAIINTDNSSGAVPSESALVPYIDEPLVVVTEHAITNFTKAEMALEFNREFLDKMRVLSVSPKYSDLLT
YVDCYVGVSARQALNNFQKQVPVITPTRQTMYVDSIQAALKALEKWEIDLRVAQTLLPTNVPIGEVSCPMQ
SVVKLLDDQLPDDSLIRRYPKEAAVALAKRNGGIQWMDVSEGTVMNEAVNAVAASALAPSASAPPLEEKSK
LTEQAMDLVTAAEPEIIASLAPVPAPVFAIPPKPADYNVRTLRIDEATWLRMIPKSMNTPFQIQVTDNTGT
NWHLNLRGGTRVVNLDQIAPMRFVLDLGGKSYKETSWDPNGKKVGFIVFQSKIPFELWTAASQIGQATVVN
YVQLYAEDSSFTAQSIIATTSLAYNYEPEQLNKTDPEMNYYLLATFIDSAAITPTNMTQPDVWDALLTMSP
LSAGEVTVKGAVVSEVVPADLIGSYTPESLNASLPNDAARCMIDRASKIAEAIKIDDDAGPDEYSPNSVPI
QGQLAISQLETGYGVRIFNPKGILSKIASRAMQAFIGDPSTIITQAAPVLSDKNNWIALAQGVKTSLRTKS
LSAGVKTAVSKLSSSESIQNWTQGFLDKVSAHFPAPKPDCPTSGDSGESSNRRVKRDSYAGVVKRGYTR
(SEQ ID NO:17)

μNS:
MASFKGFSANTVPVSKAKRDISSLAATPGLRSQSFTPSVDMSQSREFLTKAIEQGSMSIPYQHVNVPKVDR
KVVSLVVRPFSSGAFSISGVISPAHAYLLECLPQLEQAMAFVASPESFQASDVAKRFAIKPGMSLQDAITA
FINFVSAMLKMTVTRQNFDVIVAEIERLASTSVSVRTEEAKVADEELMLFGLDHRGPQQLDVSDAKGIMKA
ADIQTTHDVHLAPGVGNIDPEIYNEGRFMFMQHKPLAADQSYFTLETADYFKIYPTYDEHDGRMADQKQSG
LILCTKDEVLAEQTIFKLDAPDDKTVHLLDRDDDHVVARFTKVFIEDVAPGHHAAQRSGQRSVLDDLYANT
QVISITSAALKWVVKHGVSDGIVNRKNVKVCVGFDPLYTLSTHNGVSLCALLMDEKLSVLNSACRMTLRSL
MKTGRDVDAHRAFQRVLSQGYTSLMCYYHPSRKLAYGEVLFLERSNDVTDGIKLQLDASRQCHECPVLQQK
VVELEKQIIMQKSIQSDPTPVALQPLLSQLRELSSEVTRLQMELSRAQSLNAQLEADVKSAQSCSLDMYLR
HHTCINGHAKEDELLDAVRVAPDVRREIMEKRSEVRQGWCERISKEAAAKCQTVIDDLTLMNGKQAQEITE
LRDSAEKYEKQIAELVSTITQNQITYQQELQALVAKNVELDALNQRQAKSLRITPSLLSATPIDSVDDVAD
LIDFSVPTDEL (SEQ ID NO:18)

Figure 6A

λ3:
MSSMILTQFGPFIESISGITDQSNDVFEDAAKAFSMFTRSDVYKALDEIPFSDDAMLPIPPTIYTKPSHDS
YYYIDALNRVRRKTYQGPDDVYVPNCSIVELLEPHETLTSYGRLSEAIENRAKDGDSQARIATTYGRIAES
QARQIKAPLEKFVLALLVAEAGGSLYDPVLQKYDEIPDLSHNCPLWCFREICRHISGPLPDRAPYLYLSAG
VFWLMSPRMTSAIPPLLSDLVNLAILQQTAGLDPSLVKLGVQICLHAAASSSYAWFILKTKSIFPQNTLHS
MYESLEGGYCPNLEWLEPRSDYKFMYMGVMPLSAKYARSAPSNDKKARELGEKYGLSSVVGELRKRTKTYV
KHDFASVRYIRDAMACTSGIFLVRTPTETVLQEYTQSPEIKVPIPQKDWTGPIGEIRILKDTTSSIARYLY
RTWYLAAARMAAQPRTWDPLFQAIMRSQYVTARGGSGAALRESLYAINVSLPDFKGLPVKAATKIFQAAQL
ANLPFSHTSVAILADTSMGLRNQVQRRPRSIMPLNVPQQQVSAPHTLTADYINYHMNLSTTSGSAVIEKVI
PLGVYASSPPNQSINIDISACDASITWDFFLSVIMAAIHEGVASSSIGKPFMGVPASIVNDESVVGVRAAR
PISGMQNMIQHLSKLYKRGFSYRVNDSFSPGNDFTHMTTTFPSGSTATSTEHTANNSTMMETFLTVWGPEH
TDDPDVLRLMKSLTIQRNYVCQGDDGLMIIDGTTAGKVNSETIQKMLELISKYGEEFGWKYDIAYDGTAEY
LKLYFIFGCRIPNLSRHPIVGKERANSSAEEPWPAILDQIMGVFFNGVHDGLQWQRWIRYSWALCCAFSRQ
RTMIGESVGYLQYPMWSFVYWGLPLVKAFGSDPWIFSWYMPTGDLGMYSWISLIRPLMTRWMVANGYVTDR
CSPVFGNADYRRCFNELKLYQGYYMAQLPRNPKKSGRAAPREVREQFTQALSDYLLQNPELKSRVLRGRSE
WEKYGAGIIHNPPSLFDVPHKWYQGAQEAAIATREELAEMDETLMRARRHRYSSFSKLLEAYLLVKWRMCE
AREPSVDLRLPLCAGIDPLNSDPFLKMVSVGPMLQSTRKYFAQTLFMAKTVSGLDVNAIDSALLRLRTLGA
DKKALTAQLLMVGLQESEADALAGKIMLQDVNTVQLARVVNLAVPDTWMSLDFDSMFKHHVKLLPKDGRHL
NTDIPPRMGWLRAILRFLGAGMVMTATGVAVDIYLEDIHGGGRSLGQRFMTWMRQEGRSA (SEQ ID
NO:19)

λ2:
MANVWGVRLADSLSSPTIETRTRQYTLHDLCSDLDANPGREPWKPLRNQRTNNIVAVQLFRPLQGLVLDTQ
LYGFPGAFDDWERFMREKLRVLKYEVLRIYPISNYSNEHVNVFVANALVGAFLSNQAFYDLLPLLIINDTM
IGDLLGTGASLSQFFQSHGDVLEVAAGRKYLQMENYSNDDDDPPLFAKDLSDYAKAFYSDTYEVLDRFFWT
HDSSAGVLVHYDKPTNGHHYLLGTLTQMVSAPPYIINATDAMLLESCLEQFSANVRARPAQPVTRLDQCYH
LRWGAQYVGEDSLTYRLGVLSLLATNGYQLARPIPRQLTNRWLSSFVSQIMSDGVNETPLWPQERYVQIAY
DSPSVVDGATQYGYVRKNQLRLGMRISALQSLSDTPSPVQWLPQYTIDQAAMDEGDLMVSRLTQLPLRPDY
GNIWVGDALSYYVDYNRSHRVVLSSELPQLPDTYFDGDEQYGRSLFSLARKIGDRSLVKDTAVLKHAYQAI
DPNTGKEYLRSRQSVAYFGASAGHSGADQPLVIEPWIQGKISGVPPPSSVRQFGYDVARGAIVDLARPFPS
GDYQFVYSDVDQVVDGHDDLSISSGLVESLLSSCMHATAPGGSFVVKINFPTRPVWHYIEQKILPNITSYM
LIKPFVTNNVELFFVAFGVHQHSSLTWTSGVYFFLVDHFYRYETLSTISRQLPSFGYVDDGSSVTGIETIS
IENPGFSNMTQAARIGISGLCANVGNARKSIAIYESHGARVLTITSRRSPASARRKSRLRYLPLIDPRSLE
VQARTILPADPVLFENVSGASPHVCLTMMYNFEVSSAVYDGDVVLDLGTGPEAKILELIPATSPVTCVDIR
PTAQPSGCWNVRTTFLELDYLSDGWITGVRGDIVTCMLSLGAAAAGKSMTFDAAFQQLIKVLSKSTANVVL
VQVNCPTDVVRSIKGYLEIDSTNKRYRFPKFGRDEPYSDMDALEKICRTAWPNCSITWVPLSYDLRWTRLA
LLESTTLSSASIRIAELMYKYMPIMRIDIHGLPMEKRGNFIVGQNCSLVIPGFNAQDVFNCYFNSALAFST
EDVNAAMIPQVSAQFDATKGEWTLDMVFSDAGIYTMQALVGSNANPVSLGSFVVDSPDVDITDAWPAQLDF
TIAGTDVDITVNPYYRLMTFVRIDGQWQIANPDKFQFFSSASGTLVMNVKLDIADKYLLYYIRDVQSRDVG
FYIQHPLQLLNTITLPTNEDLFLSAPDMREWAVKESGNTICILNSQGFVLPQDWDVLTDTISWSPSIPTYI
VPPGDYTLTPL (SEQ ID NO:20)

λ1:
MKRIPRKTKGKSSGKGNDSTERADDGSSQLRDKQNNKAGPATTEPGTSNREQYKARPGIASVQRATESAEM
PMKNNDEGTPDKKGNTKGDLVNEHSEAKDEADEATKKQAKDTDKSKAQVTYSDTGINNANELSRSGNVDNE
GGSNQKPMSTRIAEATSAIVSKHPARVGLPPTASSGHGYQCHVCSAVLFSPLDLDAHVASHGLHGNMTLTS
SDIQRHITEFISSWQNHPIVQVSADVENKKTAQLLHADTPRLVTWDAGLCTSFKIVPIVPAQVPQDVLAYT
FFTSSYAIQSPFPEAAVSRIVVHTRWASNVDFDRDSSVIMAPPTENNIHLFKQLLNTETLSVRGANPLMFR
ANVLHMLLEFVLDNLYLNRHTGFSQDHTPFTEGANLRSLPGPDAEKWYSIMYPTRMGTPNVSKICNFVASC
VRNRVGRFDRAQMMNGAMSEWVDVFETSDALTVSIRGRWMARLARMNINPTEIEWALTECAQGYVTVTSPY
APSVNRLMPYRISNAERQISQIIRIMNIGNNATVIQPVLQDISVLLQRISPLQIDPTIISNTMSTVSESTT
QTLSPASSILGKLRPSNSDFSSFRVALAGWLYNGVVTTVIDDSSYPKDGGSVTSLENLWDFFILALALPLT

Figure 6B

```
TDPCAPVKAFMTLANMMVGFETIPMDNQIYTQSRRASAFSTPHTWPRCFMNIQLISPIDAPILRQWAEIIH
RYWPNPSQIRYGAPNVFGSANLFTPPEVLLLPIDHQPANVTTPTLDFTNELTNWRARVCELMKNLVDNQRY
QPGWTQSLVSSMRGTLDKLKLIKSMTPMYLQQLAPVELAVIAPMLPFPPFQVPYVRLDRDRVPTMVGVTRH
SRDTITQPALSLSTTNTTVGVPLALDARAITVALLSGKYPPDLVTNVWYADAIYPMYADTEVFSNLQRDMI
TCEAVQTLVTLVAQISETQYPVDRYLDWIPSLRASAATAATFAEWVNTSMKTAFDLSDMLLEPLLSGDPRM
TQLAIQYQQYNGRTFNIIPEMPGSVIADCVQLTAEVFNHEYNLFGIARGDIIIGRVQSTHLWSPLAPPPDL
VFDRDTPGVHIFGRDCRISFGMNGAAPMIRDETGLMVPFEGNWIFPLALWQMNTRYFNQQFDAWIKTGELR
IRIEMGAYPYMLHYYDPRQYANAWNLTSAWLEEITPTSIPSVPFMVPISSDHDISSAPAVQYIISTEYNDR
SLFCTNSSSPQTIAGPDKHIPVERYNILTNPDAPPTQIQLPEVVDLYNVVTRYAYETPPITAVVMGVP
(SEQ ID NO:21)
```

REOVIRUSES HAVING MODIFIED SEQUENCES

CROSS-REFERENCE TO RELATED APPLICATIONS

This application is a continuation of U.S. Ser. No. 16/027,206, filed Jul. 3, 2018, which is a continuation of U.S. Ser. No. 14/179,840, filed Feb. 13, 2014, now U.S. Pat. No. 10,039,827, which is a continuation of U.S. Ser. No. 12/848,684, filed Aug. 2, 2010, now U.S. Pat. No. 8,691,241, which is a divisional of U.S. Ser. No. 12/046,095, filed Mar. 11, 2008, now U.S. Pat. No. 7,803,385, which claims priority under 35 U.S.C. 119(e) to U.S. Application No. 60/894,425 filed on Mar. 12, 2007 and U.S. Application No. 60/989,568 filed on Nov. 21, 2007. Each of these applications is incorporated herein by reference in their entireties.

TECHNICAL FIELD

This invention relates to viruses, and more particularly to reoviruses having modified sequences.

BACKGROUND

The name reovirus derives from an acronym for respiratory and enteric orphan virus, reflecting that the initial isolates came from human respiratory and enteric tracts but were not associated with serious disease. Reoviruses have a double-stranded, segmented RNA genome. The virions measure 60-80 nm in diameter and possess two concentric capsid shells, each of which is icosahedral. The mammalian reovirus genome consists of double-stranded RNA in 10 discrete segments with a total genome size of ~23.5 kbp. The individual RNA segments vary in size.

Three serologically distinct but related types of reovirus have been recovered from mammalian species: type 1 (representative strains include, for example, Lang (T1L)), type 2 (representative strains include, for example, Jones (T2J)) and type 3 (representative strains include, for example, Dearing or Abney (T3D or T3A, respectively)). The three serotypes are easily identifiable on the basis of neutralization and hemagglutinin-inhibition assays (see, for example, Sabin, 1959, *Science,* 130:966; Fields, et al., 1996, *Fundamental Virology,* 3rd Ed., Lippincott-Raven; Rosen, 1960, *Am. J. Hyg.,* 71:242; and Stanley, 1967, *Br. Med. Bull.,* 23:150).

SUMMARY

Provided herein are reoviruses having modified nucleic acid and polypeptide sequences. Sequence modifications include, for example, modifications in one or more of the reovirus genome segments. Also provided are pharmaceutical compositions that include reoviruses having a modified sequence as well as methods of using such reoviruses.

In one aspect, the invention provides a reovirus that has a lambda-3 polypeptide having one or more amino acid modifications; a sigma-3 polypeptide having one or more amino acid modifications; a mu-1 polypeptide having one or more amino acid modifications; and/or a mu-2 polypeptide having one or more amino acid modifications. Such a reovirus can be, for example, non-naturally occurring. In another aspect, the invention provides a reovirus lambda-3 polypeptide having one or more amino acid modifications; a reovirus sigma-3 polypeptide having one or more amino acid modifications; a reovirus mu-1 polypeptide having one or more amino acid modifications; and/or a reovirus mu-2 polypeptide having one or more amino acid modifications.

By way of example, the one or more amino acid modifications in the lambda-3 polypeptide can be a Val at residue 214, an Ala at residue 267, a Thr at residue 557, a Lys at residue 755, a Met at residue 756, a Pro at residue 926, a Pro at residue 963, a Leu at residue 979, an Arg at residue 1045, a Val at residue 1071, or any combination thereof, numbered relative to GenBank Accession No. M24734.1. It is noted that, when the amino acid sequence is a Val at residue 214 or a Val at residue 1071, the amino acid sequence further includes at least one additional change in the amino acid sequence. In one embodiment, the lambda-3 polypeptide includes the sequence shown in SEQ ID NO:19.

Further by way of example, the one or more amino acid modifications in the sigma-3 polypeptide can be a Leu at residue 14, a Lys at residue 198, or any combination thereof, numbered relative to GenBank Accession No. K02739. It is noted that, when the amino acid sequence is a Leu at residue 14, the amino acid sequence further includes at least one additional change in the amino acid sequence. In one embodiment, the sigma-3 polypeptide includes the sequence shown in SEQ ID NO:15.

Further by way of example, the one or more amino acid modifications in the mu-1 polypeptide can be an Asp at residue 73 numbered relative to GenBank Accession No. M20161.1. In one embodiment, the mu-1 polypeptide includes the sequence shown in SEQ ID NO:17.

Also by way of example, the amino acid modification mu-2 polypeptide can be a Ser at residue 528 numbered relative to GenBank Accession No. AF461684.1. In one embodiment, the mu-2 polypeptide includes the sequence shown in SEQ ID NO:16.

A reovirus as described herein having one or more modifications can further include a reovirus sigma-2 polypeptide. Such a sigma-2 polypeptide can have a Cys at one or more of position 70, 127, 195, 241, 255, 294, 296, or 340, numbered relative to GenBank Accession No. NP_694684.1. In one embodiment, the sigma-2 polypeptide includes the sequence shown in SEQ ID NO:12.

In another aspect, the invention provides a reovirus that has a L1 genome segment having one or more nucleic acid modifications; a S4 genome segment having one or more nucleic acid modifications; a M1 genome segment having one or more nucleic acid modifications; and/or a M2 genome segment having one or more nucleic acid modifications. Such a reovirus can be, for example, non-naturally occurring. In another aspect, the invention provides a L1 genome segment having one or more nucleic acid modifications; a S4 genome segment having one or more nucleic acid modifications; a M1 genome segment having one or more nucleic acid modifications; and/or a M2 genome segment having one or more nucleic acid modifications.

By way of example, the one or more nucleic acid modifications in the L1 genome segment can be a T at position 660, a G at position 817, an A at position 1687, a G at position 2283, an ATG at positions 2284-2286, a C at position 2794, a C at position 2905, a C at position 2953, an A at position 3153, or a G at position 3231, numbered relative to GenBank Accession No. M24734.1. In one embodiment, the L1 genome segment includes the sequence shown in SEQ ID NO:8.

Further by way of example, the one or more nucleic acid modifications in the S4 genome segment can be an A at position 74 and an A at position 624, numbered relative to GenBank Accession No. K02739. In one embodiment, the S4 genome segment includes the sequence shown in SEQ ID NO:4.

Further by way of example, the nucleic acid modification in the M2 genome segment can be a C at position 248, numbered relative to GenBank Accession No. M20161.1. In one embodiment, the M2 genome segment includes the sequence shown in SEQ ID NO:6.

Also by way of example, the nucleic acid modification in the M1 genome segment can be a T at position 1595, numbered relative to GenBank Accession No. AF461684.1. In one embodiment, the M1 genome segment includes the sequence shown in SEQ ID NO:5.

A reovirus as described herein can include any modification or combination of modifications disclosed herein. In some embodiments, a reovirus as described herein is a reassortant. In certain embodiments, a reovirus as described herein includes genomic segments having the sequences shown in SEQ ID NOs:1-10 or the polypeptides shown in SEQ ID NOs:11, 12, and 16-21, and either or both SEQ ID NO:13 or 14. In one embodiment, a reovirus as disclosed herein is identified as IDAC Accession No. 190907-01.

A reovirus as disclosed herein generally exhibits a growth advantage over a reovirus that does not contain a corresponding modification. Representative growth advantages include, but are not limited to, an increased rate of lysis; an increased size of plaque formation; an increased rate of RNA replication; an increased rate of RNA transcription; an increased rate of translation; an increased rate of virus assembly and/or packaging; an increased number of viral progeny; an increased ability of a reovirus to be taken up by a host cell; an increased or enhanced ability to uncoat; enhanced cell lysis or inducement to cell death including apoptosis, necrosis or autophagy; an enhanced ability to infect, lyse and kill human neoplastic cells lines; decreased immunogenicity in mammalian cells; differential susceptibility to interferon sensitivity; decreased toxicity toward the host; enhanced drug interaction; enhanced radiotherapy interaction; or the ability to release effective tumor epitopes.

A reovirus as described herein can be included, along with a pharmaceutically acceptable carrier, in a pharmaceutical composition. Such pharmaceutical compositions can include, for example, one or more chemotherapeutic agents and/or one or more immunosuppressive agents.

In still another aspect, the invention provides for methods of making an improved reovirus. Such methods generally include the steps of modifying the nucleic acid sequence of the reovirus, and selecting one or more improved reoviruses. In some embodiments, the modifying step includes, for example, mutagenizing the reovirus. Representative types of mutagenesis include, without limitation, site-directed mutagenesis and chemical mutagenesis. In other embodiments, the modifying step includes culturing the reovirus in a human cell line.

An improved reovirus made according to the methods disclosed herein can be selected for an increased rate of lysis; an increased size of plaque formation; an increased rate of RNA replication; an increased rate of RNA transcription; an increased rate of translation; an increased rate of virus assembly and/or packaging; an increased number of viral progeny; an increased ability of a reovirus to be taken up by a host cell; an increased or enhanced ability to uncoat; enhanced cell lysis or inducement to cell death including apoptosis, necrosis or autophagy; an enhanced ability to infect, lyse and kill human neoplastic cells lines; decreased immunogenicity in mammalian cells; differential susceptibility to interferon sensitivity; decreased toxicity toward the host; enhanced drug interaction; enhanced radiotherapy interaction; or the ability to release effective tumor epitopes.

In yet another aspect, the invention provides methods of treating a proliferative disorder in a patient. Such methods generally include administering a modified reovirus as described herein or a pharmaceutical composition containing such a modified reovirus to the patient. Typically, the reovirus is administered in an amount effective to cause oncolysis, and can be administered more than once. Representative routes of administration include, for example, direct injection, intravenously, intravascularly, intrathecally, intramuscularly, subcutaneously, intraperitoneally, topically, orally, rectally, vaginally, nasally, or by inhalation. The methods of treating a proliferative disorder as described herein can be accompanied by one of more procedures such as surgery, chemotherapy, radiation therapy, and immunosuppressive therapy.

In another aspect, the invention provides a kit (or article of manufacture) that includes a reovirus having a modified sequence or any combination of genome segments having a modified sequence as disclosed herein. A kit also can include one or more agents as disclosed herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

FIGS. 1A and 1B are the nucleotide sequence of a representative S1 segment (SEQ ID NO:1), S2 segment (SEQ ID NO:2), S3 segment (SEQ ID NO:3) and S4 segment (SEQ ID NO:4).

FIGS. 2A and 2B are the nucleotide sequence of a representative M1 segment (SEQ ID NO:5), M2 segment (SEQ ID NO:6) and M3 segment (SEQ ID NO:7).

FIGS. 3A, 3B, 3C and 3D are the nucleotide sequence of a representative L1 segment (SEQ ID NO:8), L2 segment (SEQ ID NO:9) and L3 segment (SEQ ID NO:10).

FIG. 4 is the amino acid sequence of a representative sigma-1 polypeptide (SEQ ID NO:11), sigma-2 polypeptide (SEQ ID NO:12), sigma-NS polypeptide (putative coding sequence 1, SEQ ID NO:13; putative coding sequence 2, SEQ ID NO:14) and sigma-3 polypeptide (SEQ ID NO:15).

FIG. 5 is the amino acid sequence of a representative mu-2 polypeptide (SEQ ID NO:16), mu-1 polypeptide (SEQ ID NO:17) and mu-NS polypeptide (SEQ ID NO:18).

FIGS. 6A and 6B are the amino acid sequence of a representative lambda-3 polypeptide (SEQ ID NO:19), lambda-2 polypeptide (SEQ ID NO:20) and lambda-1 polypeptide (SEQ ID NO:21).

Like reference symbols in the various drawings indicate like elements.

DETAILED DESCRIPTION

This disclosure describes modifications in the nucleotide and amino acid sequence of a reovirus. Such modifications are optionally selected to affect the virus's ability to replicate and/or package itself and, therefore, alter the infectivity and/or rate of replication of a reovirus.

Reovirus Having Modified Sequences and Methods of Making

Any of the genomic segments from any type 3 mammalian orthoreovirus (referred to herein simply as "reovirus") can be modified as disclosed herein. Representative type 3 mammalian orthoreoviruses include, without limitation, Dearing and Abney strains. See, for example, ATCC Accession Nos. VR-232 and VR-824. Reoviruses that can be modified as disclosed herein include naturally-occurring reoviruses (e.g., isolated from a source in nature such as from a patient) and reassortant reoviruses (see, e.g., U.S. Pat. No. 7,163,678).

Representative modifications to the different genomic segments of a reovirus and their manifestations in the encoded polypeptide are shown in Table 1. The modifications shown in Table 1 show modifications (both in the number of modifications and in the non-conservative nature of many of the modifications) in the sequence of segments encoding polypeptides associated with RNA-dependent RNA polymerase, transcriptional activities and/or RNA binding. For example, many of the novel modifications disclosed herein are located in the L1 genome segment. The wild-type L1 genome segment encodes a 1,267 amino acid (142 kDa) protein designated lambda-3. Lambda-3 represents the catalytic subunit of the reovirus RNA-dependent RNA polymerase, which mediates both plus- and minus-strand RNA synthesis within reovirus particles. Further modifications were observed in the M2 genome segment. The wild-type M2 genome segment encodes a 708 amino acid (76 kDa) protein designated mu-1, which is involved in the regulation of particle-bound transcription. In addition, modifications also were observed in the S4 and M1 genomic segments, which encode sigma-3 and mu-2, respectively, and play a role in transcription or single-stranded or double-stranded RNA binding.

Thus, this disclosure provides for L1, S4, M1, M2 or any combination of such genome segments that contain one or more nucleic acid modifications in the respective genome segment. Provided herein is a reovirus L1 genome segment having one or more nucleic acid modifications; a reovirus S4 genome segment having one or more nucleic acid modifications; a reovirus M1 genome segment having one or more nucleic acid modifications; and/or a M2 genome segment having one or more nucleic acid modifications.

A reovirus L1 genome segment has, for example, any combination of one or more of the following nucleotides: a T at position 660, a G at position 817, an A at position 1687, a G at position 2283, an ATG at positions 2284-2286, a C at position 2794, a C at position 2905, a C at position 2953, an A at position 3153, or a G at position 3231 (numbered relative to SEQ ID NO:22 (GenBank Accession No. M24734.1)). A reovirus S4 genome segment has, for example, any combination of one or more of the following nucleotides: an A at position 74 or an A at position 624 (numbered relative to SEQ ID NO:24 (GenBank Accession No. K02739)). A reovirus M1 genome segment has, for example, a T nucleotide at position 1595 (numbered relative to SEQ ID NO:28 (GenBank Accession No. AF461684.1)). A reovirus M2 genome segment has, for example, a C nucleotide at position 248 (numbered relative to SEQ ID NO:26 (GenBank Accession No. M20161.1)). The indicated nucleotide at the indicated position represents modifications when compared to other corresponding sequences available in public databases (e.g., GenBank Accession Nos. M24734.1, K02739, AF461684.1, and M20161.1).

A reovirus lambda-3 polypeptide has, for example, any combination of one or more amino acid residues: a Val at residue 214, an Ala at residue 267, a Thr at residue 557, a Lys at residue 755, a Met at residue 756, a Pro at residue 926, a Pro at residue 963, a Leu at residue 979, an Arg at residue 1045, or a Val at residue 1071 (numbered relative to SEQ ID NO:23 (GenBank Accession No. M24734.1)). It is noted that, when the polypeptide sequence comprises a Val at residue 214 or a Val at residue 1071, the polypeptide sequence further comprises at least one additional change in the amino acid sequence. A reovirus sigma-3 polypeptide has, for example, any combination of one or more amino acid residues: a Leu at residue 14 or a Lys at residue 198 (numbered relative to SEQ ID NO:25 (GenBank Accession No. K02739)). It is noted that, when the polypeptide sequence comprises a Leu at residue 14, the polypeptide sequence further comprises at least one additional change in the amino acid sequence. A reovirus mu-1 polypeptide has, for example, an Asp at residue 73 (numbered relative to SEQ ID NO:29 (GenBank Accession No. AF461684.1)). A reovirus mu-2 polypeptide has, for example, a Ser at residue 528 (numbered relative to SEQ ID NO:27 (GenBank Accession No. M20161.1)). The indicated amino acid at the indicated position represents modifications when compared to other corresponding sequences in public databases (e.g., GenBank Accession Nos. M24734.1, K02739, AF461684.1, and M20161.1).

As used herein, a "non-naturally occurring" reovirus is a reovirus that has at least one nucleic acid or amino acid modification as compared to wild type sequences derived from, for example, a field isolate (e.g., a patient). "Non-naturally occurring" reovirus refers to a virus which has been manipulated or modified in the laboratory. Such manipulated or modified reoviruses include laboratory strains or mutagenized versions. These versions are distinguishable, in nucleic acid and/or amino acid sequence, from, for example, Dearing and Abney strains (e.g., ATCC VR-824 and VF-232, respectively). Representative modifications to one or more of the genome segments, the encoded polypeptide, or both are disclosed herein. In addition to a genome segment or polypeptide containing one or more of the modifications described herein, a reovirus optionally contains an S2 genome segment, which encodes the sigma-2 polypeptide. A sigma-2 polypeptide, for example, has a Cys at one or more or all of the following positions: 70, 127, 195, 241, 255, 294, 296 or 340 (numbered relative to SEQ ID NO:30 (GenBank Accession No. NP_694684.1)).

A modification generally occurs at the nucleic acid level, which may or may not manifest itself in the encoded polypeptide. Modifications to a nucleic acid include, without limitation, single or multiple nucleotide transitions (purine to purine or pyrimidine to pyrimidine) or transversions (purine to pyrimidine or vice versa) and single- or multiple-nucleotide deletions or insertions. A modification in a nucleic acid can result in one or more conservative or non-conservative amino acid substitutions in the encoded polypeptide, a shift in the reading frame of translation ("frame-shift) resulting in an entirely different polypeptide encoded from that point on, a premature stop codon resulting in a truncated polypeptide ("truncation"), or a modification in a reovirus nucleic acid may not change the encoded polypeptide at all ("silent" or "nonsense"). See, for example, Johnson & Overington, 1993, *J. Mol. Biol.*, 233:716-38; Henikoff & Henikoff, 1992, *Proc. Natl. Acad. Sci. USA*, 89:10915-19; and U.S. Pat. No. 4,554,101 for disclosure on conservative and non-conservative amino acid substitutions.

Nucleic acids from reovirus particles are isolated, for example, using standard methodologies, which are commercially available. See also, for example, Schiff et al., "Orthoreoviruses and Their Replication," Ch 52, in *Fields Virology*, Knipe & Howley, eds., 2006, Lippincott Williams & Wilkins. As used herein, "isolated" nucleic acids refer to nucleic acids that are substantially separated from other nucleic acids with which they are usually associated. Thus, an "isolated" nucleic acid includes, without limitation, reoviral nucleic acid that is essentially free of non-reoviral (e.g., host cell) nucleic acid, or a reoviral genomic segment that is essentially free of nucleic acid corresponding to other genomic segments. In addition, an isolated nucleic acid includes an engineered nucleic acid such as recombinant or synthetic nucleic acids.

Modifications are generated in the nucleic acid of a reovirus using any number of methods known in the art. For example, site directed mutagenesis can be used to modify a reovirus nucleic acid sequence. One of the most common methods of site-directed mutagenesis is oligonucleotide-directed mutagenesis. In oligonucleotide-directed mutagenesis, an oligonucleotide encoding the desired change(s) in sequence is annealed to one strand of the DNA of interest and serves as a primer for initiation of DNA synthesis. In this manner, the oligonucleotide containing the sequence change is incorporated into the newly synthesized strand. See, for example, Kunkel, 1985, *Proc. Natl. Acad. Sci. USA*, 82:488; Kunkel et al., 1987, *Meth. Enzymol.*, 154:367; Lewis & Thompson, 1990, *Nucl. Acids Res.*, 18:3439; Bohnsack, 1996, *Meth. Mol. Biol.*, 57:1; Deng & Nickoloff, 1992, *Anal. Biochem.*, 200:81; and Shimada, 1996, *Meth. Mol. Biol.*, 57:157.

Other methods are routinely used in the art to introduce a modification into a sequence. For example, modified nucleic acids are generated using PCR or chemical synthesis, or polypeptides having the desired change in amino acid sequence can be chemically synthesized. See, for example, Bang & Kent, 2005, *Proc. Natl. Acad. Sci. USA*, 102:5014-9 and references therein. Selection on a cell type on which reovirus is not usually grown (e.g., human cells) and/or chemical mutagenesis (see, for example, Rudd & Lemay, 2005, *J. Gen. Virology*, 86:1489-97) also can be used to generate modifications in the nucleic acid of a reovirus. For example, the modifications shown in Table 1 were generated by culturing reovirus on human cells (e.g., human embryonic kidney (HEK) 293 cells), which are not typically used in the art of culturing reovirus. In contrast, cells that are commonly used to culture reovirus are described in, for example, Tyler, "Mammalian Reoviruses," Ch 53, page 1731-2, in *Fields Virology*, Knipe & Howley, eds., 2006, Lippincott Williams & Wilkins. The modifications described herein represent an adaptation by the reovirus to human cells. There was also a selection step at each of these plaque purification steps by selection the largest plaque (triple plaque purification), thus a growth or virulence advantage in these cells.

After one or more modifications have been introduced into a reovirus nucleic acid or polypeptide, virus particles are reconstituted using methods known in the art. See, for example, Schiff et al., "Orthoreoviruses and Their Replication," Ch 52, in *Fields Virology*, Knipe & Howley, eds., 2006, Lippincott Williams & Wilkins; Smith et al., 1969, Virology, 39(4):791-810; and U.S. Pat. Nos. 7,186,542; 7,049,127; 6,808,916; and 6,528,305. Reoviruses having one or more modifications in their sequence are cultured in, for example, mouse L929 cells or neoplastic cells (e.g., MCF7 (ATCC Accession No. HTB-22), SKBR3 (ATCC Accession No. HTB-30), or MDA MB 468 (ATCC Accession No. HTB 132) cells), and selected based on any number of characteristics that may indicate, for example, a growth advantage over a reovirus that does not contain one or more modifications. Reoviruses are selected following culturing in a cell line (neoplastic or otherwise) and/or following infection of an animal model system.

Such characteristics include, without limitation, an increased rate of lysis; an increased size of plaque formation; an increased rate of RNA replication; an increased rate of RNA transcription; an increased rate of translation; an increased rate of virus assembly and/or packaging; an increased number of viral progeny; an increased ability of a reovirus to be taken up by a host cell; an increased or enhanced ability to uncoat; enhanced cell lysis or inducement to cell death including apoptosis, necrosis or autophagy; an enhanced ability to infect, lyse and kill human neoplastic cells lines; decreased immunogenicity in mammalian cells; differential susceptibility to interferon sensitivity; decreased toxicity toward the host; enhanced drug interaction; enhanced radiotherapy interaction; or the ability to release effective tumor epitopes. Additionally, reoviruses having a modified sequence are selected, for example, for the ability to lytically infect a mammalian cell having an active Ras pathway. See, for example, U.S. Pat. No. 7,052,832.

Reovirus particles are obtained using any number of methods known in the art. For example, reoviruses are cultured in L929 mouse fibroblast cells or human cells (e.g., HEK 293), and the viral particles purified using standard methodology. See, for example, Schiff et al., "Orthoreoviruses and Their Replication," Ch 52, in *Fields Virology*, Knipe & Howley, eds., 2006, Lippincott Williams & Wilkins; Smith et al., 1969, Virology, 39(4):791-810; and U.S. Pat. Nos. 7,186,542; 7,049,127; 6,808,916; and 6,528, 305. As used herein, "purified" viral particles refers to virus particles that have been substantially separated from cellular components that naturally accompany it. Typically, virus particles are considered "purified" when they are at least 70% (e.g., at least 75%, 80%, 85%, 90%, 95%, or 99%) by dry weight, free from the proteins and other cellular components with which the viruses are naturally associated.

A reovirus having the nucleic acid sequence shown in FIGS. 1, 2 and 3 (SEQ ID NOs: 1-10) and the amino acid sequence shown in FIGS. 4, 5, and 6 (SEQ ID NOs:11-20), which contain the nucleotide and amino acid modifications shown in Table 1, was deposited with the International Depositary Authority of Canada (IDAC, National Microbiology Laboratory, Public Health Agency of Canada, 1015 Arlington St., Winnipeg, Manitoba Canada R3E 3R2) on Sep. 19, 2007, and assigned Accession No. 190907-01. This deposit will be maintained under the terms of the Budapest Treaty on the International Recognition of the Deposit of Microorganisms for the Purposes of Patent Procedure. This deposit is exemplary and was made merely as a convenience for those of skill in the art and is not an admission that a deposit is required for patentability (e.g., under 35 U.S.C. § 112).

Methods of Using Reoviruses Having Modified Sequences

As described previously (see, for example, U.S. Pat. Nos. 6,110,461; 6,136,307; 6,261,555; 6,344,195; 6,576,234; and 6,811,775), reoviruses use a host cell's Ras pathway machinery to downregulate double-stranded RNA-activated protein kinase (PKR) and thus replicate in the cell. Based upon these discoveries, methods have been developed for using reovirus to treat proliferative disorders in mammals. Representative mammals include mice, dogs, cats, sheep, goats, cows, horses, pigs, non-human primates, and humans. As used herein, a "patient" includes any mammal with a proliferative disorder.

A "proliferative disorder" is any cellular disorder in which the cells proliferate more rapidly than normal tissue growth. Thus a "proliferating cell" is a cell that is proliferating more rapidly than normal cells. A proliferative disorder includes, but is not limited to, neoplasms, which are also referred to as tumors. A neoplasm includes, but is not limited to, pancreatic cancer, breast cancer, brain cancer (e.g., glioblastoma), lung cancer, prostate cancer, colorectal cancer, thyroid cancer, renal cancer, adrenal cancer, liver cancer, neurofibromatosis, and leukemia. A neoplasm includes a solid neoplasm (e.g. sarcoma or carcinoma) or a cancerous growth affecting the hematopoietic system (e.g., lymphoma or leukemia). Other proliferative disorders include, but are not limited to neurofibromatosis.

Generally, in proliferative disorders for which reovirus is used as a treatment, at least some of the proliferating cells have a mutation in which the Ras gene (or an element of the Ras signaling pathway) is activated, either directly (e.g., by an activating mutation in Ras) or indirectly (e.g., by activation of an upstream or downstream element in the Ras pathway). Activation of an upstream element in the Ras pathway includes, for example, transformation with epidermal growth factor receptor (EGFR) or Sos. See, for example, Wiessmuller & Wittinghofer, 1994, *Cellular Signaling*, 6(3): 247-267; and Barbacid, 1987, *Ann. Rev. Biochem.*, 56, 779-827. Activation of a downstream element in the Ras pathway includes, for example, a mutation within B-Raf. See, for example, Brose et al., 2002, *Cancer Res.*, 62:6997-7000. In addition, reovirus is useful for treating proliferative disorders caused by mutations or dysregulation of PKR. See, for example, Strong et al., 1998, *EMBO J.*, 17:3351-662.

A reovirus having a modified sequence as disclosed herein is administered to a mammal that has a proliferative disorder. As used herein, administration refers to delivery of a reovirus such that the reovirus contacts the proliferating cells. The route by which a reovirus is administered depends on the type of disorder and the location of the proliferating cells. A wide variety of administration routes can be employed. For example, for a solid neoplasm that is accessible, a reovirus is administered by direct injection. For a hematopoietic neoplasm, for example, a reovirus is administered intravenously or intravascularly. For certain neoplasms, e.g., those not easily accessible within the body such as metastases or brain tumors, a reovirus is administered in a manner such that it is transported systemically through the body of the mammal to thereby reach the neoplasm (e.g., intrathecally, intravenously, intramuscularly, subcutaneously, or intra-peritoneally). A reovirus also is administered locally including, for example, topically (e.g., for melanoma), orally (e.g., for oral or esophageal neoplasm), rectally (e.g., for colorectal neoplasm), vaginally (e.g., for cervical or vaginal neoplasm), nasally or by inhalation (e.g., for lung neoplasm). A reovirus is optionally administered by more than one route and/or to more than one location in an individual.

Targeted administration may be used to administer a reovirus. For example, dendritic cells containing a reovirus may be administered to a subject. See, for example, US Publication No. 2008/0014183. In another example of targeted delivery, carrier cells may be used to target cells of a proliferative disorder and prevent immune recognition of a reovirus which they carry. See, for example, Qiao et al., 2008, *Nature Med.*, 14:37-44; and WO 2008/009115.

A reovirus having a modified sequence as disclosed herein is administered in an amount that is sufficient to treat the proliferative disorder (e.g., an "effective amount"). A proliferative disorder is "treated" when administration of a reovirus having a modified sequence to proliferating cells affects one or more symptoms or clinical signs of the disorder including, e.g., increasing lysis (e.g., "oncolysis") of the cells, reducing the number of proliferating cells, reducing the size or progression of a neoplasm, reducing pain associated with the neoplasm, as compared to the signs or symptoms in the absence of the treatment. As used herein, the term "oncolysis" means at least 10% of the proliferating cells are lysed (e.g., at least 20%, 30%, 40%, 50%, or 75% of the cells are lysed). The percentage of lysis can be determined, for example, by measuring the reduction in the size of a neoplasm or in the number of proliferating cells in a mammal, or by measuring the amount of lysis of cells in vitro (e.g., from a biopsy of the proliferating cells).

An effective amount of a reovirus having a modified sequence is determined on an individual basis and is based, at least in part, on the particular reovirus used; the individual's size, age, gender; and the size and other characteristics of the proliferating cells. For example, for treatment of a human, approximately $10^3$ to $10^{12}$ plaque forming units (PFU) of a reovirus is used, depending on the type, size and number of proliferating cells or neoplasms present. The effective amount can be from about 1.0 PFU/kg body weight to about $10^{15}$ PFU/kg body weight (e.g., from about $10^2$ PFU/kg body weight to about $10^{13}$ PFU/kg body weight). A reovirus is administered in a single dose or in multiple doses (e.g., two, three, four, six, or more doses). Multiple doses are administered concurrently or consecutively (e.g., over a period of days or weeks). Treatment with a reovirus having a modified sequence lasts from several days to several months or until diminution of the disease is achieved.

It is contemplated that a reovirus having a modified sequence as disclosed herein is optionally administered in conjunction with surgery or removal of proliferating cells (e.g., a neoplasm). It also is contemplated that a reovirus having a modified sequence is optionally administered in conjunction with or in addition to radiation therapy. It is further contemplated that a reovirus having a modified sequence is optionally administered in conjunction with or in addition to known anticancer compounds, chemotherapeutic agents, and/or immunosuppressive agents. Such agents, include, but are not limited to, 5-fluorouracil, mitomycin C, methotrexate, hydroxyurea, gemcitabine, cyclophosphamide, dacarbazine, mitoxantrone, anthracyclins (Epirubicin, Irinotecan, and Doxurubicin), antibodies to receptors such as herceptin, topoisomerase inhibitors such as etoposide or camptothecin, pregnasome, platinum compounds such as carboplatin and cisplatin, taxanes such as taxol and taxotere, hormone therapies such as tamoxifen and anti-estrogens, interleukins, interferons, aromatase inhibitors, progestational agents, LHRH analogs, mTOR inhibitors (e.g., rapamycin and derivatives thereof; see, for example, Homicsko et al., 2005, *Cancer Res.*, 65:6882-90; and Rao et al., 2004, *Curr. Cancer Drug Targets*, 4:621-35), and combinations thereof.

It is further contemplated that a reovirus having a modified sequence is administered in conjunction with an agent that can increase endothelial permeability and/or decrease interstitial fluid pressure. Such agents include, for example, TNF-α. See, for example, Sacchi et al., 2006, *Clin. Cancer Res.*, 12:175-182. It is contemplated that a reovirus having a modified sequence can be administered in conjunction with any combination of the therapies and agents described herein.

Pharmaceutical Compositions

Pharmaceutical compositions that include one or more reoviruses, at least one of which has a modified sequence as described herein, are provided. See, for example, U.S. Pat. No. 6,576,234. In addition to one or more reoviruses, at least one of which has a modified sequence, a pharmaceutical composition typically includes a pharmaceutically acceptable carrier. A pharmaceutically acceptable carrier includes a solid, semi-solid, or liquid material that acts as a vehicle, carrier or medium for the reovirus. Thus, for example, compositions containing a reovirus having a modified sequence are in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Some examples of suitable carriers include phosphate-buffered saline or another physiologically acceptable buffer, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. A pharmaceutical composition additionally can include, without limitation, lubricating agents such as talc, magnesium stearate, and mineral oil; wetting agents; emulsifying and suspending agents; preserving agents such as methyl- and propylhydroxy-benzoates; sweetening agents; and flavoring agents. Pharmaceutical compositions of the invention can be formulated to provide quick, sustained or delayed release of a reovirus having a modified sequence after administration by employing procedures known in the art. In addition to the representative formulations described below, other suitable formulations for use in a pharmaceutical composition are found in Remington: The Science and Practice of Pharmacy (2003, Gennaro & Gennaro, eds., Lippincott Williams & Wilkens).

For preparing solid compositions such as tablets, a reovirus having a modified sequence is mixed with a pharmaceutical carrier to form a solid composition. Optionally, tablets or pills are coated or otherwise compounded to provide a dosage form affording the advantage of prolonged action. For example, a tablet or pill comprises an inner dosage and an outer dosage component, the latter being in the form of an envelope over the former. The two components, for example, are separated by an enteric layer which serves to resist disintegration in the stomach and permit the inner component to pass intact into the duodenum or to be delayed in release. A variety of materials are used for such enteric layers or coatings, such materials including a number of polymeric acids and mixtures of polymeric acids with such materials as shellac, cetyl alcohol, and cellulose acetate.

Liquid formulations that include a reovirus having a modified sequence for oral administration or for injection generally include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. These liquid or solid compositions optionally contain suitable pharmaceutically acceptable excipients as described herein. Such compositions are administered, for example, by the oral or nasal respiratory route for local or systemic effect. Compositions in pharmaceutically acceptable solvents are nebulized by use of inert gases. Nebulized solutions are inhaled, for example, directly from the nebulizing device, from an attached face mask tent, or from an intermittent positive pressure breathing machine. Solution, suspension, or powder compositions are administered, orally or nasally, for example, from devices which deliver the formulation in an appropriate manner.

Another formulation that is employed in the methods taught herein employs transdermal delivery devices ("patches"). Such transdermal patches are used to provide continuous or discontinuous infusion of a reovirus having a modified sequence. The construction and use of transdermal patches for the delivery of pharmaceutical agents are performed according to methods known in the art. See, for example, U.S. Pat. No. 5,023,252. Such patches are constructed for continuous, pulsatile, or on-demand delivery of a reovirus having a modified sequence.

A reovirus having a modified sequence is optionally chemically or biochemically pretreated (e.g., by treatment with a protease such as chymotrypsin or trypsin) prior to administration (e.g., prior to inclusion in the pharmaceutical composition). Pretreatment with a protease removes the outer coat or capsid of the virus and can be used to increase the infectivity of the virus. Additionally or alternatively, a reovirus having a modified sequence is coated in a liposome or micelle to reduce or prevent an immune response in a mammal that has developed immunity toward a reovirus. Such reoviruses are referred to as "immunoprotected reoviruses." See, for example, U.S. Pat. Nos. 6,565,831 and 7,014,847.

A reovirus having a modified sequence or a pharmaceutical composition comprising such a reovirus can be packaged into a kit. It is contemplated that a kit optionally includes one or more chemotherapeutic agents and/or immunosuppressive agents (e.g., anti-antireovirus antibodies). A pharmaceutical composition, for example, is formulated in a unit dosage form. The term "unit dosage forms" refers to physically discrete units suitable as unitary dosages for human subjects and other mammals, each unit containing a predetermined quantity of a reovirus having a modified sequence calculated to produce the desired therapeutic effect in association with a suitable pharmaceutically acceptable carrier.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the invention described in the claims.

EXAMPLES

Example 1

Sequencing and Analysis

Cultures for production of reovirus were initiated from a suspension-adapted HEK 293 S Master Cell Bank (MCB). HEK 293 cells were maintained in Serum Free Medium (HEK 293 SFM II) supplemented with L-glutamine. HEK 293 cells were expanded and seeded into three 15 L spinner flasks, and further expanded until there was 12 L in each of the three flasks. Infection of the HEK 293 cells by reovirus was performed by direct inoculation of the virus into the cell culture. The virus was harvested when the viability of the HEK 293 S cells had decreased by 20-50% post-infection. The virus material from all three spinners was pooled in a single sterile container and agitated to create a homogeneous mixture. Three liters of the pooled cell suspension was removed, transferred to conical tubes, and centrifuged at 3000 rpm for 15 minutes. The cells were then resuspended with 100 mL of clarified conditioned medium, snap frozen in an alcohol-dry ice bath three times, and then filled into sterile, labeled cryovials for use as a seed stock.

A viral stock was prepared by performing a three-time plaque purification. Adherent HEK 293 S cells were plated onto 6-well tissue culture plates, infected with the seed stock described above, and two of the largest plaques were picked. These two plaques were separately amplified and harvested and two of the largest plaques were picked again. This procedure was repeated again for a total of three times. Of the two plaques, one was selected as seed stock for subsequent expansions.

Cultures were initiated from the same suspension adapted HEK 293 S MCB described above and were maintained in the same HEK 293 Serum Free Medium (HEK 293 SFM II) supplemented with L-glutamine. Cells were expanded from T-flasks up to multiple 3 L spinner flasks. The infection was performed by first diluting the plaque-purified virus in HEK 293 SFM media and then adding 8 to 12 mL of the diluted virus into the cell culture. The virus was harvested when the viability of the HEK 293 S cells had decreased by 20-50% following infection, and microscopic examination of each of the spinners confirmed the lack of microbial contamination and that a cytopathic effect (CPE) was present in the cells. CPE was indicated by cells having a swollen and granular appearance. The material from the spinners was pooled in a single sterile container, agitated to create a homogeneous mixture, and a bulk harvest sample removed. The remaining pooled cell suspension was transferred to conical tubes and centrifuged at 3000 rpm for 15 minutes. The cells were then resuspended with 400 mL of clarified conditioned medium, and the concentrated cell suspension was snap-frozen in an alcohol-dry ice bath three times to lyse the cells and then filled into sterile, labeled cryovials for use in sequencing reactions.

Both RNA strands were sequenced from both directions, and the sequence of each of the 10 genomic segments was assembled from the overlapping contigs. The assembled sequence of each genomic segment was used in a BLAST search of the NCBI database (on the World Wide Web). Alignments with three or four different reovirus sequences found in the NCBI database were examined and the alignment having the highest amount of homology was used for further analysis. The polymorphisms or modifications compared to other reported sequences are shown in Table 1. Those modifications that are unique to the selected reovirus strain are indicated with an asterisk in Table 1.

TABLE 1

| | | Modifications Identified | |
|---|---|---|---|
| Genomic Segment | Position (nucleotide; amino acid) | Published Sequence (nucleotide; amino acid) | Novel Polymorphism (nucleotide; amino acid) |
| S1 | | GenBank Accession No. M10262.1 | SEQ ID NO: 1 |
| | 499; 163 | A; Thr | T; Ser |
| S3 | | GenBank Accession No. X01627.1 | SEQ ID NO: 3 |
| | 1057; 344 | T; *Leu* | C; *Leu* |
| S4 | | GenBank Accesion No. K02739 | SEQ ID NO: 4 |
| * | 74; 14 | G; *Leu* | A; *Leu* |
| * | 624; 198 | G; Glu | A; Lys |
| | 719; 229 | G; Glu | T; Asp |
| M1 | | GenBank Accession No. AF461684.1 | SEQ ID NO: 5 |
| | 1129; 372 | G; Met | T; Ile |
| * | 1595; 528 | G; *Ala* | T; Ser |
| M2 | | GenBank Accession No. M20161.1 | SEQ ID NO: 6 |
| * | 248; 73 | A; Glu | C; Asp |
| | 302; 91 | G; *Ala* | C; *Ala* |
| | 303; 92 | C; *Leu* | T; *Leu* |
| | 305; 92 | T; *Leu* | G; *Leu* |
| | 709-10; 227 | CG; Thr | GC; Ser |
| | 1173; 382 | T; *Leu* | C; *Leu* |
| L1 | | GenBank Accession No. M24734.1 | SEQ ID NO: 8 |
| * | 660; 214 | A; *Val* | T; *Val* |
| * | 817; 267 | T; Ser | G; Ala |
| * | 1687; 557 | C; Pro | A; Thr |
| * | 2283; 755 | C; Asn | G; Lys |
| * | 2284-6; 756 | GAT; Asp | ATG; Met |
| * | 2794; 926 | A; Thr | C; Pro |
| * | 2905; 963 | T; Ser | C; Pro |
| * | 2953; 979 | A; Met | C; *Leu* |
| * | 3153; 1045 | C; Ser | A; Arg |
| * | 3231; 1071 | T; *Val* | G; *Val* |

TABLE 1-continued

Modifications Identified

| Genomic Segment | Position (nucleotide; amino acid) | Published Sequence (nucleotide; amino acid) | Novel Polymorphism (nucleotide; amino acid) |
|---|---|---|---|
| L2 | | GenBank Accession No. J03488.1 | SEQ ID NO: 9 |
| | 1838-40; 609 | TTT; Phe | GGG; Gly |
| | 3703; 1230 | A; *Leu* | G; *Leu* |
| L3 | | GenBank Accession No. AF129822 | SEQ ID NO: 10 |
| | 1512; 500 | T; Ile | G; Ser |
| | 2569; 852 | G; Gln | T; His |

\* designates unique modifications; italicized residues indicate silent modifications; position numbers are with respect to the indicated GenBank Accession No.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular modification of a reovirus or treatment regime is disclosed and discussed and a number of modifications that can be made to the reovirus or regime are discussed, each and every combination and permutation of the reovirus and the regime are specifically contemplated unless specifically indicated to the contrary. Likewise, any subset or combination of these is also specifically contemplated and disclosed.

What is claimed is:

1. A method of making an improved reovirus, comprising the steps of:
   modifying the nucleic acid sequence of said reovirus, and
   selecting one or more improved reoviruses, wherein the improved reovirus comprises a lambda-3 polypeptide having an amino acid modification which is a Leu at residue 979, an Arg at residue 1045 or a combination thereof, numbered relative to SEQ ID NO:23 (GenBank Accession no. M24734.1).

2. The method of claim 1, wherein the modifying comprises mutagenizing the reovirus.

3. The method of claim 1, wherein the mutagenizing comprises site-directed mutagenesis.

4. The method of claim 1, wherein the mutagenizing comprises chemical mutagenesis.

5. The method of claim 1, wherein the modifying comprises culturing said reovirus in a human cell line.

6. The method of claim 1, wherein the improved reovirus is selected for an increased rate of lysis; an increased size of plaque formation; an increased rate of RNA replication; an increased rate of RNA transcription; an increased rate of translation; an increased rate of virus assembly and/or packaging; an increased number of viral progeny; an increased ability of a reovirus to be taken up by a host cell; an increased or enhanced ability to uncoat; enhanced cell lysis or inducement to cell death including apoptosis, necrosis or autophagy; an enhanced ability to infect, lyse and kill human neoplastic cells lines; decreased immunogenicity in mammalian cells; differential susceptibility to interferon sensitivity; decreased toxicity toward the host; enhanced drug interaction; enhanced radiotherapy interaction; or the ability to release effective tumor epitopes.

7. The method of claim 1, wherein the improved reovirus further comprises one or more additional amino acid modifications selected from the group consisting of a Val at residue 214, an Ala at residue 267, a Thr at residue 557, a Lys at residue 755, a Met at residue 756, a Pro at residue 926, a Pro at residue 963, a Val at residue 1071, or any combination thereof, numbered relative to SEQ ID NO:23 (GenBank Accession no. M24734.1).

8. The method of claim 1, wherein the improved reovirus comprises SEQ ID NO:19.

9. The method of claim 1, wherein the improved reovirus comprises one or more polypeptides selected from the group consisting of a sigma-3 polypeptide comprising SEQ ID NO:15, a mu-1 polypeptide comprising SEQ ID NO:17, a mu-2 polypeptide comprising SEQ ID NO:16, and a sigma-2 polypeptide comprising SEQ ID NO:12.

10. The method of claim 1, wherein the improved reovirus exhibits a growth advantage over a reovirus that does not contain a modification.

11. The method of claim 1, wherein the improved reovirus comprises a sigma-2 polypeptide comprising SEQ ID NO:12.

12. The method of claim 1, wherein the improved reovirus comprises a sigma-3 polypeptide comprising SEQ ID NO:15.

13. The method of claim 1, wherein the improved reovirus comprises a mu-1 polypeptide comprising SEQ ID NO:17.

14. The method of claim 1, wherein the improved reovirus comprises a mu-2 polypeptide comprising SEQ ID NO:16.

* * * * *

SEQUENCE LISTING

```
<160> NUMBER OF SEQ ID NOS: 30

<210> SEQ ID NO 1
<211> LENGTH: 1416
<212> TYPE: DNA
<213> ORGANISM: Reovirus

<400> SEQUENCE: 1
gctattggtc ggatggatcc tcgcctacgt gaagaagtag tacggctgat aatcgcatta      60
acgagtgata atggagcatc actgtcaaaa gggcttgaat caagggtctc ggcgctcgag     120
aagacgtctc aaatacactc tgatactatc ctccggatca cccagggact cgatgatgca     180
aacaaacgaa tcatcgctct tgagcaaagt cgggatgact tggttgcatc agtcagtgat     240
gctcaacttg caatctccag attggaaagc tctatcggag ccctccaaac agttgtcaat     300
ggacttgatt cgagtgttac ccagttgggt gctcgagtgg gacaacttga gacaggactt     360
gcagagctac gcgttgatca cgacaatctc gttgcgagag tggatactgc agaacgtaac     420
attggatcat tgaccactga gctatcaact ctgacgttac gagtaacatc catacaagcg     480
gatttcgaat ctaggatatc cacgttagag cgcacggcgg tcactagcgc gggagctccc     540
ctctcaatcc gtaataaccg tatgaccatg ggattaaatg atggactcac gttgtcaggg     600
aataatctcg ccatccgatt gccaggaaat acgggtctga atattcaaaa tggtggactt     660
cagtttcgat ttaatactga tcaattccag atagttaata ataacttgac tctcaagacg     720
actgtgtttg attctatcaa ctcaaggata ggcgcaactg agcaaagtta cgtggcgtcg     780
gcagtgactc ccttgagatt aaacagtagc acgaaggtgc tggatatgct aatagacagt     840
tcaacacttg aaattaattc tagtggacag ctaactgtta gatcgacatc cccgaatttg     900
aggtatccga tagctgatgt tagcggcggt atcggaatga gtccaaatta taggtttagg     960
```

```
cagagcatgt ggataggaat tgtctcctat tctggtagtg ggctgaattg gagggtacag   1020
gtgaactccg acatttttat tgtagatgat tacatacata tatgtcttcc agcttttgac   1080
ggtttctcta tagctgacgg tggagatcta tcgttgaact ttgttaccgg attgttacca   1140
ccgttactta caggagacac tgagcccgct tttcataatg acgtggtcac atatggagca   1200
cagactgtag ctatagggtt gtcgtcgggt ggtgcgcctc agtatatgag taagaatctg   1260
tgggtggagc agtggcagga tggagtactt cggttacgtg ttgagggggg tggctcaatt   1320
acgcactcaa acagtaagtg gcctgccatg accgtttcgt acccgcgtag tttcacgtga   1380
ggatcagacc accccgcggc actggggcat tcatc                              1416

<210> SEQ ID NO 2
<211> LENGTH: 1331
<212> TYPE: DNA
<213> ORGANISM: Reovirus

<400> SEQUENCE: 2
gctattcgct ggtcagttat ggctcgcgct gcgttcctat tcaagactgt tgggtttggt     60
ggtctgcaaa atgtgccaat taacgacgaa ctatcttcac atctactccg agctggtaat    120
tcaccatggc agttaacaca gttttttagac tggataagcc ttgggagggg tttagctaca   180
tcggctctcg ttccgacggc tgggtcaaga tactatcaaa tgagttgcct tctaagtggc    240
actctccaga ttccgttccg tcctaaccac cgatggggag acattaggtt cttacgctta    300
gtgtggtcag ctcctactct cgatggatta gtcgtagctc caccacaagt tttggctcag    360
cccgctttgc aagcacaggc agatcgagtg tacgactgcg atgattatcc atttctagcg    420
cgtgatccaa gattcaaaca tcgggtgtat cagcaattga gtgctgtaac tctacttaac    480
ttgacaggtt ttggcccgat ttcctacgtt cgagtggatg aagatatgtg gagtggagat    540
gtgaaccagc ttctcatgaa ctatttcggg cacacgtttg cagagattgc atacacattg    600
tgtcaagcct cggctaatag gccttgggaa tatgacggta catatgctag gatgactcag    660
attgtgttat ccttgttctg gctatcgtat gtcggtgtaa ttcatcagca gaatacgtat    720
cggacattct attttcagtg taatcggcga ggtgacgccg ctgaggtgtg gattcttttct   780 tgttcgttga accattccgc acaaattaga ccgggtaatc gtagcttatt cgttatgcca    840
actagcccag attggaacat ggacgtcaat ttgatcctga gttcaacgtt gacggggtgt    900
ttgtgttcgg gttcacagct gccactgatt gacaataatt cagtacctgc agtgtcgcgt    960
aacatccatg gctggactgg tagagctggt aaccaattgc atgggttcca ggtgagacga   1020
atggtgactg aattttgtga caggttgaga cgcgatggtg tcatgaccca agctcagcag   1080
aatcaagttg aagcgttggc agatcagact caacagttta gagggacaa gctcgaaacg    1140 tgggcgagag aagacgatca atataatcag gctcatccca actccacaat gttccgtacg   1200
aaaccattta cgaatgcgca atggggacga ggtaatacgg gggcgactag tgccgcgatt   1260
gcagccctta tctgatcgtc ttggagtgag ggggtccccc cacacacctc acgactgacc   1320
acacattcat c                                                        1331

<210> SEQ ID NO 3
<211> LENGTH: 1198
<212> TYPE: DNA
<213> ORGANISM: Reovirus
```

```
<400> SEQUENCE: 3
gctaaagtca cgcctgtcgt cgtcactatg gcttcctcac tcagagctgc gatctccaag      60
atcaagaggg atgacgtcgg tcagcaagtt tgtcctaatt atgtcatgct gcggtcctct     120
gtcacaacaa aggtggtacg aaatgtggtt gagtatcaaa ttcgtacggg cggattcttt     180
tcgtgcttag ctatgctaag gccactccag tacgctaagc gtgagcgttt gcttggtcag     240
aggaatctgg aacgtatatc gactagggat atccttcaga ctcgtgattt acactcacta     300
tgtatgccaa ctcctgatgc gccaatgtct aatcatcaag catccaccat gagagagctg     360
atttgcagtt acttcaaggt cgatcatgcg gatgggttga aatatatacc catggatgag     420
agatactctc cgtcatcact tgccagattg tttaccatgg gcatggctgg gctgcacatt     480
accactgagc catcttataa gcgtgttccg attatgcact tagctgcgga cttggactgt     540
atgacgctgg ctctacctta catgattacg cttgatggtg atactgtggt tcctgtcgct     600
ccaacactgt cagcggaaca gcttctggac gacggactca aaggattagc atgcatggat     660
atctcctatg gatgtgaggt ggacgcgaat agccggccgg ctggtgatca gagtatggac     720
tcttcacgct gcatcaacga gttgtattgc gaggagacag cagaagccat ctgtgtgctt     780
aagacatgcc ttgtgttaaa ttgcatgcag ttttaaactttg agatggatga cctagcacat     840
```
(Note: line 840 shown as typed)

Corrected line 840:
```
aagacatgcc ttgtgttaaa ttgcatgcag tttaaacttg agatggatga cctagcacat     840
aacgctgctg agctggacaa gatacagatg atgatacccct tcagtgagcg tgttttttagg     900 atggcctcgt cctttgcgac tattgatgcc cagtgtttta ggttttgcgt gatgatgaag     960
gataaaaatc tgaaaataga tatgcgtgaa acgacgagac tgtggactcg ttcagcatca    1020
gatgattctg tggccacgtc atctttaagt atttccctgg accggggtcg atgggtggcg    1080
gctgacgcca gtgatgctag actgctggtt tttccgattc gcgtgtaatg ggtgagtgag    1140
ctgatgtggt cgccaagaca tgtgccggtg tcttggtggt gggtgacgcc taatcatc     1198
```

<210> SEQ ID NO 4
<211> LENGTH: 1196
<212> TYPE: DNA
<213> ORGANISM: Reovirus

<400> SEQUENCE: 4

```
gctattttg cctcttccca gacgttgtcg caatggaggt gtgcttgccc aacggtcatc      60
aggtcgtgga cttaattaac aacgcttttg aaggtcgtgt atcaatctac agcgcgcaag     120
agggatggga caaaacaatc tcagcacagc cagatatgat ggtatgtggt ggcgccgtcg     180
tttgcatgca ttgtctaggt gttgttggat ctctacaacg caagctgaag catttgcctc     240
accatagatg taatcaacag atccgtcatc aggattacgt cgatgtacag ttcgcagacc     300
gtgttactgc tcactggaag cggggtatgc tgtccttcgt tgcgcagatg cacgagatga     360
tgaatgacgt gtcgccagat gacctggatc gtgtgcgtac tgagggaggt tcactagtgg     420
agctgaaccg gcttcaggtt gacccaaatt caatgtttag atcaatacac tcaagttgga     480
cagatccttt gcaggtggtg gacgaccttg acactaagct ggatcagtac tggacagcct     540
taaacctgat gatcgactca tccgacttga tacccaactt tatgatgaga gacccatcac     600
acgcgttcaa tggtgtgaaa ctgaagggag atgctcgtca aacccaattc tccaggactt     660
ttgattcgag atcgagtttg gaatggggtg tgatggttta tgattactct gagctggatc     720
atgatccatc gaagggccgt gcttacagaa aggaattggt gacgccagct cgagatttcg     780
gtcactttgg attatcccat tattctaggg cgactacccc aatccttgga agatgccgg     840 ccgtattctc aggaatgttg actgggaact gtaaaatgta tccattcatt aaaggaacgg     900
```

| | |
|---|---|
| ctaagctgaa gacagtgcgc aagctagtgg aggcagtcaa tcatgcttgg ggtgtcgaga | 960 |
| agattagata tgctcttggg ccaggtggca tgacgggatg gtacaatagg actatgcaac | 1020 |
| aggcccccat tgtgctaact cctgctgctc tcacaatgtt cccagatacc atcaagtttg | 1080 |
| gggatttgaa ttatccagtg atgattggcg atccgatgat tcttggctaa acacccccat | 1140 |
| cttcacagcg ccgggcttga ccaacctggt gtgacgtggg acaggcttca ttcatc | 1196 |

<210> SEQ ID NO 5
<211> LENGTH: 2304
<212> TYPE: DNA
<213> ORGANISM: Reovirus

<400> SEQUENCE: 5

| | |
|---|---|
| gctattcgcg gtcatggctt acatcgcagt tcctgcggtg gtggattcac gttcgagtga | 60 |
| ggctattgga ctgctagaat cgtttggagt agacgctggg gctgacgcga atgacgtttc | 120 |
| atatcaagat catgactatg tgttggatca gttacagtac atgttagatg gatatgaggc | 180 |
| tggtgacgtt atcgatgcac tcgtccacaa gaattggtta catcactctg tctattgctt | 240 |
| gttgccaccc aaaagtcaac tattagagta ttggaaaagt aatccttcag cgataccgga | 300 |
| caacgttgat cgtcggcttc gtaaacgact aatgctaaag aaagatctca ggaaagatga | 360 |
| tgaatacaat cagctagcgc gtgctttcaa gatatcggat gtctacgcac ctctcatctc | 420 |
| atccacgacg tcaccgatga caatgataca gaacttgaat cgaggcgaga tcgtgtacac | 480 |
| cacgacggac agggtaatag gggctagaat cttgttatat gctcctagaa agtactatgc | 540 |
| gtcaactctg tcatttacta tgactaagtg catcattccg tttggtaaag aggtgggtcg | 600 |
| tgttcctcac tctcgattta atgttggcac atttccgtca attgctaccc cgaaatgttt | 660 |
| tgtcatgagt ggggttgata ttgagtccat cccaaatgaa tttatcaagt tgttttacca | 720 |
| gcgcgtcaag agtgttcacg ctaacatact aaatgacata tctcctcaga tcgtctctga | 780 |
| catgataaac agaaagcgtc tgcgcgttca tactccatca gatcgtcgag ccgcgcagtt | 840 |
| gatgcatttg ccttaccatg ttaaacgagg agcgtctcac gtcgacgttt acaaggtgga | 900 |
| tgttgtagac atgttgttcg aggtagtgga tgtggccgat gggttgcgca acgtatctag | 960 |
| gaaactaact atgcataccg ttcctgtatg tattcttgaa atgttgggta ttgagattgc | 1020 |
| ggactattgc attcgtcaag aggatggaat gctcacagat tggttcctac ttttaaccat | 1080 |
| gctatctgat ggcttgactg atagaaggac gcattgtcaa tacttgatta atccgtcaag | 1140 |
| tgtgcctcct gatgtgatac ttaacatctc aattactgga tttataaata gacatacaat | 1200 |
| cgatgtcatg cctgacatat atgacttcgt taaacccatt ggcgctgtgc tgcctaaggg | 1260 |
| atcatttaaa tcaacaatta tgagagttct tgattcaata tcaatattag gaatccaaat | 1320 |
| catgccgcgc gcgcatgtag ttgactcaga tgaggtgggc gagcaaatgg agcctacgtt | 1380 |
| tgagcaggcg gttatggaga tacaaaagg gattgctggc gttgactcgc tggatgatct | 1440 |
| catcaagtgg gtgttgaact cggatctcat tccgcatgat gacaggcttg gtcaattatt | 1500 |
| tcaagcgttt ttgcctctcg caaaggactt attagctcca atggccagaa agttttatga | 1560 |
| taactcaatg agtgagggta gattgctaac attctctcat gccgacagtg agttgctgaa | 1620 |
| cgcaaattat tttggtcatt tattgcgact aaaaatacca tatattacag aggttaatct | 1680 |
| gatgattcgc aagaatcgtg agggtggaga gctatttcag cttgtgttat cttatctata | 1740 |
| taaaatgtat gctactagcg cgcagcctaa atggtttgga tcattattgc gattgttaat | 1800 |
| atgtccctgg ttacatatgg agaaattaat aggagaagca gacccggcat ctacgtcggc | 1860 |

| | |
|---|---|
| tgaaattggg tggcatatcc ctcgtgaaca gctgatgcaa gatggatggt gtggatgtga | 1920 |
| agacggattc attccctatg ttagcatacg tgcgccaaga ctggttatag aggagttgat | 1980 |
| ggagaagaac tggggccaat atcatgccca agttattgtc actgatcagc ttgtcgtagg | 2040 |
| cgaaccgcgg agggtatctg ctaaggctgt gatcaagggt aaccacttac cagttaagtt | 2100 |
| agtttcacga tttgcatgtt tcacattgac ggcgaagtat gagatgaggc tttcgtgcgg | 2160 |
| ccatagcact ggacgtggag ctgcatacag tgcgagacta gctttccgat ctgacttggc | 2220 |
| gtgatccgtg acatgcgtag tgtgacacct gctcctaggt caatgggggt aggggcggg | 2280 |
| ctaagactac gtacgcgctt catc | 2304 |

<210> SEQ ID NO 6
<211> LENGTH: 2204
<212> TYPE: DNA
<213> ORGANISM: Reovirus

<400> SEQUENCE: 6

| | |
|---|---|
| ggctaatctg ctgaccgtta ctctgcaaag atggggaacg cttcctctat cgttcagacg | 60 |
| atcaacgtca ctggagatgg caatgtattt aaaccatcag ctgaaacttc atctaccgct | 120 |
| gtaccatcgt taagcttatc acctggaatg ctgaatcccg aggggtacc atggattgct | 180 |
| gttggagatg agacatctgt gacttcacca ggcgcattac gtcgaatgac gtcaaaggac | 240 |
| atcccggaca cggcaataat caacacagac aattcatcag cgccgtgcc aagcgaatca | 300 |
| gccttggtgc cctacatcga tgagccgctg gtagtggtta cagagcatgc tattaccaac | 360 |
| ttcaccaaag ctgagatggc acttgaattc aatcgtgagt ccttgacaa gatgcgtgtg | 420 |
| ctgtcagtgt caccaaaata ttcggatctt ctgacctatg ttgactgcta cgtcggtgtg | 480 |
| tctgctcgtc aggcttttaa caattttcag aaacaagtgc ctgtgattac acctactagg | 540 |
| cagacgatgt atgtcgactc gatacaagcg gccttgaaag ctttagaaaa gtgggagatt | 600 |
| gatctgagag tggctcaaac gttgctgcct acgaacgttc cgattggaga agtctcttgt | 660 |
| ccaatgcagt cggtagtgaa actgctggat gatcagctgc cagatgacag cctgatacgg | 720 |
| aggtatccca aggaagccgc cgtcgctttg gctaaacgaa acgggggaat acaatggatg | 780 |
| gacgtatcag aaggcaccgt gatgaacgag gctgtcaacg ctgttgcagc tagtgcactg | 840 |
| gcaccttcag catcagcccc acccttagaa gagaagtcaa agttaaccga caagcgatg | 900 |
| gatctcgtga ccgcggctga gcctgagata attgcctcac tcgcgccagt tcccgcaccc | 960 |
| gtgtttgcca taccacctaa accagcagat tataatgtgc gtactctgag gatcgacgag | 1020 |
| gccacttggc tgcgaatgat tccaaaatca tgaacacac cttttcaaat ccaggtgact | 1080 |
| gataacacag gaactaattg gcatctcaat ttgagggggg ggactcgtgt agtgaatctg | 1140 |
| gaccaaatcg ctccgatgcg gtttgtatta gatctagggg gaaagagtta taagagacg | 1200 |
| agctgggatc caaacggcaa gaaggtcgga ttcatcgttt ttcaatcgaa gataccattc | 1260 |
| gaactttgga ctgctgcttc acagatcggt caagccacgg tggttaacta tgtccaacta | 1320 |
| tacgctgaag acagctcatt taccgcgcag tctatcattg ctactacctc tttggcttat | 1380 |
| aactatgagc ctgagcagtt gaataagact gaccctgaga tgaattatta tcttttggcg | 1440 |
| acctttatag actcagccgc tataacgcca acgaatatga cacagcctga tgtttgggat | 1500 |
| gccttgctga cgatgtcccc actatcagct ggcgaggtga cagtgaaggg tgcggtagtg | 1560 |
| agtgaagtag tccctgcaga cttgataggt agctacactc cagaatccct aaacgcctca | 1620 |
| cttccgaatg atgctgctag atgcatgatc gatagagctt cgaagatagc cgaagcaatc | 1680 |

```
aagattgatg atgatgctgg accagatgaa tattccccaa actctgtacc aattcaaggt    1740
cagcttgcta tctcgcaact cgaaactgga tatggtgtgc gaatattcaa ccctaaaggg    1800
atcctttcta aaattgcatc tagggcaatg caggctttca ttggtgaccc gagcacaatc    1860
atcacgcagg cggcgccagt gttatcagac aagaataatt ggattgcatt ggcacaggga    1920
gtgaaaacta gtctgcgtac taaaagtcta tcagcgggag tgaagactgc agtgagtaag    1980
ctgagctcat ctgagtctat ccagaattgg actcaaggat tcttggataa agtgtcagcg    2040
cattttccag caccaaagcc cgattgtccg actagcggag atagtggtga atcgtctaat    2100
cgccgagtga agcgcgactc atacgcagga gtggtcaaac gtgggtacac acgttaggcc    2160
gctcgccctg gtgacgcggg gttaagggat gcaggcaaat catc                    2204

<210> SEQ ID NO 7
<211> LENGTH: 2241
<212> TYPE: DNA
<213> ORGANISM: Reovirus

<400> SEQUENCE: 7
gctaaagtga ccgtggtcat ggcttcattc aagggattct ccgccaacac tgttccagtt     60
tctaaggcca agcgtgacat atcatctctt gccgctactc ctggacttcg ttcacaatcc    120
ttcactccgt ctgtggatat gtctcaatcg cgtgaattcc tcacaaaggc aattgagcaa    180
gggtccatgt ctataccttta tcagcatgtg aatgtaccga aagttgatcg taaagttgtt    240
agcctggtag tgcgaccttt ctcttcaggt gctttctcta tctctggagt gatttcgcca    300
gcccatgcct atctactaga gtgtctaccc cagcttgagc aggcgatggc ttttgttgct    360
tcacctgagt cttttccagg cttccgacgtc gcgaagcgct tgccataaa gccaggtatg    420 agcctccagg atgccatcac tgcctttatt aactttgtgt ccgcgatgct gaaaatgacg    480
gtgactcgtc aaaactttga cgttattgtg gctgagatcg agaggcttgc ttcaaccagc    540
gtgtccgtca ggactgaaga agcgaaggtt gctgatgagg agctaatgct attcgggtta    600
gatcatagag ggccacagca gctggatgtt tctgacgcta aagggataat gaaggctgct    660
gatattcaga caactcatga tgtccatttg gcaccaggcg ttggtaatat tgatcctgaa    720
atctataacg agggcggtt catgttcatg cagcacaagc cacttgcggc ggatcaatcg    780 tatttcaccct tggagactgc ggattatttc aagatttatc caacatacga tgaacatgat    840
ggcaggatgg ctgaccaaaa gcagtcggga ttgatactgt gtactaagga cgaggtattg    900
gctgagcaaa ctatatttaa actggacgcc cctgatgaca agactgttca tctgttggat    960
cgcgatgacg accacgttgt tgccagagttt actaaggtat ttatagagga cgtggctccc   1020
gggcatcatg ctgctcaaag atcgggacaa cgctctgtgc ttgatgacct atatgcgaat   1080
acgcaagtga tttccattac ttctgctgct ttaaagtggg tggtcaagca cggcgtatct   1140
gatggaatcg tgaacaggaa gaatgtcaaa gtgtgtgttg gttttgaccc cctgtacacc   1200
ttgtctacac ataacggggt gtccttatgt gccctgctga tggacgaaaa actctctgtg   1260
ctgaacagtg cgtgtcgtat gacgttacgc tcactcatga agaccggacg cgacgttgat   1320
gcacacagag cttttcagcg agtcctctct caaggataca catcgctaat gtgctactat   1380
catccttcac ggaagttggc atatggtgag gtgctctttc tagaacgatc caatgacgtg   1440
acagatggga tcaagcttca gttggacgca tctagacagt gtcatgaatg tcctgtgttg   1500
cagcagaaaa tggttgagtt agagaaacag attattatgc agaagtcaat ccagtcgac   1560 cctacccag tggcgctgca accattgttg tctcagttgc gtgagttgtc tagtgaagtt   1620
```

```
actaggctac agatggagtt gagtcgagct cagtccctga atgctcagtt ggaggcggat    1680
gtcaagtcag ctcaatcatg tagcttggat atgtatctga cacaccacac ttgcattaat    1740
ggtcatgcta agaagatga attgcttgac gctgtgcgtg tcgcgccgga tgtgaggaga     1800
gaaatcatgg aaaagaggag tgaagtgaga caaggttggt gcgaacgtat ttctaaggaa    1860
gcagctgcca atgtcaaac tgttattgat gacctgactt tgatgaatgg aaagcaagca    1920
caagagataa cagaattacg tgattcggct gaaaaatatg agaaacagat tgcagagctg    1980
gtgagtacca tcacccaaaa ccagataacg tatcagcaag agctacaagc cttggtagcg    2040
aaaaatgtgg aattggacgc gttgaatcag cgtcaggcta agtctttgcg tattactccc    2100
tctcttctat cagccactcc tatcgattca gttgatgatg ttgctgactt aattgatttc    2160
tctgttccaa ctgatgagtt gtaaataatc cgtgatgcag tgttgcccta atcccttaag    2220
ccttcccgac ccccattcat c                                              2241

<210> SEQ ID NO 8
<211> LENGTH: 3854
<212> TYPE: DNA
<213> ORGANISM: Reovirus

<400> SEQUENCE: 8
gctacacgtt ccacgacaat gtcatccatg atactgactc agtttggacc gttcattgag     60
agcatttcag gtatcactga tcaatcgaat gacgtgtttg aagatgcagc aaaagcattc    120
tctatgttta ctcgcagcga tgtctacaag gcgctggatg aaataccttt ctctgatgat    180
gcgatgcttc caatccctcc aactatatat acgaaaccat ctcacgattc atattattac    240
attgatgctc taaaccgtgt gcgtcgcaaa acatatcagg gccctgatga cgtgtacgta    300
cctaattgtt ctattgttga attgctggag ccacatgaga ctctgacatc ttatgggcgg    360
ttgtccgagg ccatcgagaa tcgtgccaag gatggggaca gccaagccag aatcgccaca    420
acgtatggta gaatcgctga atctcaagct cgacagatta aggctccatt ggagaagttt    480
gtgttggcac tattagtggc cgaagcaggg gggtctttat atgatccagt tttgcagaag    540
tatgatgaga ttccagatct atcgcataat tgccctttat ggtgttttag agagatctgt    600
cgtcacatat ctggtccatt accagatcgg gcaccttatc tttacttatc tgcaggggtt    660
ttctggttaa tgtcaccacg aatgacgtct gcaatccctc cgctactatc cgatcttgtt    720
aatttagcta ttttgcaaca aactgcgggt ttagatccat cattagtgaa attgggagta    780
cagatatgcc ttcatgcagc agctagctca agttatgcat ggtttatctt aaagactaag    840
tctatttttc ctcaaaacac gttgcacagt atgtatgaat ctctagaagg gggatactgt    900
cctaatcttg aatggttaga gcctagatca gactataagt tcatgtacat gggagtcatg    960
ccattgtccg ctaagtatgc taggtcggcg ccgtccaatg ataagaaagc gcgggaactt    1020
ggcgagaaat atggactgag ctcagtcgtc ggtgagcttc gtaaacggac aaagacgtat    1080
gttaaacatg actttgcttc agtgaggtac attcgtgacg ctatggcatg tactagcggt    1140
attttcttgg taagaacacc caccgaaacg gtattgcaag aatatacgca gagtccggag    1200
attaaggttc ccattcccca gaaagactgg acaggcccaa taggtgaaat cagaattcta    1260
aaagatacaa caagttccat cgcgcgttac ttatatagaa catggtactt ggcagcggcg    1320
agaatggcgg ctcaaccacg tacgtgggat ccattgtttc aagcgattat gagatctcaa    1380
tacgtgacag ctaggggtgg atctggcgca gcactccgcg aatctttgta tgcaatcaat    1440
gtgtcgttac ctgatttcaa gggcttacca gtgaaggcag caactaagat attccaggcg    1500
```

```
gcacaattag cgaacttgcc gttctcccac acatcagtgg ctatactagc tgacacttca    1560
atgggattgc gaaatcaggt gcagaggcgg ccacgatcca ttatgccatt aaatgtgccc    1620
cagcagcagg tttcggcgcc ccatacattg acagcggatt acattaacta ccacatgaat    1680
ctatcaacca cgtctggtag tgcggtcatt gagaaggtga ttcctttagg tgtatacgct    1740
tcgagccctc ctaaccagtc gatcaacatt gacatatctg cgtgtgacgc tagtattact    1800
tgggatttct ttctgtcagt gattatggcg gctatacacg aaggtgtcgc tagtagctcc    1860
attggaaaac catttatggg ggttcctgca tccattgtaa atgatgagtc tgtcgttgga    1920
gtgagagctg ctaggccgat atcgggaatg cagaacatga ttcagcatct atcgaaacta    1980
tataaacgtg gattttcata tagagtaaac gattcttttt ctccaggtaa cgattttact    2040
catatgacta ccactttccc gtcaggttca acagccacct ctactgagca tactgctaat    2100
aatagtacga tgatggaaac tttcctgaca gtatggggac ccgaacatac tgacgaccct    2160
gacgtcttac gtttaatgaa gtctttaact attcaaagga attacgtatg tcaaggtgat    2220 gatgattaa tgattatcga tgggactact gctggtaagg tgaacagtga aactattcag    2280
aagatgctag aattaatctc aaaatatggt gaggaattcg gatggaaata tgacatagcg    2340
tacgatggga ctgccgaata cttaaagcta tacttcatat ttggctgtcg aattccaaat    2400
cttagtcgcc atccaatcgt ggggaaagaa cgggcgaatt cttcagcaga ggagccatgg    2460
ccagcaattc tagatcagat tatgggtgtc ttctttaatg tgttcatga tgggttacag    2520 tggcagcggt ggatacgtta ttcatgggct ctatgctgtg ctttctcacg tcaaagaaca    2580
atgattggta gagcgtggg ttaccttcaa tatcctatgt ggtcttttgt ctactgggga    2640
ttaccactgg ttaaagcgtt tgggtcagac ccatggatat tttcttggta catgcctact    2700
ggagatctgg gaatgtatag ttggattagc ttgatacgcc ctctgatgac aagatggatg    2760
gtggctaatg gttacgtaac tgacagatgc tcacccgtat tcgggaacgc agattatcgc    2820
aggtgtttca atgaacttaa actatatcaa ggttattata tggcacaatt gcccaggaat    2880
cctaagaagt ctggacgagc ggcccctcgg gaggtaagag aacaattcac tcaggcatta    2940
tccgactatc tactgcaaaa tccagagctg aagtcacgtg tgctacgtgg tcgtagtgag    3000
tgggagaaat atggagcggg gataattcac aatcctccgt cattattcga tgtgccccat    3060
aaatggtatc agggtgcgca agaggcagca atcgctacga gaagagagct ggcagaaatg    3120
gatgagacat taatgcgcgc tcgaaggcac agatattcga gcttttcaaa gttattagag    3180
gcgtatctgc tcgtgaaatg gcgaatgtgc gaggcccgcg aaccgtcggt ggatttgcga    3240
ttaccattat gtgcgggtat tgacccatta aactcagatc ctttctcaa gatggtaagc    3300 gttggaccaa tgctccagag tacgagaaag tactttgctc agacactatt catggcaaag    3360
acggtgtcgg gtcttgacgt taacgcgatt gatagcgcgt tattacgact gcgaacatta    3420
ggtgctgata agaaagcatt aacgcgcag ttattaatgg tggggcttca ggagtcagaa    3480
gcggacgcat tggccgggaa gataatgcta caggatgtga atactgtgca attagccaga    3540
gtggttaact tagctgtgcc agatacttgg atgtcgttag actttgactc tatgttcaaa    3600
caccacgtca agctgcttcc caaagatgga cgtcatctaa atactgatat tcctcctcga    3660
atgggatggt tacgggccat tttacgattc ttaggtgccg aatggtaat gactgcgact    3720 ggagttgctg tcgacatcta tctgaggat atacatggcg gtggtcggtc acttggacag    3780
agattcatga cttggatgcg acaggaagga cggtcagcgt gagtctacca tgggtcgtgg    3840
tgcgtcaact catc                                                     3854
```

```
<210> SEQ ID NO 9
<211> LENGTH: 3916
<212> TYPE: DNA
<213> ORGANISM: Reovirus

<400> SEQUENCE: 9
gctaaatggc gcgatggcga acgtttgggg ggtgagactt gcagactcgt tatcttcacc      60
cactattgag acacgaacgc gtcagtatac cttacacgat ctttgctcag acctagatgc     120
taatccgggg agggaaccgt ggaaacctct gcgtaatcag cgtactaata atattgtggc     180
tgtgcaatta ttcagaccat tgcagggttt agttttagat acccagcttt atggatttcc     240
aggagcattt gatgactggg agcgattcat gagagagaag ctgcgtgtgc taaagtatga     300
agtattgcgc atctatccaa tcagcaacta tagcaatgaa catgtcaacg tcttcgtggc     360
caatgctttg gtgggcgctt cctgtcgaa tcaagctttc tatgacctgc taccgttgtt     420
gataattaat gacactatga ttggtgatct acttggcacg ggggcatcgc tatcacagtt     480
ctttcaatct catggagatg tgctggaagt cgcagctggt cgtaagtatc tgcagatgga     540
aaactactcc aacgatgacg atgatcctcc attatttgcg aaagacctgt cagattatgc     600
taaagcattc tacagtgaca catatgaagt gttggacagg ttcttttgga cgcatgactc     660
ttcagcgggg gtcttagtgc attatgataa gccaacgaat ggtcatcact atctgctggg     720
tactttgact cagatggtca gtgcacctcc ttatattatt aacgctactg acgcaatgtt     780
gcttgaatcc tgtctagaac agttctcagc taatgtgcgt gcgagacctg cgcaacccgt     840
tacacgctta gaccaatgct atcatttaag atggggagca caatatgtag gagaagattc     900
actgacatat cggttgggg tgttatcctt gctggctacc aatggatatc aattagctag     960
accgattcca agacagttga cgaatcgatg gttgtcgagc tttgtgagtc aaattatgtc    1020
tgacggcgtc aacgagactc cactgtggcc ccaagaaagg tatgtgcaga tcgcttatga    1080
ttcaccatcc gttgttgatg gggctacgca atatggctat gtcaggaaga atcaactcag    1140
actcggcatg agaatatcgg cgctgcaatc gctgagtgat acgccctcgc cggtacagtg    1200
gcttccacaa tacaccatcg accaggcagc gatggacgaa ggcgatctga tggttagtcg    1260
gcttacgcaa ctcccgttac gtcctgatta tggtaatatc tgggtcggcg atgcgctatc    1320
ctattatgtg gactacaatc ggagtcatcg agtcgtgctt tcatcggaac ttcctcagct    1380
tccggacaca tattttgatg gcgatgaaca gtatgggcgc agcctgttct cactagctcg    1440
taagattggt gaccgctcgt tagtgaaaga tacggctgtc ttgaagcacg cttaccaagc    1500
catcgatcca aatactggta aggagtatct gagatctcgg caatctgtcg catatttggg    1560
tgcatcagcg ggtcattctg gtgccgacca gccgttagtc atagagccct ggattcaagg    1620
gaaaatcagt ggtgtgccgc caccctcctc agtgcgacag ttcggctatg atgttgcccg    1680
tggcgcgatc gtcgatctgg cgagaccatt tccttctgga gattatcaat ttgtctattc    1740
ggatgttgac caggtggtcg atggccatga cgatctgagt atatcatctg gactggtgga    1800 gagcctttg tcttcatgca tgcacgccac agcacccggg ggctcatttg ttgttaagat    1860
aaattttccg actagacccg tatggcacta catcgaacag aagatcttgc ccaatattac    1920
gtcatacatg ttgatcaagc ctttcgtcac caacaacgtc gaattgttct tcgtcgcttt    1980
cggtgtgcat caacactcat cacttacttg gacatctgga gtgtacttct tcttggtgga    2040 ccattttat cgttatgaga ctttatctac gatctcacga caattgccgt cttttgggta    2100
tgttgatgat gggtcttccg tgactggtat cgagacaatt agtattgaga accctggctt    2160
```

```
ctcgaatatg acccaggccg ctcgcattgg tatctcagga ttgtgtgcta atgtaggtaa      2220
cgcgcgtaag tccattgcca tttacgaatc tcatggggcc agagtattaa ctatcacatc      2280
aaggagatct ccggcatcag ctagaagaaa gtctaggttg cgatatttgc cattaataga      2340
ccctaggtcg ttagaggtac aggcgcgcac tattctgcca gctgatccag tgttatttga      2400
aaacgtgagc ggagcgtcac cccatgtttg tctgacaatg atgtacaact cgaagtgtc       2460 gtcagcggta tatgatggag acgttgtgct agatctgggg acgggaccag aggctaaaat      2520
ccttgaactg ataccgcaa cctctccagt cacatgcgtg gacatacggc ctacagcgca       2580
gcctagtgga tgttggaacg ttcgtaccac gttccttgag ttagattatt tgagcgatgg      2640
atggatcact ggggtgcgtg gggacatagt tacttgtatg ttatctttgg gggccgctgc      2700
cgctggaaaa tcaatgactt ttgacgctgc gtttcagcaa ttaatcaaag tattatccaa      2760
gagtacggct aatgttgtgc tggtgcaggt taactgccct acagacgtgg tgaggagcat      2820
taagggctac ctagagatag attcgactaa caagaggtat aggttcccca aatttggtcg      2880
agacgagccg tactctgaca tggatgcgct ggagaaaata tgtcgtaccg cctggccaaa      2940
ctgctcaatt acctgggttc cattgtcata cgacttgcgg tggactagac tggcattatt      3000
agagtccacg acattgagta gcgcgtcgat tagaattgct gagctgatgt ataaatacat      3060
gcctattatg aggattgata ttcatggact acccatggaa aagcgaggta acttcatagt      3120
ggggcagaac tgctcattag taatccctgg ttttaatgcg caggatgtct ttaactgtta      3180
tttcaattcc gccctcgctt tctcgactga agatgtcaat gctgcgatga ttccccaagt      3240
gtctgcgcag tttgatgcga ctaagggtga gtggacgttg gatatggtct ctccgacgc       3300 aggaatctat accatgcagg ctctagtggg atctaatgct aatccagtct ctttgggttc      3360
ctttgtagtt gattctccag atgtagatat aactgacgct tggccagctc agttagactt      3420
tacgatcgcg ggaactgatg tcgatataac agttaatcct tattaccgtc tgatgacctt      3480
tgtaaggatc gatggacagt ggcagattgc caatccagac aaatttcaat tcttttcgtc      3540
ggcgtctggg acgttagtga tgaacgtcaa attagatatc gcagataaat atctactata      3600
ctatatacga gatgtccagt ctcgagatgt tggcttttac attcagcatc cacttcaact      3660
tttgaatacg atcacattgc caaccaacga ggaccttttt ctgagcgcac ctgacatgcg      3720
agagtgggca gttaaggaaa gcggtaacac gatatgtata ctcaatagtc aagggtttgt      3780
gctacctcaa gattgggatg tgttaacaga taccataagt tggtccccat cgatacccac      3840
atacattgtg ccaccgggtg attataccttt gactcctctg taactcactg tccctcgtga      3900
gcgcgcctaa ttcatc                                                       3916

<210> SEQ ID NO 10
<211> LENGTH: 3901
<212> TYPE: DNA
<213> ORGANISM: Reovirus

<400> SEQUENCE: 10
gctaatcgtc aggatgaagc ggattccaag gaagacaaag ggcaaatcca gcggaaaggg        60
caatgactca acagagagag cggacgatgg ctcgagccaa ttaagagaca agcaaaacaa       120
taaggctggc cccgccacta cggagcctgg cacatccaac cgagagcaat acaaagctcg       180
accaggtatt gcatctgtgc agagggccac tgaaagtgca gaaatgccca tgaagaataa       240
tgacgaaggg acgccagata agaaaggaaa tactaagggc gacctagtta atgagcatag       300
tgaggctaaa gacgaggcgg atgaagcgac gaagaagcag gcaaaggata cagacaaaag       360
```

-continued

| | | | | |
|---|---|---|---|---|
| taaagcgcaa | gtcacatatt | cagacactgg | tatcaataat | gctaatgaac tgtcaagatc | 420 |
| tgggaatgtg | gataatgagg | gtggaagtaa | tcagaagccg | atgtctacca gaatagctga | 480 |
| ggcaacgtct | gctatagtgt | cgaaacatcc | tgcgcgtgtt | gggctgccac ctaccgctag | 540 |
| cagtggtcat | gggtatcagt | gccatgtctg | ttctgcagtc | ctgtttagtc ctttagacct | 600 |
| agatgcccac | gtcgcctcac | atggtttgca | tggtaacatg | acattaacat cgagtgatat | 660 |
| ccagcgacat | ataactgagt | tcatcagctc | atggcaaaat | catcctattg ttcaagtttc | 720 |
| ggctgatgtc | gaaaataaga | aaactgctca | attgcttcac | gctgacactc ctcgactcgt | 780 |
| cacttgggat | gctggtttgt | gtacttcatt | caaaatcgtc | ccgattgtgc cagctcaggt | 840 |
| gccgcaggat | gtactggcct | atacgttttt | cacctcttca | tacgctatcc aatcaccgtt | 900 |
| tccagaggcg | gcagtgtcta | ggattgtggt | gcatacgaga | tggcatctaa atgttgactt | 960 |
| tgaccgagac | tcgtctgtca | tcatggcgcc | acctacagaa | aacaatatcc atttgtttaa | 1020 |
| acagttacta | aatactgaaa | ccctgtctgt | aaggggggct | aatccgctaa tgttcagggc | 1080 |
| gaatgtgttg | catatgttgc | tagagttcgt | attagataac | ttgtatctga acagacatac | 1140 |
| gggattctct | caagaccaca | cgccatttac | tgagggtgct | aatttgcgtt cacttcctgg | 1200 |
| ccccgatgct | gagaaatggt | actcgattat | gtatccaacg | cgcatgggaa cgccgaatgt | 1260 |
| atccaaaata | tgtaatttcg | tcgcctcttg | tgtgcgaaat | cgggttggac ggtttgatcg | 1320 |
| agcacagatg | atgaacggag | ctatgtcaga | gtgggtggat | gtcttcgaga cttcagacgc | 1380 |
| gctaaccgtc | tccattcgag | gtcgatggat | ggctagacta | gctcgcatga acataaatcc | 1440 |
| aacagagatc | gaatgggcat | tgactgaatg | tgcacaagga | tatgtgactg tcacaagtcc | 1500 |
| ttacgctcct | agcgtaaata | gattgatgcc | ctatcgtatc | tccaacgctg agcggcaaat | 1560 |
| atcacagata | atcaggatca | tgaacattgg | caataacgcg | acggtgatac aacctgttct | 1620 |
| gcaagatatt | tcggtactcc | ttcaacgcat | atcaccactc | caaatagatc caactattat | 1680 |
| ttccaacact | atgtcaacag | tctcggagtc | tactactcag | accctcagcc ccgcgtcctc | 1740 |
| aattttgggt | aaactacgac | caagcaactc | agattttttct | agttttagag tcgcgttggc | 1800 |
| tggatggctt | tataatgggg | ttgtgacgac | ggtgattgat | gatagttcat atccaaaaga | 1860 |
| cggcggcagc | gtgacctcac | ttgaaaatct | gtgggatttc | ttcatccttg cgcttgctct | 1920 |
| accactgaca | actgacccct | gtgcacctgt | gaaagcattc | atgaccctag ccaacatgat | 1980 |
| ggttggtttc | gagacaatcc | ctatggataa | tcagatctat | actcaatcga gacgcgcgag | 2040 |
| tgctttctca | acgcctcaca | cgtggccacg | atgctttatg | aacatccagt taatttctcc | 2100 |
| aatcgacgct | cccatcttgc | gacagtgggc | tgaaattatt | catagatact ggcctaaccc | 2160 |
| ttcacagatt | cgttatggtg | caccgaacgt | tttcggctcg | gcaaatttgt tcactccacc | 2220 |
| tgaggtgctg | ttattgccaa | tcgatcatca | accagctaat | gtaacaacgc caacgctgga | 2280 |
| cttcaccaat | gagttaacta | attggcgcgc | tcgtgtctgt | gagcttatga agaatctcgt | 2340 |
| tgataaccaa | agatatcaac | ctggatggac | acaaagtcta | gtctcgtcaa tgcgcggaac | 2400 |
| gctagacaaa | ttgaagttga | ttaaatcgat | gacaccaatg | tatctgcaac agctggctcc | 2460 |
| ggtagagtta | gcagtgatag | ctcccatgtt | gccttttcca | cctttccagg tgccatacgt | 2520 |
| ccgtctcgat | cgtgacagag | ttccaacaat | ggttggagta | acacgacatt cacgagatac | 2580 |
| tattactcag | ccggcgctat | cgctgtcgac | aaccaatact | actgttggcg tgccactagc | 2640 |
| tctagacgcg | agggctatca | ccgttgcgct | gttgtcaggg | aaatatccgc cggatttggt | 2700 |
| gacaaatgta | tggtacgctg | atgccatttta | cccaatgtat | gcagacacgg aggtgttctc | 2760 |

-continued

```
taatcttcag agagacatga ttacctgcga ggccgtgcag acattagtga ctctggtggc    2820
gcaaatatca gagacccagt atcctgtaga taggtatctt gattggatcc catcactgag    2880
agcatcggcg gcgacggcgg cgacatttgc tgagtgggtt aatacttcaa tgaagacggc    2940
gtttgatttg tctgatatgc tgttagagcc tctcctaagc ggtgatccga ggatgactca    3000
actagcgatt cagtatcagc agtacaatgg cagaacgttt aatatcatac ctgaaatgcc    3060
aggttcagta attgctgact gcgttcaatt aacagcagaa gtctttaatc acgaatataa    3120
cctgtttggg attgcgcggg gtgatatcat cattggccgt gttcagtcga cacatttgtg    3180
gtcaccgctg ctcctccac ctgacctggt gtttgatcgt gatacccctg gtgttcacat     3240
cttcggacga gattgccgta tatcgtttgg aatgaatggc gccgcgccaa tgattagaga    3300
tgagactgga ctgatggtgc cttttgaagg aaattggatt ttcccactgg cgctttggca    3360
aatgaataca cgatattta atcaacagtt cgacgcgtgg attaagacag agagttgcg     3420 aatccgcatt gagatgggcg cgtatccata tatgttgcat tactatgatc cacgtcagta    3480
cgctaatgca tggaatttaa catccgcctg gcttgaagaa attacgccga cgagcatccc    3540
atccgtgcct ttcatggtgc ccatttcaag tgatcatgac atttcctctg ccccagctgt    3600
ccaatatatc atttcaactg aatataatga tcggtctctg ttctgcacta actcatcatc    3660
tccccaaacc atcgctggac cagacaaaca cattccagtt gagagatata acattctgac    3720
caaccccgac gctccaccca cgcagataca actgcctgaa gtcgttgact tgtacaacgt    3780
cgtcacacgc tatgcgtatg agactccgcc tattaccgct gttgttatgg gtgttccttg    3840
atcctcatcc tcccaacagg tgctagagca ttgcgctcaa tgctagttgg gccgattcat    3900
c                                                                    3901
```

<210> SEQ ID NO 11
<211> LENGTH: 455
<212> TYPE: PRT
<213> ORGANISM: Reovirus

<400> SEQUENCE: 11

```
Met Asp Pro Arg Leu Arg Glu Glu Val Val Arg Leu Ile Ile Ala Leu
1               5                   10                  15

Thr Ser Asp Asn Gly Ala Ser Leu Ser Lys Gly Leu Glu Ser Arg Val
            20                  25                  30

Ser Ala Leu Glu Lys Thr Ser Gln Ile His Ser Asp Thr Ile Leu Arg
        35                  40                  45

Ile Thr Gln Gly Leu Asp Asp Ala Asn Lys Arg Ile Ile Ala Leu Glu
    50                  55                  60

Gln Ser Arg Asp Asp Leu Val Ala Ser Val Ser Asp Ala Gln Leu Ala
65                  70                  75                  80

Ile Ser Arg Leu Glu Ser Ser Ile Gly Ala Leu Gln Thr Val Val Asn
                85                  90                  95

Gly Leu Asp Ser Ser Val Thr Gln Leu Gly Ala Arg Val Gly Gln Leu
            100                 105                 110

Glu Thr Gly Leu Ala Glu Leu Arg Val Asp His Asp Asn Leu Val Ala
        115                 120                 125

Arg Val Asp Thr Ala Glu Arg Asn Ile Gly Ser Leu Thr Thr Glu Leu
    130                 135                 140

Ser Thr Leu Thr Leu Arg Val Thr Ser Ile Gln Ala Asp Phe Glu Ser
145                 150                 155                 160
```

```
Arg Ile Ser Thr Leu Glu Arg Thr Ala Val Thr Ser Ala Gly Ala Pro
            165                 170                 175

Leu Ser Ile Arg Asn Asn Arg Met Thr Met Gly Leu Asn Asp Gly Leu
        180                 185                 190

Thr Leu Ser Gly Asn Asn Leu Ala Ile Arg Leu Pro Gly Asn Thr Gly
    195                 200                 205

Leu Asn Ile Gln Asn Gly Gly Leu Gln Phe Arg Phe Asn Thr Asp Gln
210                 215                 220

Phe Gln Ile Val Asn Asn Leu Thr Leu Lys Thr Thr Val Phe Asp
225                 230                 235                 240

Ser Ile Asn Ser Arg Ile Gly Ala Thr Glu Gln Ser Tyr Val Ala Ser
                245                 250                 255

Ala Val Thr Pro Leu Arg Leu Asn Ser Ser Thr Lys Val Leu Asp Met
            260                 265                 270

Leu Ile Asp Ser Ser Thr Leu Glu Ile Asn Ser Ser Gly Gln Leu Thr
        275                 280                 285

Val Arg Ser Thr Ser Pro Asn Leu Arg Tyr Pro Ile Ala Asp Val Ser
    290                 295                 300

Gly Gly Ile Gly Met Ser Pro Asn Tyr Arg Phe Arg Gln Ser Met Trp
305                 310                 315                 320

Ile Gly Ile Val Ser Tyr Ser Gly Ser Gly Leu Asn Trp Arg Val Gln
                325                 330                 335

Val Asn Ser Asp Ile Phe Ile Val Asp Asp Tyr Ile His Ile Cys Leu
            340                 345                 350

Pro Ala Phe Asp Gly Phe Ser Ile Ala Asp Gly Gly Asp Leu Ser Leu
        355                 360                 365

Asn Phe Val Thr Gly Leu Leu Pro Pro Leu Leu Thr Gly Asp Thr Glu
    370                 375                 380

Pro Ala Phe His Asn Asp Val Val Thr Tyr Gly Ala Gln Thr Val Ala
385                 390                 395                 400

Ile Gly Leu Ser Ser Gly Gly Ala Pro Gln Tyr Met Ser Lys Asn Leu
                405                 410                 415

Trp Val Glu Gln Trp Gln Asp Gly Val Leu Arg Leu Arg Val Glu Gly
            420                 425                 430

Gly Gly Ser Ile Thr His Ser Asn Ser Lys Trp Pro Ala Met Thr Val
        435                 440                 445

Ser Tyr Pro Arg Ser Phe Thr
    450                 455

<210> SEQ ID NO 12
<211> LENGTH: 418
<212> TYPE: PRT
<213> ORGANISM: Reovirus

<400> SEQUENCE: 12

Met Ala Arg Ala Ala Phe Leu Phe Lys Thr Val Gly Phe Gly Gly Leu
1               5                   10                  15

Gln Asn Val Pro Ile Asn Asp Glu Leu Ser Ser His Leu Leu Arg Ala
            20                  25                  30

Gly Asn Ser Pro Trp Gln Leu Thr Gln Phe Leu Asp Trp Ile Ser Leu
        35                  40                  45

Gly Arg Gly Leu Ala Thr Ser Ala Leu Val Pro Thr Ala Gly Ser Arg
    50                  55                  60

Tyr Tyr Gln Met Ser Cys Leu Leu Ser Gly Thr Leu Gln Ile Pro Phe
65                  70                  75                  80
```

-continued

```
Arg Pro Asn His Arg Trp Gly Asp Ile Arg Phe Leu Arg Leu Val Trp
                85                  90                  95
Ser Ala Pro Thr Leu Asp Gly Leu Val Val Ala Pro Pro Gln Val Leu
            100                 105                 110
Ala Gln Pro Ala Leu Gln Ala Gln Ala Asp Arg Val Tyr Asp Cys Asp
        115                 120                 125
Asp Tyr Pro Phe Leu Ala Arg Asp Pro Arg Phe Lys His Arg Val Tyr
    130                 135                 140
Gln Gln Leu Ser Ala Val Thr Leu Leu Asn Leu Thr Gly Phe Gly Pro
145                 150                 155                 160
Ile Ser Tyr Val Arg Val Asp Glu Asp Met Trp Ser Gly Asp Val Asn
                165                 170                 175
Gln Leu Leu Met Asn Tyr Phe Gly His Thr Phe Ala Glu Ile Ala Tyr
            180                 185                 190
Thr Leu Cys Gln Ala Ser Ala Asn Arg Pro Trp Glu Tyr Asp Gly Thr
        195                 200                 205
Tyr Ala Arg Met Thr Gln Ile Val Leu Ser Leu Phe Trp Leu Ser Tyr
    210                 215                 220
Val Gly Val Ile His Gln Gln Asn Thr Tyr Arg Thr Phe Tyr Phe Gln
225                 230                 235                 240
Cys Asn Arg Arg Gly Asp Ala Ala Glu Val Trp Ile Leu Ser Cys Ser
                245                 250                 255
Leu Asn His Ser Ala Gln Ile Arg Pro Gly Asn Arg Ser Leu Phe Val
            260                 265                 270
Met Pro Thr Ser Pro Asp Trp Asn Met Asp Val Asn Leu Ile Leu Ser
        275                 280                 285
Ser Thr Leu Thr Gly Cys Leu Cys Ser Gly Ser Gln Leu Pro Leu Ile
    290                 295                 300
Asp Asn Asn Ser Val Pro Ala Val Ser Arg Asn Ile His Gly Trp Thr
305                 310                 315                 320
Gly Arg Ala Gly Asn Gln Leu His Gly Phe Gln Val Arg Arg Met Val
                325                 330                 335
Thr Glu Phe Cys Asp Arg Leu Arg Arg Asp Gly Val Met Thr Gln Ala
            340                 345                 350
Gln Gln Asn Gln Val Glu Ala Leu Ala Asp Gln Thr Gln Gln Phe Lys
        355                 360                 365
Arg Asp Lys Leu Glu Thr Trp Ala Arg Glu Asp Gln Tyr Asn Gln
    370                 375                 380
Ala His Pro Asn Ser Thr Met Phe Arg Thr Lys Pro Phe Thr Asn Ala
385                 390                 395                 400
Gln Trp Gly Arg Gly Asn Thr Gly Ala Thr Ser Ala Ala Ile Ala Ala
                405                 410                 415
Leu Ile
```

<210> SEQ ID NO 13
<211> LENGTH: 254
<212> TYPE: PRT
<213> ORGANISM: Reovirus

<400> SEQUENCE: 13

```
Met Ala Ser Ser Leu Arg Ala Ala Ile Ser Lys Ile Lys Arg Asp Asp
1               5                   10                  15
Val Gly Gln Gln Val Cys Pro Asn Tyr Val Met Leu Arg Ser Ser Val
            20                  25                  30
```

```
Thr Thr Lys Val Val Arg Asn Val Val Glu Tyr Gln Ile Arg Thr Gly
            35                  40                  45

Gly Phe Phe Ser Cys Leu Ala Met Leu Arg Pro Leu Gln Tyr Ala Lys
 50                  55                  60

Arg Glu Arg Leu Leu Gly Gln Arg Asn Leu Glu Arg Ile Ser Thr Arg
 65                  70                  75                  80

Asp Ile Leu Gln Thr Arg Asp Leu His Ser Leu Cys Met Pro Thr Pro
                    85                  90                  95

Asp Ala Pro Met Ser Asn His Gln Ala Ser Thr Met Arg Glu Leu Ile
                100                 105                 110

Cys Ser Tyr Phe Lys Val Asp His Ala Asp Gly Leu Lys Tyr Ile Pro
                115                 120                 125

Met Asp Glu Arg Tyr Ser Pro Ser Ser Leu Ala Arg Leu Phe Thr Met
130                 135                 140

Gly Met Ala Gly Leu His Ile Thr Thr Glu Pro Ser Tyr Lys Arg Val
145                 150                 155                 160

Pro Ile Met His Leu Ala Ala Asp Leu Asp Cys Met Thr Leu Ala Leu
                165                 170                 175

Pro Tyr Met Ile Thr Leu Asp Gly Asp Thr Val Val Pro Val Ala Pro
                180                 185                 190

Thr Leu Ser Ala Glu Gln Leu Leu Asp Asp Gly Leu Lys Gly Leu Ala
                195                 200                 205

Cys Met Asp Met Asp Val Arg Trp Thr Arg Ile Ala Gly Arg Leu Val
                210                 215                 220

Ile Arg Val Trp Thr Leu His Ala Ala Ser Thr Ser Cys Ile Ala Arg
225                 230                 235                 240

Arg Gln Gln Lys Pro Ser Val Cys Leu Arg His Ala Leu Cys
                245                 250

<210> SEQ ID NO 14
<211> LENGTH: 366
<212> TYPE: PRT
<213> ORGANISM: Reovirus

<400> SEQUENCE: 14

Met Ala Ser Ser Leu Arg Ala Ala Ile Ser Lys Ile Lys Arg Asp Asp
 1               5                  10                  15

Val Gly Gln Gln Val Cys Pro Asn Tyr Val Met Leu Arg Ser Ser Val
                20                  25                  30

Thr Thr Lys Val Val Arg Asn Val Val Glu Tyr Gln Ile Arg Thr Gly
            35                  40                  45

Gly Phe Phe Ser Cys Leu Ala Met Leu Arg Pro Leu Gln Tyr Ala Lys
 50                  55                  60

Arg Glu Arg Leu Leu Gly Gln Arg Asn Leu Glu Arg Ile Ser Thr Arg
 65                  70                  75                  80

Asp Ile Leu Gln Thr Arg Asp Leu His Ser Leu Cys Met Pro Thr Pro
                    85                  90                  95

Asp Ala Pro Met Ser Asn His Gln Ala Ser Thr Met Arg Glu Leu Ile
                100                 105                 110

Cys Ser Tyr Phe Lys Val Asp His Ala Asp Gly Leu Lys Tyr Ile Pro
                115                 120                 125

Met Asp Glu Arg Tyr Ser Pro Ser Ser Leu Ala Arg Leu Phe Thr Met
130                 135                 140

Gly Met Ala Gly Leu His Ile Thr Thr Glu Pro Ser Tyr Lys Arg Val
145                 150                 155                 160
```

```
Pro Ile Met His Leu Ala Ala Asp Leu Asp Cys Met Thr Leu Ala Leu
            165                 170                 175

Pro Tyr Met Ile Thr Leu Asp Gly Asp Thr Val Val Pro Val Ala Pro
        180                 185                 190

Thr Leu Ser Ala Glu Gln Leu Leu Asp Asp Gly Leu Lys Gly Leu Ala
        195                 200                 205

Cys Met Asp Ile Ser Tyr Gly Cys Glu Val Asp Ala Asn Ser Arg Pro
    210                 215                 220

Ala Gly Asp Gln Ser Met Asp Ser Ser Arg Cys Ile Asn Glu Leu Tyr
225                 230                 235                 240

Cys Glu Glu Thr Ala Glu Ala Ile Cys Val Leu Lys Thr Cys Leu Val
                245                 250                 255

Leu Asn Cys Met Gln Phe Lys Leu Glu Met Asp Asp Leu Ala His Asn
            260                 265                 270

Ala Ala Glu Leu Asp Lys Ile Gln Met Met Ile Pro Phe Ser Glu Arg
        275                 280                 285

Val Phe Arg Met Ala Ser Ser Phe Ala Thr Ile Asp Ala Gln Cys Phe
    290                 295                 300

Arg Phe Cys Val Met Met Lys Asp Lys Asn Leu Lys Ile Asp Met Arg
305                 310                 315                 320

Glu Thr Thr Arg Leu Trp Thr Arg Ser Ala Ser Asp Asp Ser Val Ala
                325                 330                 335

Thr Ser Ser Leu Ser Ile Ser Leu Asp Arg Gly Arg Trp Val Ala Ala
            340                 345                 350

Asp Ala Ser Asp Ala Arg Leu Leu Val Phe Pro Ile Arg Val
        355                 360                 365

<210> SEQ ID NO 15
<211> LENGTH: 365
<212> TYPE: PRT
<213> ORGANISM: Reovirus

<400> SEQUENCE: 15

Met Glu Val Cys Leu Pro Asn Gly His Gln Val Val Asp Leu Ile Asn
1               5                   10                  15

Asn Ala Phe Glu Gly Arg Val Ser Ile Tyr Ser Ala Gln Glu Gly Trp
            20                  25                  30

Asp Lys Thr Ile Ser Ala Gln Pro Asp Met Met Val Cys Gly Gly Ala
        35                  40                  45

Val Val Cys Met His Cys Leu Gly Val Val Gly Ser Leu Gln Arg Lys
    50                  55                  60

Leu Lys His Leu Pro His His Arg Cys Asn Gln Gln Ile Arg His Gln
65                  70                  75                  80

Asp Tyr Val Asp Val Gln Phe Ala Asp Arg Val Thr Ala His Trp Lys
                85                  90                  95

Arg Gly Met Leu Ser Phe Val Ala Gln Met His Glu Met Met Asn Asp
            100                 105                 110

Val Ser Pro Asp Asp Leu Asp Arg Val Arg Thr Glu Gly Gly Ser Leu
        115                 120                 125

Val Glu Leu Asn Arg Leu Gln Val Asp Pro Asn Ser Met Phe Arg Ser
    130                 135                 140

Ile His Ser Ser Trp Thr Asp Pro Leu Gln Val Val Asp Asp Leu Asp
145                 150                 155                 160

Thr Lys Leu Asp Gln Tyr Trp Thr Ala Leu Asn Leu Met Ile Asp Ser
                165                 170                 175
```

-continued

```
Ser Asp Leu Ile Pro Asn Phe Met Met Arg Asp Pro Ser His Ala Phe
            180                 185                 190

Asn Gly Val Lys Leu Lys Gly Asp Ala Arg Gln Thr Gln Phe Ser Arg
        195                 200                 205

Thr Phe Asp Ser Arg Ser Leu Glu Trp Gly Val Met Val Tyr Asp
    210                 215                 220

Tyr Ser Glu Leu Asp His Asp Pro Ser Lys Gly Arg Ala Tyr Arg Lys
225                 230                 235                 240

Glu Leu Val Thr Pro Ala Arg Asp Phe Gly His Phe Gly Leu Ser His
                245                 250                 255

Tyr Ser Arg Ala Thr Thr Pro Ile Leu Gly Lys Met Pro Ala Val Phe
            260                 265                 270

Ser Gly Met Leu Thr Gly Asn Cys Lys Met Tyr Pro Phe Ile Lys Gly
        275                 280                 285

Thr Ala Lys Leu Lys Thr Val Arg Lys Leu Val Glu Ala Val Asn His
    290                 295                 300

Ala Trp Gly Val Glu Lys Ile Arg Tyr Ala Leu Gly Pro Gly Gly Met
305                 310                 315                 320

Thr Gly Trp Tyr Asn Arg Thr Met Gln Gln Ala Pro Ile Val Leu Thr
                325                 330                 335

Pro Ala Ala Leu Thr Met Phe Pro Asp Thr Ile Lys Phe Gly Asp Leu
            340                 345                 350

Asn Tyr Pro Val Met Ile Gly Asp Pro Met Ile Leu Gly
        355                 360                 365

<210> SEQ ID NO 16
<211> LENGTH: 736
<212> TYPE: PRT
<213> ORGANISM: Reovirus

<400> SEQUENCE: 16

Met Ala Tyr Ile Ala Val Pro Ala Val Val Asp Ser Arg Ser Ser Glu
1               5                   10                  15

Ala Ile Gly Leu Leu Glu Ser Phe Gly Val Asp Ala Gly Ala Asp Ala
            20                  25                  30

Asn Asp Val Ser Tyr Gln Asp His Asp Tyr Val Leu Asp Gln Leu Gln
        35                  40                  45

Tyr Met Leu Asp Gly Tyr Glu Ala Gly Asp Val Ile Asp Ala Leu Val
    50                  55                  60

His Lys Asn Trp Leu His His Ser Val Tyr Cys Leu Leu Pro Pro Lys
65                  70                  75                  80

Ser Gln Leu Leu Glu Tyr Trp Lys Ser Asn Pro Ser Ala Ile Pro Asp
                85                  90                  95

Asn Val Asp Arg Arg Leu Arg Lys Arg Leu Met Leu Lys Lys Asp Leu
            100                 105                 110

Arg Lys Asp Asp Glu Tyr Asn Gln Leu Ala Arg Ala Phe Lys Ile Ser
        115                 120                 125

Asp Val Tyr Ala Pro Leu Ile Ser Ser Thr Thr Ser Pro Met Thr Met
    130                 135                 140

Ile Gln Asn Leu Asn Arg Gly Glu Ile Val Tyr Thr Thr Thr Asp Arg
145                 150                 155                 160

Val Ile Gly Ala Arg Ile Leu Leu Tyr Ala Pro Arg Lys Tyr Tyr Ala
                165                 170                 175

Ser Thr Leu Ser Phe Thr Met Thr Lys Cys Ile Ile Pro Phe Gly Lys
            180                 185                 190
```

```
Glu Val Gly Arg Val Pro His Ser Arg Phe Asn Val Thr Phe Pro
            195                 200                 205

Ser Ile Ala Thr Pro Lys Cys Phe Val Met Ser Gly Val Asp Ile Glu
    210                 215                 220

Ser Ile Pro Asn Glu Phe Ile Lys Leu Phe Tyr Gln Arg Val Lys Ser
225                 230                 235                 240

Val His Ala Asn Ile Leu Asn Asp Ile Ser Pro Gln Ile Val Ser Asp
                245                 250                 255

Met Ile Asn Arg Lys Arg Leu Arg Val His Thr Pro Ser Asp Arg Arg
            260                 265                 270

Ala Ala Gln Leu Met His Leu Pro Tyr His Val Lys Arg Gly Ala Ser
        275                 280                 285

His Val Asp Val Tyr Lys Val Asp Val Val Asp Met Leu Phe Glu Val
    290                 295                 300

Val Asp Val Ala Asp Gly Leu Arg Asn Val Ser Arg Lys Leu Thr Met
305                 310                 315                 320

His Thr Val Pro Val Cys Ile Leu Glu Met Leu Gly Ile Glu Ile Ala
                325                 330                 335

Asp Tyr Cys Ile Arg Gln Glu Asp Gly Met Leu Thr Asp Trp Phe Leu
            340                 345                 350

Leu Leu Thr Met Leu Ser Asp Gly Leu Thr Asp Arg Arg Thr His Cys
        355                 360                 365

Gln Tyr Leu Ile Asn Pro Ser Ser Val Pro Pro Asp Val Ile Leu Asn
    370                 375                 380

Ile Ser Ile Thr Gly Phe Ile Asn Arg His Thr Ile Asp Val Met Pro
385                 390                 395                 400

Asp Ile Tyr Asp Phe Val Lys Pro Ile Gly Ala Val Leu Pro Lys Gly
                405                 410                 415

Ser Phe Lys Ser Thr Ile Met Arg Val Leu Asp Ser Ile Ser Ile Leu
            420                 425                 430

Gly Ile Gln Ile Met Pro Arg Ala His Val Val Asp Ser Asp Glu Val
        435                 440                 445

Gly Glu Gln Met Glu Pro Thr Phe Glu Gln Ala Val Met Glu Ile Tyr
    450                 455                 460

Lys Gly Ile Ala Gly Val Asp Ser Leu Asp Asp Leu Ile Lys Trp Val
465                 470                 475                 480

Leu Asn Ser Asp Leu Ile Pro His Asp Asp Arg Leu Gly Gln Leu Phe
                485                 490                 495

Gln Ala Phe Leu Pro Leu Ala Lys Asp Leu Leu Ala Pro Met Ala Arg
            500                 505                 510

Lys Phe Tyr Asp Asn Ser Met Ser Glu Gly Arg Leu Leu Thr Phe Ser
        515                 520                 525

His Ala Asp Ser Glu Leu Leu Asn Ala Asn Tyr Phe Gly His Leu Leu
    530                 535                 540

Arg Leu Lys Ile Pro Tyr Ile Thr Glu Val Asn Leu Met Ile Arg Lys
545                 550                 555                 560

Asn Arg Glu Gly Gly Glu Leu Phe Gln Leu Val Leu Ser Tyr Leu Tyr
                565                 570                 575

Lys Met Tyr Ala Thr Ser Ala Gln Pro Lys Trp Phe Gly Ser Leu Leu
            580                 585                 590

Arg Leu Leu Ile Cys Pro Trp Leu His Met Glu Lys Leu Ile Gly Glu
        595                 600                 605
```

```
Ala Asp Pro Ala Ser Thr Ser Ala Glu Ile Gly Trp His Ile Pro Arg
    610             615                 620
Glu Gln Leu Met Gln Asp Gly Trp Cys Gly Cys Glu Asp Gly Phe Ile
625                 630                 635                 640
Pro Tyr Val Ser Ile Arg Ala Pro Arg Leu Val Ile Glu Glu Leu Met
                645                 650                 655
Glu Lys Asn Trp Gly Gln Tyr His Ala Gln Val Ile Val Thr Asp Gln
                660                 665                 670
Leu Val Val Gly Glu Pro Arg Val Ser Ala Lys Ala Val Ile Lys
                675                 680                 685
Gly Asn His Leu Pro Val Lys Leu Val Ser Arg Phe Ala Cys Phe Thr
    690                 695                 700
Leu Thr Ala Lys Tyr Glu Met Arg Leu Ser Cys Gly His Ser Thr Gly
705                 710                 715                 720
Arg Gly Ala Ala Tyr Ser Ala Arg Leu Ala Phe Arg Ser Asp Leu Ala
                725                 730                 735

<210> SEQ ID NO 17
<211> LENGTH: 708
<212> TYPE: PRT
<213> ORGANISM: Reovirus

<400> SEQUENCE: 17

Met Gly Asn Ala Ser Ser Ile Val Gln Thr Ile Asn Val Thr Gly Asp
1               5                   10                  15
Gly Asn Val Phe Lys Pro Ser Ala Glu Thr Ser Ser Thr Ala Val Pro
                20                  25                  30
Ser Leu Ser Leu Ser Pro Gly Met Leu Asn Pro Gly Gly Val Pro Trp
                35                  40                  45
Ile Ala Val Gly Asp Glu Thr Ser Val Thr Ser Pro Gly Ala Leu Arg
    50                  55                  60
Arg Met Thr Ser Lys Asp Ile Pro Asp Thr Ala Ile Ile Asn Thr Asp
65                  70                  75                  80
Asn Ser Ser Gly Ala Val Pro Ser Glu Ser Ala Leu Val Pro Tyr Ile
                85                  90                  95
Asp Glu Pro Leu Val Val Val Thr Glu His Ala Ile Thr Asn Phe Thr
                100                 105                 110
Lys Ala Glu Met Ala Leu Glu Phe Asn Arg Glu Phe Leu Asp Lys Met
                115                 120                 125
Arg Val Leu Ser Val Ser Pro Lys Tyr Ser Asp Leu Leu Thr Tyr Val
    130                 135                 140
Asp Cys Tyr Val Gly Val Ser Ala Arg Gln Ala Leu Asn Asn Phe Gln
145                 150                 155                 160
Lys Gln Val Pro Val Ile Thr Pro Thr Arg Gln Thr Met Tyr Val Asp
                165                 170                 175
Ser Ile Gln Ala Ala Leu Lys Ala Leu Glu Lys Trp Glu Ile Asp Leu
                180                 185                 190
Arg Val Ala Gln Thr Leu Leu Pro Thr Asn Val Pro Ile Gly Glu Val
    195                 200                 205
Ser Cys Pro Met Gln Ser Val Lys Leu Leu Asp Asp Gln Leu Pro
    210                 215                 220
Asp Asp Ser Leu Ile Arg Arg Tyr Pro Lys Glu Ala Ala Val Ala Leu
225                 230                 235                 240
Ala Lys Arg Asn Gly Gly Ile Gln Trp Met Asp Val Ser Glu Gly Thr
                245                 250                 255
```

-continued

```
Val Met Asn Glu Ala Val Asn Ala Val Ala Ser Ala Leu Ala Pro
            260                 265                 270

Ser Ala Ser Ala Pro Pro Leu Glu Glu Lys Ser Lys Leu Thr Glu Gln
275                 280                 285

Ala Met Asp Leu Val Thr Ala Ala Glu Pro Glu Ile Ile Ala Ser Leu
    290                 295                 300

Ala Pro Val Pro Ala Pro Val Phe Ala Ile Pro Pro Lys Pro Ala Asp
305                 310                 315                 320

Tyr Asn Val Arg Thr Leu Arg Ile Asp Glu Ala Thr Trp Leu Arg Met
                325                 330                 335

Ile Pro Lys Ser Met Asn Thr Pro Phe Gln Ile Gln Val Thr Asp Asn
            340                 345                 350

Thr Gly Thr Asn Trp His Leu Asn Leu Arg Gly Gly Thr Arg Val Val
        355                 360                 365

Asn Leu Asp Gln Ile Ala Pro Met Arg Phe Val Leu Asp Leu Gly Gly
    370                 375                 380

Lys Ser Tyr Lys Glu Thr Ser Trp Asp Pro Asn Gly Lys Lys Val Gly
385                 390                 395                 400

Phe Ile Val Phe Gln Ser Lys Ile Pro Phe Glu Leu Trp Thr Ala Ala
                405                 410                 415

Ser Gln Ile Gly Gln Ala Thr Val Val Asn Tyr Val Gln Leu Tyr Ala
            420                 425                 430

Glu Asp Ser Ser Phe Thr Ala Gln Ser Ile Ile Ala Thr Thr Ser Leu
        435                 440                 445

Ala Tyr Asn Tyr Glu Pro Glu Gln Leu Asn Lys Thr Asp Pro Glu Met
    450                 455                 460

Asn Tyr Tyr Leu Leu Ala Thr Phe Ile Asp Ser Ala Ala Ile Thr Pro
465                 470                 475                 480

Thr Asn Met Thr Gln Pro Asp Val Trp Asp Ala Leu Leu Thr Met Ser
                485                 490                 495

Pro Leu Ser Ala Gly Glu Val Thr Val Lys Gly Ala Val Val Ser Glu
            500                 505                 510

Val Val Pro Ala Asp Leu Ile Gly Ser Tyr Thr Pro Glu Ser Leu Asn
        515                 520                 525

Ala Ser Leu Pro Asn Asp Ala Ala Arg Cys Met Ile Asp Arg Ala Ser
    530                 535                 540

Lys Ile Ala Glu Ala Ile Lys Ile Asp Asp Ala Gly Pro Asp Glu
545                 550                 555                 560

Tyr Ser Pro Asn Ser Val Pro Ile Gln Gly Gln Leu Ala Ile Ser Gln
                565                 570                 575

Leu Glu Thr Gly Tyr Gly Val Arg Ile Phe Asn Pro Lys Gly Ile Leu
            580                 585                 590

Ser Lys Ile Ala Ser Arg Ala Met Gln Ala Phe Ile Gly Asp Pro Ser
        595                 600                 605

Thr Ile Ile Thr Gln Ala Ala Pro Val Leu Ser Asp Lys Asn Asn Trp
    610                 615                 620

Ile Ala Leu Ala Gln Gly Val Lys Thr Ser Leu Arg Thr Lys Ser Leu
625                 630                 635                 640

Ser Ala Gly Val Lys Thr Ala Val Ser Lys Leu Ser Ser Ser Glu Ser
                645                 650                 655

Ile Gln Asn Trp Thr Gln Gly Phe Leu Asp Lys Val Ser Ala His Phe
            660                 665                 670
```

-continued

```
Pro Ala Pro Lys Pro Asp Cys Pro Thr Ser Gly Asp Ser Gly Glu Ser
            675                 680                 685

Ser Asn Arg Arg Val Lys Arg Asp Ser Tyr Ala Gly Val Val Lys Arg
    690                 695                 700

Gly Tyr Thr Arg
705

<210> SEQ ID NO 18
<211> LENGTH: 721
<212> TYPE: PRT
<213> ORGANISM: Reovirus

<400> SEQUENCE: 18

Met Ala Ser Phe Lys Gly Phe Ser Ala Asn Thr Val Pro Val Ser Lys
1               5                   10                  15

Ala Lys Arg Asp Ile Ser Ser Leu Ala Ala Thr Pro Gly Leu Arg Ser
            20                  25                  30

Gln Ser Phe Thr Pro Ser Val Asp Met Ser Gln Ser Arg Glu Phe Leu
        35                  40                  45

Thr Lys Ala Ile Glu Gln Gly Ser Met Ser Ile Pro Tyr Gln His Val
    50                  55                  60

Asn Val Pro Lys Val Asp Arg Lys Val Val Ser Leu Val Val Arg Pro
65                  70                  75                  80

Phe Ser Ser Gly Ala Phe Ser Ile Ser Gly Val Ile Ser Pro Ala His
                85                  90                  95

Ala Tyr Leu Leu Glu Cys Leu Pro Gln Leu Glu Gln Ala Met Ala Phe
            100                 105                 110

Val Ala Ser Pro Glu Ser Phe Gln Ala Ser Asp Val Ala Lys Arg Phe
        115                 120                 125

Ala Ile Lys Pro Gly Met Ser Leu Gln Asp Ala Ile Thr Ala Phe Ile
    130                 135                 140

Asn Phe Val Ser Ala Met Leu Lys Met Thr Val Thr Arg Gln Asn Phe
145                 150                 155                 160

Asp Val Ile Val Ala Glu Ile Glu Arg Leu Ala Ser Thr Ser Val Ser
                165                 170                 175

Val Arg Thr Glu Glu Ala Lys Val Ala Asp Glu Glu Leu Met Leu Phe
            180                 185                 190

Gly Leu Asp His Arg Gly Pro Gln Gln Leu Asp Val Ser Asp Ala Lys
        195                 200                 205

Gly Ile Met Lys Ala Ala Asp Ile Gln Thr Thr His Asp Val His Leu
    210                 215                 220

Ala Pro Gly Val Gly Asn Ile Asp Pro Glu Ile Tyr Asn Glu Gly Arg
225                 230                 235                 240

Phe Met Phe Met Gln His Lys Pro Leu Ala Ala Asp Gln Ser Tyr Phe
                245                 250                 255

Thr Leu Glu Thr Ala Asp Tyr Phe Lys Ile Tyr Pro Thr Tyr Asp Glu
            260                 265                 270

His Asp Gly Arg Met Ala Asp Gln Lys Gln Ser Gly Leu Ile Leu Cys
        275                 280                 285

Thr Lys Asp Glu Val Leu Ala Glu Gln Thr Ile Phe Lys Leu Asp Ala
    290                 295                 300

Pro Asp Asp Lys Thr Val His Leu Leu Asp Arg Asp Asp His Val
305                 310                 315                 320

Val Ala Arg Phe Thr Lys Val Phe Ile Glu Asp Val Ala Pro Gly His
                325                 330                 335
```

```
His Ala Ala Gln Arg Ser Gly Gln Arg Ser Val Leu Asp Asp Leu Tyr
                340                 345                 350
Ala Asn Thr Gln Val Ile Ser Ile Thr Ser Ala Ala Leu Lys Trp Val
            355                 360                 365
Val Lys His Gly Val Ser Asp Gly Ile Val Asn Arg Lys Asn Val Lys
370                 375                 380
Val Cys Val Gly Phe Asp Pro Leu Tyr Thr Leu Ser Thr His Asn Gly
385                 390                 395                 400
Val Ser Leu Cys Ala Leu Leu Met Asp Glu Lys Leu Ser Val Leu Asn
                405                 410                 415
Ser Ala Cys Arg Met Thr Leu Arg Ser Leu Met Lys Thr Gly Arg Asp
            420                 425                 430
Val Asp Ala His Arg Ala Phe Gln Arg Val Leu Ser Gln Gly Tyr Thr
        435                 440                 445
Ser Leu Met Cys Tyr Tyr His Pro Ser Arg Lys Leu Ala Tyr Gly Glu
    450                 455                 460
Val Leu Phe Leu Glu Arg Ser Asn Asp Val Thr Asp Gly Ile Lys Leu
465                 470                 475                 480
Gln Leu Asp Ala Ser Arg Gln Cys His Glu Cys Pro Val Leu Gln Gln
                485                 490                 495
Lys Val Val Glu Leu Glu Lys Gln Ile Ile Met Gln Lys Ser Ile Gln
            500                 505                 510
Ser Asp Pro Thr Pro Val Ala Leu Gln Pro Leu Leu Ser Gln Leu Arg
        515                 520                 525
Glu Leu Ser Ser Glu Val Thr Arg Leu Gln Met Glu Leu Ser Arg Ala
    530                 535                 540
Gln Ser Leu Asn Ala Gln Leu Glu Ala Asp Val Lys Ser Ala Gln Ser
545                 550                 555                 560
Cys Ser Leu Asp Met Tyr Leu Arg His His Thr Cys Ile Asn Gly His
                565                 570                 575
Ala Lys Glu Asp Glu Leu Leu Asp Ala Val Arg Val Ala Pro Asp Val
            580                 585                 590
Arg Arg Glu Ile Met Glu Lys Arg Ser Glu Val Arg Gln Gly Trp Cys
        595                 600                 605
Glu Arg Ile Ser Lys Glu Ala Ala Lys Cys Gln Thr Val Ile Asp
    610                 615                 620
Asp Leu Thr Leu Met Asn Gly Lys Gln Ala Gln Ile Thr Glu Leu
625                 630                 635                 640
Arg Asp Ser Ala Glu Lys Tyr Glu Lys Gln Ile Ala Glu Leu Val Ser
                645                 650                 655
Thr Ile Thr Gln Asn Gln Ile Thr Tyr Gln Gln Glu Leu Gln Ala Leu
            660                 665                 670
Val Ala Lys Asn Val Glu Leu Asp Ala Leu Asn Gln Arg Gln Ala Lys
        675                 680                 685
Ser Leu Arg Ile Thr Pro Ser Leu Leu Ser Ala Thr Pro Ile Asp Ser
    690                 695                 700
Val Asp Val Ala Asp Leu Ile Asp Phe Ser Val Pro Thr Asp Glu
705                 710                 715                 720

Leu

<210> SEQ ID NO 19
<211> LENGTH: 1267
<212> TYPE: PRT
<213> ORGANISM: Reovirus
```

<400> SEQUENCE: 19

```
Met Ser Ser Met Ile Leu Thr Gln Phe Gly Pro Phe Ile Glu Ser Ile
1               5                   10                  15

Ser Gly Ile Thr Asp Gln Ser Asn Asp Val Phe Glu Asp Ala Ala Lys
            20                  25                  30

Ala Phe Ser Met Phe Thr Arg Ser Asp Val Tyr Lys Ala Leu Asp Glu
        35                  40                  45

Ile Pro Phe Ser Asp Asp Ala Met Leu Pro Ile Pro Pro Thr Ile Tyr
    50                  55                  60

Thr Lys Pro Ser His Asp Ser Tyr Tyr Tyr Ile Asp Ala Leu Asn Arg
65                  70                  75                  80

Val Arg Arg Lys Thr Tyr Gln Gly Pro Asp Asp Val Tyr Val Pro Asn
                85                  90                  95

Cys Ser Ile Val Glu Leu Leu Glu Pro His Glu Thr Leu Thr Ser Tyr
            100                 105                 110

Gly Arg Leu Ser Glu Ala Ile Glu Asn Arg Ala Lys Asp Gly Asp Ser
        115                 120                 125

Gln Ala Arg Ile Ala Thr Thr Tyr Gly Arg Ile Ala Glu Ser Gln Ala
    130                 135                 140

Arg Gln Ile Lys Ala Pro Leu Glu Lys Phe Val Leu Ala Leu Leu Val
145                 150                 155                 160

Ala Glu Ala Gly Gly Ser Leu Tyr Asp Pro Val Leu Gln Lys Tyr Asp
                165                 170                 175

Glu Ile Pro Asp Leu Ser His Asn Cys Pro Leu Trp Cys Phe Arg Glu
            180                 185                 190

Ile Cys Arg His Ile Ser Gly Pro Leu Pro Asp Arg Ala Pro Tyr Leu
        195                 200                 205

Tyr Leu Ser Ala Gly Val Phe Trp Leu Met Ser Pro Arg Met Thr Ser
    210                 215                 220

Ala Ile Pro Pro Leu Leu Ser Asp Leu Val Asn Leu Ala Ile Leu Gln
225                 230                 235                 240

Gln Thr Ala Gly Leu Asp Pro Ser Leu Val Lys Leu Gly Val Gln Ile
                245                 250                 255

Cys Leu His Ala Ala Ser Ser Tyr Ala Trp Phe Ile Leu Lys
            260                 265                 270

Thr Lys Ser Ile Phe Pro Gln Asn Thr Leu His Ser Met Tyr Glu Ser
        275                 280                 285

Leu Glu Gly Gly Tyr Cys Pro Asn Leu Glu Trp Leu Glu Pro Arg Ser
    290                 295                 300

Asp Tyr Lys Phe Met Tyr Met Gly Val Met Pro Leu Ser Ala Lys Tyr
305                 310                 315                 320

Ala Arg Ser Ala Pro Ser Asn Asp Lys Lys Ala Arg Glu Leu Gly Glu
                325                 330                 335

Lys Tyr Gly Leu Ser Ser Val Val Gly Glu Leu Arg Lys Arg Thr Lys
            340                 345                 350

Thr Tyr Val Lys His Asp Phe Ala Ser Val Arg Tyr Ile Arg Asp Ala
        355                 360                 365

Met Ala Cys Thr Ser Gly Ile Phe Leu Val Arg Thr Pro Thr Glu Thr
    370                 375                 380

Val Leu Gln Glu Tyr Thr Gln Ser Pro Glu Ile Lys Val Pro Ile Pro
385                 390                 395                 400

Gln Lys Asp Trp Thr Gly Pro Ile Gly Glu Ile Arg Ile Leu Lys Asp
                405                 410                 415
```

```
Thr Thr Ser Ser Ile Ala Arg Tyr Leu Tyr Arg Thr Trp Tyr Leu Ala
            420                 425                 430

Ala Ala Arg Met Ala Ala Gln Pro Arg Thr Trp Asp Pro Leu Phe Gln
        435                 440                 445

Ala Ile Met Arg Ser Gln Tyr Val Thr Ala Arg Gly Gly Ser Gly Ala
    450                 455                 460

Ala Leu Arg Glu Ser Leu Tyr Ala Ile Asn Val Ser Leu Pro Asp Phe
465                 470                 475                 480

Lys Gly Leu Pro Val Lys Ala Ala Thr Lys Ile Phe Gln Ala Ala Gln
                485                 490                 495

Leu Ala Asn Leu Pro Phe Ser His Thr Ser Val Ala Ile Leu Ala Asp
            500                 505                 510

Thr Ser Met Gly Leu Arg Asn Gln Val Gln Arg Arg Pro Arg Ser Ile
        515                 520                 525

Met Pro Leu Asn Val Pro Gln Gln Val Ser Ala Pro His Thr Leu
    530                 535                 540

Thr Ala Asp Tyr Ile Asn Tyr His Met Asn Leu Ser Thr Thr Ser Gly
545                 550                 555                 560

Ser Ala Val Ile Glu Lys Val Ile Pro Leu Gly Val Tyr Ala Ser Ser
                565                 570                 575

Pro Pro Asn Gln Ser Ile Asn Ile Asp Ile Ser Ala Cys Asp Ala Ser
            580                 585                 590

Ile Thr Trp Asp Phe Phe Leu Ser Val Ile Met Ala Ala Ile His Glu
            595                 600                 605

Gly Val Ala Ser Ser Ser Ile Gly Lys Pro Phe Met Gly Val Pro Ala
        610                 615                 620

Ser Ile Val Asn Asp Glu Ser Val Val Gly Val Arg Ala Ala Arg Pro
625                 630                 635                 640

Ile Ser Gly Met Gln Asn Met Ile Gln His Leu Ser Lys Leu Tyr Lys
                645                 650                 655

Arg Gly Phe Ser Tyr Arg Val Asn Asp Ser Phe Ser Pro Gly Asn Asp
            660                 665                 670

Phe Thr His Met Thr Thr Thr Phe Pro Ser Gly Ser Thr Ala Thr Ser
        675                 680                 685

Thr Glu His Thr Ala Asn Asn Ser Thr Met Met Glu Thr Phe Leu Thr
    690                 695                 700

Val Trp Gly Pro Glu His Thr Asp Asp Pro Asp Val Leu Arg Leu Met
705                 710                 715                 720

Lys Ser Leu Thr Ile Gln Arg Asn Tyr Val Cys Gln Gly Asp Asp Gly
                725                 730                 735

Leu Met Ile Ile Asp Gly Thr Ala Gly Lys Val Asn Ser Glu Thr
            740                 745                 750

Ile Gln Lys Met Leu Glu Leu Ile Ser Lys Tyr Gly Glu Glu Phe Gly
        755                 760                 765

Trp Lys Tyr Asp Ile Ala Tyr Asp Gly Thr Ala Glu Tyr Leu Lys Leu
    770                 775                 780

Tyr Phe Ile Phe Gly Cys Arg Ile Pro Asn Leu Ser Arg His Pro Ile
785                 790                 795                 800

Val Gly Lys Glu Arg Ala Asn Ser Ser Ala Glu Glu Pro Trp Pro Ala
                805                 810                 815

Ile Leu Asp Gln Ile Met Gly Val Phe Phe Asn Gly Val His Asp Gly
            820                 825                 830
```

```
Leu Gln Trp Gln Arg Trp Ile Arg Tyr Ser Trp Ala Leu Cys Cys Ala
        835                 840                 845

Phe Ser Arg Gln Arg Thr Met Ile Gly Glu Ser Val Gly Tyr Leu Gln
850                 855                 860

Tyr Pro Met Trp Ser Phe Val Tyr Trp Gly Leu Pro Leu Val Lys Ala
865                 870                 875                 880

Phe Gly Ser Asp Pro Trp Ile Phe Ser Trp Tyr Met Pro Thr Gly Asp
                885                 890                 895

Leu Gly Met Tyr Ser Trp Ile Ser Leu Ile Arg Pro Leu Met Thr Arg
            900                 905                 910

Trp Met Val Ala Asn Gly Tyr Val Thr Asp Arg Cys Ser Pro Val Phe
        915                 920                 925

Gly Asn Ala Asp Tyr Arg Arg Cys Phe Asn Glu Leu Lys Leu Tyr Gln
    930                 935                 940

Gly Tyr Tyr Met Ala Gln Leu Pro Arg Asn Pro Lys Lys Ser Gly Arg
945                 950                 955                 960

Ala Ala Pro Arg Glu Val Arg Glu Gln Phe Thr Gln Ala Leu Ser Asp
                965                 970                 975

Tyr Leu Leu Gln Asn Pro Glu Leu Lys Ser Arg Val Leu Arg Gly Arg
            980                 985                 990

Ser Glu Trp Glu Lys Tyr Gly Ala Gly Ile Ile His Asn Pro Pro Ser
        995                 1000                1005

Leu Phe Asp Val Pro His Lys Trp Tyr Gln Gly Ala Gln Glu Ala Ala
    1010                1015                1020

Ile Ala Thr Arg Glu Glu Leu Ala Glu Met Asp Glu Thr Leu Met Arg
1025                1030                1035                1040

Ala Arg Arg His Arg Tyr Ser Ser Phe Ser Lys Leu Leu Glu Ala Tyr
                1045                1050                1055

Leu Leu Val Lys Trp Arg Met Cys Glu Ala Arg Glu Pro Ser Val Asp
            1060                1065                1070

Leu Arg Leu Pro Leu Cys Ala Gly Ile Asp Pro Leu Asn Ser Asp Pro
        1075                1080                1085

Phe Leu Lys Met Val Ser Val Gly Pro Met Leu Gln Ser Thr Arg Lys
    1090                1095                1100

Tyr Phe Ala Gln Thr Leu Phe Met Ala Lys Thr Val Ser Gly Leu Asp
1105                1110                1115                1120

Val Asn Ala Ile Asp Ser Ala Leu Leu Arg Leu Arg Thr Leu Gly Ala
                1125                1130                1135

Asp Lys Lys Ala Leu Thr Ala Gln Leu Leu Met Val Gly Leu Gln Glu
            1140                1145                1150

Ser Glu Ala Asp Ala Leu Ala Gly Lys Ile Met Leu Gln Asp Val Asn
        1155                1160                1165

Thr Val Gln Leu Ala Arg Val Val Asn Leu Ala Val Pro Asp Thr Trp
    1170                1175                1180

Met Ser Leu Asp Phe Asp Ser Met Phe Lys His His Val Lys Leu Leu
1185                1190                1195                1200

Pro Lys Asp Gly Arg His Leu Asn Thr Asp Ile Pro Pro Arg Met Gly
                1205                1210                1215

Trp Leu Arg Ala Ile Leu Arg Phe Leu Gly Ala Gly Met Val Met Thr
            1220                1225                1230

Ala Thr Gly Val Ala Val Asp Ile Tyr Leu Glu Asp Ile His Gly Gly
        1235                1240                1245
```

Gly Arg Ser Leu Gly Gln Arg Phe Met Thr Trp Met Arg Gln Glu Gly
         1250                1255                1260

Arg Ser Ala
1265

<210> SEQ ID NO 20
<211> LENGTH: 1289
<212> TYPE: PRT
<213> ORGANISM: Reovirus

<400> SEQUENCE: 20

Met Ala Asn Val Trp Gly Val Arg Leu Ala Asp Ser Leu Ser Ser Pro
1               5                   10                  15

Thr Ile Glu Thr Arg Thr Arg Gln Tyr Thr Leu His Asp Leu Cys Ser
            20                  25                  30

Asp Leu Asp Ala Asn Pro Gly Arg Glu Pro Trp Lys Pro Leu Arg Asn
        35                  40                  45

Gln Arg Thr Asn Asn Ile Val Ala Val Gln Leu Phe Arg Pro Leu Gln
    50                  55                  60

Gly Leu Val Leu Asp Thr Gln Leu Tyr Gly Phe Pro Gly Ala Phe Asp
65                  70                  75                  80

Asp Trp Glu Arg Phe Met Arg Glu Lys Leu Arg Val Leu Lys Tyr Glu
                85                  90                  95

Val Leu Arg Ile Tyr Pro Ile Ser Asn Tyr Ser Asn Glu His Val Asn
            100                 105                 110

Val Phe Val Ala Asn Ala Leu Val Gly Ala Phe Leu Ser Asn Gln Ala
        115                 120                 125

Phe Tyr Asp Leu Leu Pro Leu Leu Ile Ile Asn Asp Thr Met Ile Gly
    130                 135                 140

Asp Leu Leu Gly Thr Gly Ala Ser Leu Ser Gln Phe Phe Gln Ser His
145                 150                 155                 160

Gly Asp Val Leu Glu Val Ala Ala Gly Arg Lys Tyr Leu Gln Met Glu
                165                 170                 175

Asn Tyr Ser Asn Asp Asp Asp Pro Pro Leu Phe Ala Lys Asp Leu
            180                 185                 190

Ser Asp Tyr Ala Lys Ala Phe Tyr Ser Asp Thr Tyr Glu Val Leu Asp
        195                 200                 205

Arg Phe Phe Trp Thr His Asp Ser Ser Ala Gly Val Leu Val His Tyr
    210                 215                 220

Asp Lys Pro Thr Asn Gly His His Tyr Leu Leu Gly Thr Leu Thr Gln
225                 230                 235                 240

Met Val Ser Ala Pro Pro Tyr Ile Ile Asn Ala Thr Asp Ala Met Leu
                245                 250                 255

Leu Glu Ser Cys Leu Glu Gln Phe Ser Ala Asn Val Arg Ala Arg Pro
            260                 265                 270

Ala Gln Pro Val Thr Arg Leu Asp Gln Cys Tyr His Leu Arg Trp Gly
        275                 280                 285

Ala Gln Tyr Val Gly Glu Asp Ser Leu Thr Tyr Arg Leu Gly Val Leu
    290                 295                 300

Ser Leu Leu Ala Thr Asn Gly Tyr Gln Leu Ala Arg Pro Ile Pro Arg
305                 310                 315                 320

Gln Leu Thr Asn Arg Trp Leu Ser Ser Phe Val Ser Gln Ile Met Ser
                325                 330                 335

Asp Gly Val Asn Glu Thr Pro Leu Trp Pro Gln Glu Arg Tyr Val Gln
            340                 345                 350

```
Ile Ala Tyr Asp Ser Pro Ser Val Asp Gly Ala Thr Gln Tyr Gly
            355                 360                 365
Tyr Val Arg Lys Asn Gln Leu Arg Leu Gly Met Arg Ile Ser Ala Leu
    370                 375                 380
Gln Ser Leu Ser Asp Thr Pro Ser Pro Val Gln Trp Leu Pro Gln Tyr
385                 390                 395                 400
Thr Ile Asp Gln Ala Ala Met Asp Glu Gly Asp Leu Met Val Ser Arg
                405                 410                 415
Leu Thr Gln Leu Pro Leu Arg Pro Asp Tyr Gly Asn Ile Trp Val Gly
            420                 425                 430
Asp Ala Leu Ser Tyr Tyr Val Asp Tyr Asn Arg Ser His Arg Val Val
            435                 440                 445
Leu Ser Ser Glu Leu Pro Gln Leu Pro Asp Thr Tyr Phe Asp Gly Asp
            450                 455                 460
Glu Gln Tyr Gly Arg Ser Leu Phe Ser Leu Ala Arg Lys Ile Gly Asp
465                 470                 475                 480
Arg Ser Leu Val Lys Asp Thr Ala Val Leu Lys His Ala Tyr Gln Ala
                485                 490                 495
Ile Asp Pro Asn Thr Gly Lys Glu Tyr Leu Arg Ser Arg Gln Ser Val
            500                 505                 510
Ala Tyr Phe Gly Ala Ser Ala Gly His Ser Gly Ala Asp Gln Pro Leu
            515                 520                 525
Val Ile Glu Pro Trp Ile Gln Gly Lys Ile Ser Gly Val Pro Pro Pro
            530                 535                 540
Ser Ser Val Arg Gln Phe Gly Tyr Asp Val Ala Arg Gly Ala Ile Val
545                 550                 555                 560
Asp Leu Ala Arg Pro Phe Pro Ser Gly Asp Tyr Gln Phe Val Tyr Ser
                565                 570                 575
Asp Val Asp Gln Val Val Asp Gly His Asp Asp Leu Ser Ile Ser Ser
            580                 585                 590
Gly Leu Val Glu Ser Leu Leu Ser Ser Cys Met His Ala Thr Ala Pro
            595                 600                 605
Gly Gly Ser Phe Val Val Lys Ile Asn Phe Pro Thr Arg Pro Val Trp
            610                 615                 620
His Tyr Ile Glu Gln Lys Ile Leu Pro Asn Ile Thr Ser Tyr Met Leu
625                 630                 635                 640
Ile Lys Pro Phe Val Thr Asn Asn Val Glu Leu Phe Phe Val Ala Phe
                645                 650                 655
Gly Val His Gln His Ser Ser Leu Thr Trp Thr Ser Gly Val Tyr Phe
            660                 665                 670
Phe Leu Val Asp His Phe Tyr Arg Tyr Glu Thr Leu Ser Thr Ile Ser
            675                 680                 685
Arg Gln Leu Pro Ser Phe Gly Tyr Val Asp Asp Gly Ser Ser Val Thr
            690                 695                 700
Gly Ile Glu Thr Ile Ser Ile Glu Asn Pro Gly Phe Ser Asn Met Thr
705                 710                 715                 720
Gln Ala Ala Arg Ile Gly Ile Ser Gly Leu Cys Ala Asn Val Gly Asn
                725                 730                 735
Ala Arg Lys Ser Ile Ala Ile Tyr Glu Ser His Gly Ala Arg Val Leu
            740                 745                 750
Thr Ile Thr Ser Arg Arg Ser Pro Ala Ser Ala Arg Arg Lys Ser Arg
            755                 760                 765
```

-continued

```
Leu Arg Tyr Leu Pro Leu Ile Asp Pro Arg Ser Leu Glu Val Gln Ala
770                 775                 780

Arg Thr Ile Leu Pro Ala Asp Pro Val Leu Phe Glu Asn Val Ser Gly
785                 790                 795                 800

Ala Ser Pro His Val Cys Leu Thr Met Met Tyr Asn Phe Glu Val Ser
            805                 810                 815

Ser Ala Val Tyr Asp Gly Asp Val Val Leu Asp Leu Gly Thr Gly Pro
            820                 825                 830

Glu Ala Lys Ile Leu Glu Leu Ile Pro Ala Thr Ser Pro Val Thr Cys
            835                 840                 845

Val Asp Ile Arg Pro Thr Ala Gln Pro Ser Gly Cys Trp Asn Val Arg
850                 855                 860

Thr Thr Phe Leu Glu Leu Asp Tyr Leu Ser Asp Gly Trp Ile Thr Gly
865                 870                 875                 880

Val Arg Gly Asp Ile Val Thr Cys Met Leu Ser Leu Gly Ala Ala Ala
            885                 890                 895

Ala Gly Lys Ser Met Thr Phe Asp Ala Ala Phe Gln Gln Leu Ile Lys
            900                 905                 910

Val Leu Ser Lys Ser Thr Ala Asn Val Val Leu Val Gln Val Asn Cys
            915                 920                 925

Pro Thr Asp Val Val Arg Ser Ile Lys Gly Tyr Leu Glu Ile Asp Ser
930                 935                 940

Thr Asn Lys Arg Tyr Arg Phe Pro Lys Phe Gly Arg Asp Glu Pro Tyr
945                 950                 955                 960

Ser Asp Met Asp Ala Leu Glu Lys Ile Cys Arg Thr Ala Trp Pro Asn
            965                 970                 975

Cys Ser Ile Thr Trp Val Pro Leu Ser Tyr Asp Leu Arg Trp Thr Arg
            980                 985                 990

Leu Ala Leu Leu Glu Ser Thr Thr Leu Ser Ser Ala Ser Ile Arg Ile
            995                 1000                1005

Ala Glu Leu Met Tyr Lys Tyr Met Pro Ile Met Arg Ile Asp Ile His
            1010                1015                1020

Gly Leu Pro Met Glu Lys Arg Gly Asn Phe Ile Val Gly Gln Asn Cys
1025                1030                1035                1040

Ser Leu Val Ile Pro Gly Phe Asn Ala Gln Asp Val Phe Asn Cys Tyr
            1045                1050                1055

Phe Asn Ser Ala Leu Ala Phe Ser Thr Glu Asp Val Asn Ala Ala Met
            1060                1065                1070

Ile Pro Gln Val Ser Ala Gln Phe Asp Ala Thr Lys Gly Glu Trp Thr
            1075                1080                1085

Leu Asp Met Val Phe Ser Asp Ala Gly Ile Tyr Thr Met Gln Ala Leu
            1090                1095                1100

Val Gly Ser Asn Ala Asn Pro Val Ser Leu Gly Ser Phe Val Val Asp
1105                1110                1115                1120

Ser Pro Asp Val Asp Ile Thr Asp Ala Trp Pro Ala Gln Leu Asp Phe
            1125                1130                1135

Thr Ile Ala Gly Thr Asp Val Asp Ile Thr Val Asn Pro Tyr Tyr Arg
            1140                1145                1150

Leu Met Thr Phe Val Arg Ile Asp Gly Gln Trp Gln Ile Ala Asn Pro
            1155                1160                1165

Asp Lys Phe Gln Phe Phe Ser Ser Ala Ser Gly Thr Leu Val Met Asn
            1170                1175                1180
```

```
Val Lys Leu Asp Ile Ala Asp Lys Tyr Leu Tyr Tyr Ile Arg Asp
1185                1190                1195                1200

Val Gln Ser Arg Asp Val Gly Phe Tyr Ile Gln His Pro Leu Gln Leu
                1205                1210                1215

Leu Asn Thr Ile Thr Leu Pro Thr Asn Glu Asp Leu Phe Leu Ser Ala
                1220                1225                1230

Pro Asp Met Arg Glu Trp Ala Val Lys Glu Ser Gly Asn Thr Ile Cys
                1235                1240                1245

Ile Leu Asn Ser Gln Gly Phe Val Leu Pro Gln Asp Trp Asp Val Leu
                1250                1255                1260

Thr Asp Thr Ile Ser Trp Ser Pro Ser Ile Pro Thr Tyr Ile Val Pro
1265                1270                1275                1280

Pro Gly Asp Tyr Thr Leu Thr Pro Leu
                1285

<210> SEQ ID NO 21
<211> LENGTH: 1275
<212> TYPE: PRT
<213> ORGANISM: Reovirus

<400> SEQUENCE: 21

Met Lys Arg Ile Pro Arg Lys Thr Lys Gly Lys Ser Ser Gly Lys Gly
1               5                   10                  15

Asn Asp Ser Thr Glu Arg Ala Asp Gly Ser Ser Gln Leu Arg Asp
                20                  25                  30

Lys Gln Asn Asn Lys Ala Gly Pro Ala Thr Thr Glu Pro Gly Thr Ser
                35                  40                  45

Asn Arg Glu Gln Tyr Lys Ala Arg Pro Gly Ile Ala Ser Val Gln Arg
50                  55                  60

Ala Thr Glu Ser Ala Glu Met Pro Met Lys Asn Asn Asp Glu Gly Thr
65                  70                  75                  80

Pro Asp Lys Lys Gly Asn Thr Lys Gly Asp Leu Val Asn Glu His Ser
                85                  90                  95

Glu Ala Lys Asp Glu Ala Asp Glu Ala Thr Lys Lys Gln Ala Lys Asp
                100                 105                 110

Thr Asp Lys Ser Lys Ala Gln Val Thr Tyr Ser Asp Thr Gly Ile Asn
                115                 120                 125

Asn Ala Asn Glu Leu Ser Arg Ser Gly Asn Val Asp Asn Glu Gly Gly
                130                 135                 140

Ser Asn Gln Lys Pro Met Ser Thr Arg Ile Ala Glu Ala Thr Ser Ala
145                 150                 155                 160

Ile Val Ser Lys His Pro Ala Arg Val Gly Leu Pro Pro Thr Ala Ser
                165                 170                 175

Ser Gly His Gly Tyr Gln Cys His Val Cys Ser Ala Val Leu Phe Ser
                180                 185                 190

Pro Leu Asp Leu Asp Ala His Val Ala Ser His Gly Leu His Gly Asn
                195                 200                 205

Met Thr Leu Thr Ser Ser Asp Ile Gln Arg His Ile Thr Glu Phe Ile
                210                 215                 220

Ser Ser Trp Gln Asn His Pro Ile Val Gln Val Ser Ala Asp Val Glu
225                 230                 235                 240

Asn Lys Lys Thr Ala Gln Leu Leu His Ala Asp Thr Pro Arg Leu Val
                245                 250                 255

Thr Trp Asp Ala Gly Leu Cys Thr Ser Phe Lys Ile Val Pro Ile Val
                260                 265                 270
```

-continued

Pro Ala Gln Val Pro Gln Asp Val Leu Ala Tyr Thr Phe Thr Ser
            275                 280                 285

Ser Tyr Ala Ile Gln Ser Pro Phe Pro Glu Ala Val Ser Arg Ile
    290                 295                 300

Val Val His Thr Arg Trp Ala Ser Asn Val Asp Phe Asp Arg Asp Ser
305                 310                 315                 320

Ser Val Ile Met Ala Pro Thr Glu Asn Asn Ile His Leu Phe Lys
                325                 330                 335

Gln Leu Leu Asn Thr Glu Thr Leu Ser Val Arg Gly Ala Asn Pro Leu
            340                 345                 350

Met Phe Arg Ala Asn Val Leu His Met Leu Leu Glu Phe Val Leu Asp
            355                 360                 365

Asn Leu Tyr Leu Asn Arg His Thr Gly Phe Ser Gln Asp His Thr Pro
    370                 375                 380

Phe Thr Glu Gly Ala Asn Leu Arg Ser Leu Pro Gly Pro Asp Ala Glu
385                 390                 395                 400

Lys Trp Tyr Ser Ile Met Tyr Pro Thr Arg Met Gly Thr Pro Asn Val
                405                 410                 415

Ser Lys Ile Cys Asn Phe Val Ala Ser Cys Val Arg Asn Arg Val Gly
                420                 425                 430

Arg Phe Asp Arg Ala Gln Met Met Asn Gly Ala Met Ser Glu Trp Val
    435                 440                 445

Asp Val Phe Glu Thr Ser Asp Ala Leu Thr Val Ser Ile Arg Gly Arg
    450                 455                 460

Trp Met Ala Arg Leu Ala Arg Met Asn Ile Asn Pro Thr Glu Ile Glu
465                 470                 475                 480

Trp Ala Leu Thr Glu Cys Ala Gln Gly Tyr Val Thr Val Thr Ser Pro
                485                 490                 495

Tyr Ala Pro Ser Val Asn Arg Leu Met Pro Tyr Arg Ile Ser Asn Ala
                500                 505                 510

Glu Arg Gln Ile Ser Gln Ile Ile Arg Ile Met Asn Ile Gly Asn Asn
    515                 520                 525

Ala Thr Val Ile Gln Pro Val Leu Gln Asp Ile Ser Val Leu Leu Gln
    530                 535                 540

Arg Ile Ser Pro Leu Gln Ile Asp Pro Thr Ile Ile Ser Asn Thr Met
545                 550                 555                 560

Ser Thr Val Ser Glu Ser Thr Thr Gln Thr Leu Ser Pro Ala Ser Ser
                565                 570                 575

Ile Leu Gly Lys Leu Arg Pro Ser Asn Ser Asp Phe Ser Ser Phe Arg
                580                 585                 590

Val Ala Leu Ala Gly Trp Leu Tyr Asn Gly Val Val Thr Thr Val Ile
            595                 600                 605

Asp Asp Ser Ser Tyr Pro Lys Asp Gly Gly Ser Val Thr Ser Leu Glu
    610                 615                 620

Asn Leu Trp Asp Phe Phe Ile Leu Ala Leu Ala Leu Pro Leu Thr Thr
625                 630                 635                 640

Asp Pro Cys Ala Pro Val Lys Ala Phe Met Thr Leu Ala Asn Met Met
                645                 650                 655

Val Gly Phe Glu Thr Ile Pro Met Asp Asn Gln Ile Tyr Thr Gln Ser
                660                 665                 670

Arg Arg Ala Ser Ala Phe Ser Thr Pro His Thr Trp Pro Arg Cys Phe
    675                 680                 685

```
Met Asn Ile Gln Leu Ile Ser Pro Ile Asp Ala Pro Ile Leu Arg Gln
690                 695                 700

Trp Ala Glu Ile Ile His Arg Tyr Trp Pro Asn Pro Ser Gln Ile Arg
705                 710                 715                 720

Tyr Gly Ala Pro Asn Val Phe Gly Ser Ala Asn Leu Phe Thr Pro Pro
                725                 730                 735

Glu Val Leu Leu Leu Pro Ile Asp His Gln Pro Ala Asn Val Thr Thr
                740                 745                 750

Pro Thr Leu Asp Phe Thr Asn Glu Leu Thr Asn Trp Arg Ala Arg Val
                755                 760                 765

Cys Glu Leu Met Lys Asn Leu Val Asp Asn Gln Arg Tyr Gln Pro Gly
770                 775                 780

Trp Thr Gln Ser Leu Val Ser Ser Met Arg Gly Thr Leu Asp Lys Leu
785                 790                 795                 800

Lys Leu Ile Lys Ser Met Thr Pro Met Tyr Leu Gln Gln Leu Ala Pro
                805                 810                 815

Val Glu Leu Ala Val Ile Ala Pro Met Leu Pro Phe Pro Pro Phe Gln
                820                 825                 830

Val Pro Tyr Val Arg Leu Asp Arg Asp Arg Val Pro Thr Met Val Gly
                835                 840                 845

Val Thr Arg His Ser Arg Asp Thr Ile Thr Gln Pro Ala Leu Ser Leu
850                 855                 860

Ser Thr Thr Asn Thr Thr Val Gly Val Pro Leu Ala Leu Asp Ala Arg
865                 870                 875                 880

Ala Ile Thr Val Ala Leu Leu Ser Gly Lys Tyr Pro Pro Asp Leu Val
                885                 890                 895

Thr Asn Val Trp Tyr Ala Asp Ala Ile Tyr Pro Met Tyr Ala Asp Thr
                900                 905                 910

Glu Val Phe Ser Asn Leu Gln Arg Asp Met Ile Thr Cys Glu Ala Val
                915                 920                 925

Gln Thr Leu Val Thr Leu Val Ala Gln Ile Ser Glu Thr Gln Tyr Pro
930                 935                 940

Val Asp Arg Tyr Leu Asp Trp Ile Pro Ser Leu Arg Ala Ser Ala Ala
945                 950                 955                 960

Thr Ala Ala Thr Phe Ala Glu Trp Val Asn Thr Ser Met Lys Thr Ala
                965                 970                 975

Phe Asp Leu Ser Asp Met Leu Leu Glu Pro Leu Leu Ser Gly Asp Pro
                980                 985                 990

Arg Met Thr Gln Leu Ala Ile Gln Tyr Gln Gln Tyr Asn Gly Arg Thr
                995                 1000                1005

Phe Asn Ile Ile Pro Glu Met Pro Gly Ser Val Ile Ala Asp Cys Val
                1010                1015                1020

Gln Leu Thr Ala Glu Val Phe Asn His Glu Tyr Asn Leu Phe Gly Ile
1025                1030                1035                1040

Ala Arg Gly Asp Ile Ile Gly Arg Val Gln Ser Thr His Leu Trp
                1045                1050                1055

Ser Pro Leu Ala Pro Pro Asp Leu Val Phe Asp Arg Asp Thr Pro
                1060                1065                1070

Gly Val His Ile Phe Gly Arg Asp Cys Arg Ile Ser Phe Gly Met Asn
                1075                1080                1085

Gly Ala Ala Pro Met Ile Arg Asp Glu Thr Gly Leu Met Val Pro Phe
                1090                1095                1100
```

```
Glu Gly Asn Trp Ile Phe Pro Leu Ala Leu Trp Gln Met Asn Thr Arg
        1105                1110                1115                1120

Tyr Phe Asn Gln Gln Phe Asp Ala Trp Ile Lys Thr Gly Glu Leu Arg
            1125                1130                1135

Ile Arg Ile Glu Met Gly Ala Tyr Pro Tyr Met Leu His Tyr Tyr Asp
            1140                1145                1150

Pro Arg Gln Tyr Ala Asn Ala Trp Asn Leu Thr Ser Ala Trp Leu Glu
        1155                1160                1165

Glu Ile Thr Pro Thr Ser Ile Pro Ser Val Pro Phe Met Val Pro Ile
        1170                1175                1180

Ser Ser Asp His Asp Ile Ser Ser Ala Pro Ala Val Gln Tyr Ile Ile
1185                1190                1195                1200

Ser Thr Glu Tyr Asn Asp Arg Ser Leu Phe Cys Thr Asn Ser Ser Ser
            1205                1210                1215

Pro Gln Thr Ile Ala Gly Pro Asp Lys His Ile Pro Val Glu Arg Tyr
            1220                1225                1230

Asn Ile Leu Thr Asn Pro Asp Ala Pro Pro Thr Gln Ile Gln Leu Pro
        1235                1240                1245

Glu Val Val Asp Leu Tyr Asn Val Val Thr Arg Tyr Ala Tyr Glu Thr
        1250                1255                1260

Pro Pro Ile Thr Ala Val Val Met Gly Val Pro
1265                1270                1275

<210> SEQ ID NO 22
<211> LENGTH: 3854
<212> TYPE: DNA
<213> ORGANISM: Reovirus

<400> SEQUENCE: 22
gctacacgtt ccacgacaat gtcatccatg atactgactc agtttggacc gttcattgag      60
agcatttcag gtatcactga tcaatcgaat gacgtgtttg aagatgcagc aaaagcattc     120
tctatgttta ctcgcagcga tgtctacaag gcgctggatg aaataccttt ctctgatgat     180
gcgatgcttc caatccctcc aactatatat acgaaaccat ctcacgattc atattattac     240
attgatgctc taaccgtgt gcgtcgcaaa acatatcagg gccctgatga cgtgtacgta     300
cctaattgtt ctattgttga attgctggag ccacatgaga ctctgacatc ttatgggcgg     360
ttgtccgagg ccatcgagaa tcgtgccaag gatggggaca gccaagccag aatcgccaca     420
acgtatggta gaatcgctga atctcaagct cgacagatta aggctccatt ggagaagttt     480
gtgttggcac tattagtggc cgaagcaggg gggtctttat atgatccagt tttgcagaag     540
tatgatgaga ttccagatct atcgcataat tgcccttat ggtgttttag agagatctgt     600
cgtcacatat ctggtccatt accagatcgg gcaccttatc tttacttatc tgcagggta     660 ttctggttaa tgtcaccacg aatgacgtct gcaatccctc cgctactatc cgatcttgtt     720
aatttagcta ttttgcaaca aactgcgggt ttagatccat cattagtgaa attgggagta     780
cagatatgcc ttcatgcagc agctagctca agttattcat ggtttatctt aaagactaag     840
tctatttttc ctcaaaacac gttgcacagt atgtatgaat ctctagaagg gggatactgt     900
cctaatcttg aatggttaga gcctagatca gactataagt tcatgtacat gggagtcatg     960
ccattgtccg ctaagtatgc taggtcggcg ccgtccaatg ataagaaagc gcgggaactt    1020
ggcgagaaat atggactgag ctcagtcgtc ggtgagcttc gtaaacggac aaagacgtat    1080
gttaaacatg actttgcttc agtgaggtac attcgtgacg ctatggcatg tactagcggt    1140
```

```
attttcttgg taagaacacc caccgaaacg gtattgcaag aatatacgca gagtccggag   1200
attaaggttc ccattcccca gaaagactgg acaggcccaa taggtgaaat cagaattcta   1260
aaagatacaa caagttccat cgcgcgttac ttatatagaa catggtactt ggcagcggcg   1320
agaatggcgg ctcaaccacg tacgtgggat ccattgtttc aagcgattat gagatctcaa   1380
tacgtgacag ctaggggtgg atctggcgca gcactccgcg aatctttgta tgcaatcaat   1440
gtgtcgttac ctgatttcaa gggcttacca gtgaaggcag caactaagat attccaggcg   1500
gcacaattag cgaacttgcc gttctcccac acatcagtgg ctatactagc tgacacttca   1560
atgggattgc gaaatcaggt gcagaggcgg ccacgatcca ttatgccatt aaatgtgccc   1620
cagcagcagg tttcggcgcc ccatacattg acagcggatt acattaacta ccacatgaat   1680
ctatcaccca cgtctggtag tgcggtcatt gagaaggtga ttcctttagg tgtatacgct   1740
tcgagccctc ctaaccagtc gatcaacatt gacatatctg cgtgtgacgc tagtattact   1800
tgggatttct ttctgtcagt gattatggcg gctatacacg aaggtgtcgc tagtagctcc   1860
attggaaaac catttatggg ggttcctgca tccattgtaa atgatgagtc tgtcgttgga   1920
gtgagagctg ctaggccgat atcgggaatg cagaacatga ttcagcatct atcgaaacta   1980
tataaacgtg gattttcata tagagtaaac gattctttt ctccaggtaa cgatttact   2040 catatgacta ccactttccc gtcaggttca acagccacct ctactgagca tactgctaat   2100
aatagtacga tgatgaaaac tttcctgaca gtatggggac ccgaacatac tgacgaccct   2160
gacgtcttac gtttaatgaa gtctttaact attcaaagga attacgtatg tcaaggtgat   2220
gatggattaa tgattatcga tgggactact gctggtaagg tgaacagtga aactattcag   2280
aacgatctag aattaatctc aaaatatggt gaggaattcg gatggaaata tgacatagcg   2340
tacgatggga ctgccgaata cttaaagcta tacttcatat ttggctgtcg aattccaaat   2400
cttagtcgcc atccaatcgt ggggaaagaa cgggcgaatt cttcagcaga ggagccatgg   2460
ccagcaattc tagatcagat tatgggtgtc ttctttaatg tgttcatga tgggttacag   2520 tggcagcggt ggatacgtta ttcatgggct ctatgctgtg ctttctcacg tcaaagaaca   2580
atgattggtg agagcgtggg ttaccttcaa tatcctatgt ggtcttttgt ctactgggga   2640
ttaccactgg ttaaagcgtt tgggtcagac ccatggatat tttcttggta catgcctact   2700
ggagatctgg gaatgtatag ttggattagc ttgatacgcc ctctgatgac aagatggatg   2760
gtggctaatg gttacgtaac tgacagatgc tcaaccgtat tcgggaacgc agattatcgc   2820
aggtgtttca atgaacttaa actatatcaa ggttattata tggcacaatt gcccaggaat   2880
cctaagaagt ctggacgagc ggcctctcgg gaggtaagag aacaattcac tcaggcatta   2940
tccgactatc taatgcaaaa tccagagctg aagtcacgtg tgctacgtgg tcgtagtgag   3000
tgggagaaat atggagcggg gataattcac aatcctccgt cattattcga tgtgccccat   3060
aaatggtatc agggtgcgca agaggcagca atcgctacga gaagagct ggcagaaatg   3120 gatgagacat taatgcgcgc tcgaaggcac agctattcga gcttttcaaa gttattagag   3180
gcgtatctgc tcgtgaaatg gcgaatgtgc gaggcccgcg aaccgtcggt tgatttgcga   3240
ttaccattat gtgcgggtat tgacccatta aactcagatc ctttctcaa gatggtaagc   3300 gttggaccaa tgctccagag tacgagaaag tactttgctc agacactatt catggcaaag   3360
acggtgtcgg tcttgacgt taacgcgatt gatagcgcgt tattacgact gcgaacatta   3420
ggtgctgata agaaagcatt aacggcgcag ttattaatgg tggggcttca ggagtcagaa   3480
gcggacgcat tggccgggaa gataatgcta caggatgtga atactgtgca attagccaga   3540
```

-continued

```
gtggttaact tagctgtgcc agatacttgg atgtcgttag actttgactc tatgttcaaa    3600
caccacgtca agctgcttcc caaagatgga cgtcatctaa atactgatat tcctcctcga    3660
atgggatggt tacgggccat tttacgattc ttaggtgccg aatggtaat gactgcgact     3720 ggagttgctg tcgacatcta tctggaggat atacatggcg gtggtcggtc acttggacag    3780
agattcatga cttggatgcg acaggaagga cggtcagcgt gagtctacca tgggtcgtgg    3840
tgcgtcaact catc                                                      3854
```

<210> SEQ ID NO 23
<211> LENGTH: 1267
<212> TYPE: PRT
<213> ORGANISM: Reovirus

<400> SEQUENCE: 23

```
Met Ser Ser Met Ile Leu Thr Gln Phe Gly Pro Phe Ile Glu Ser Ile
1               5                   10                  15

Ser Gly Ile Thr Asp Gln Ser Asn Asp Val Phe Glu Asp Ala Ala Lys
            20                  25                  30

Ala Phe Ser Met Phe Thr Arg Ser Asp Val Tyr Lys Ala Leu Asp Glu
        35                  40                  45

Ile Pro Phe Ser Asp Asp Ala Met Leu Pro Ile Pro Thr Ile Tyr
    50                  55                  60

Thr Lys Pro Ser His Asp Ser Tyr Tyr Ile Asp Ala Leu Asn Arg
65                  70                  75                  80

Val Arg Arg Lys Thr Tyr Gln Gly Pro Asp Asp Val Tyr Val Pro Asn
                85                  90                  95

Cys Ser Ile Val Glu Leu Leu Glu Pro His Glu Thr Leu Thr Ser Tyr
            100                 105                 110

Gly Arg Leu Ser Glu Ala Ile Glu Asn Arg Ala Lys Asp Gly Asp Ser
        115                 120                 125

Gln Ala Arg Ile Ala Thr Thr Tyr Gly Arg Ile Ala Glu Ser Gln Ala
    130                 135                 140

Arg Gln Ile Lys Ala Pro Leu Glu Lys Phe Val Leu Ala Leu Leu Val
145                 150                 155                 160

Ala Glu Ala Gly Gly Ser Leu Tyr Asp Pro Val Leu Gln Lys Tyr Asp
                165                 170                 175

Glu Ile Pro Asp Leu Ser His Asn Cys Pro Leu Trp Cys Phe Arg Glu
            180                 185                 190

Ile Cys Arg His Ile Ser Gly Pro Leu Pro Asp Arg Ala Pro Tyr Leu
        195                 200                 205

Tyr Leu Ser Ala Gly Val Phe Trp Leu Met Ser Pro Arg Met Thr Ser
    210                 215                 220

Ala Ile Pro Pro Leu Leu Ser Asp Leu Val Asn Leu Ala Ile Leu Gln
225                 230                 235                 240

Gln Thr Ala Gly Leu Asp Pro Ser Leu Val Lys Leu Gly Val Gln Ile
                245                 250                 255

Cys Leu His Ala Ala Ser Ser Tyr Ser Trp Phe Ile Leu Lys
            260                 265                 270

Thr Lys Ser Ile Phe Pro Gln Asn Thr Leu His Ser Met Tyr Glu Ser
        275                 280                 285

Leu Glu Gly Gly Tyr Cys Pro Asn Leu Glu Trp Leu Glu Pro Arg Ser
    290                 295                 300

Asp Tyr Lys Phe Met Tyr Met Gly Val Met Pro Leu Ser Ala Lys Tyr
305                 310                 315                 320
```

-continued

```
Ala Arg Ser Ala Pro Ser Asn Asp Lys Lys Ala Arg Glu Leu Gly Glu
                325                 330                 335
Lys Tyr Gly Leu Ser Ser Val Val Gly Glu Leu Arg Lys Arg Thr Lys
            340                 345                 350
Thr Tyr Val Lys His Asp Phe Ala Ser Val Arg Tyr Ile Arg Asp Ala
        355                 360                 365
Met Ala Cys Thr Ser Gly Ile Phe Leu Val Arg Thr Pro Thr Glu Thr
    370                 375                 380
Val Leu Gln Glu Tyr Thr Gln Ser Pro Glu Ile Lys Val Pro Ile Pro
385                 390                 395                 400
Gln Lys Asp Trp Thr Gly Pro Ile Gly Glu Ile Arg Ile Leu Lys Asp
                405                 410                 415
Thr Thr Ser Ser Ile Ala Arg Tyr Leu Tyr Arg Thr Trp Tyr Leu Ala
            420                 425                 430
Ala Ala Arg Met Ala Ala Gln Pro Arg Thr Trp Asp Pro Leu Phe Gln
        435                 440                 445
Ala Ile Met Arg Ser Gln Tyr Val Thr Ala Arg Gly Gly Ser Gly Ala
    450                 455                 460
Ala Leu Arg Glu Ser Leu Tyr Ala Ile Asn Val Ser Leu Pro Asp Phe
465                 470                 475                 480
Lys Gly Leu Pro Val Lys Ala Ala Thr Lys Ile Phe Gln Ala Ala Gln
                485                 490                 495
Leu Ala Asn Leu Pro Phe Ser His Thr Ser Val Ala Ile Leu Ala Asp
            500                 505                 510
Thr Ser Met Gly Leu Arg Asn Gln Val Gln Arg Arg Pro Arg Ser Ile
        515                 520                 525
Met Pro Leu Asn Val Pro Gln Gln Val Ser Ala Pro His Thr Leu
    530                 535                 540
Thr Ala Asp Tyr Ile Asn Tyr His Met Asn Leu Ser Pro Thr Ser Gly
545                 550                 555                 560
Ser Ala Val Ile Glu Lys Val Ile Pro Leu Gly Val Tyr Ala Ser Ser
                565                 570                 575
Pro Pro Asn Gln Ser Ile Asn Ile Asp Ile Ser Ala Cys Asp Ala Ser
            580                 585                 590
Ile Thr Trp Asp Phe Phe Leu Ser Val Ile Met Ala Ala Ile His Glu
        595                 600                 605
Gly Val Ala Ser Ser Ile Gly Lys Pro Phe Met Gly Val Pro Ala
    610                 615                 620
Ser Ile Val Asn Asp Glu Ser Val Val Gly Val Arg Ala Ala Arg Pro
625                 630                 635                 640
Ile Ser Gly Met Gln Asn Met Ile Gln His Leu Ser Lys Leu Tyr Lys
                645                 650                 655
Arg Gly Phe Ser Tyr Arg Val Asn Asp Ser Phe Ser Pro Gly Asn Asp
            660                 665                 670
Phe Thr His Met Thr Thr Thr Phe Pro Ser Gly Ser Thr Ala Thr Ser
        675                 680                 685
Thr Glu His Thr Ala Asn Asn Ser Thr Met Met Glu Thr Phe Leu Thr
    690                 695                 700
Val Trp Gly Pro Glu His Thr Asp Asp Pro Asp Val Leu Arg Leu Met
705                 710                 715                 720
Lys Ser Leu Thr Ile Gln Arg Asn Tyr Val Cys Gln Gly Asp Asp Gly
                725                 730                 735
```

-continued

Leu Met Ile Ile Asp Gly Thr Thr Ala Gly Lys Val Asn Ser Glu Thr
            740                 745                 750

Ile Gln Asn Asp Leu Glu Leu Ile Ser Lys Tyr Gly Glu Glu Phe Gly
            755                 760                 765

Trp Lys Tyr Asp Ile Ala Tyr Asp Gly Thr Ala Glu Tyr Leu Lys Leu
        770                 775                 780

Tyr Phe Ile Phe Gly Cys Arg Ile Pro Asn Leu Ser Arg His Pro Ile
785                 790                 795                 800

Val Gly Lys Glu Arg Ala Asn Ser Ser Ala Glu Glu Pro Trp Pro Ala
                805                 810                 815

Ile Leu Asp Gln Ile Met Gly Val Phe Phe Asn Gly Val His Asp Gly
            820                 825                 830

Leu Gln Trp Gln Arg Trp Ile Arg Tyr Ser Trp Ala Leu Cys Cys Ala
            835                 840                 845

Phe Ser Arg Gln Arg Thr Met Ile Gly Glu Ser Val Gly Tyr Leu Gln
850                 855                 860

Tyr Pro Met Trp Ser Phe Val Tyr Trp Gly Leu Pro Leu Val Lys Ala
865                 870                 875                 880

Phe Gly Ser Asp Pro Trp Ile Phe Ser Trp Tyr Met Pro Thr Gly Asp
                885                 890                 895

Leu Gly Met Tyr Ser Trp Ile Ser Leu Ile Arg Pro Leu Met Thr Arg
            900                 905                 910

Trp Met Val Ala Asn Gly Tyr Val Thr Asp Arg Cys Ser Thr Val Phe
            915                 920                 925

Gly Asn Ala Asp Tyr Arg Arg Cys Phe Asn Glu Leu Lys Leu Tyr Gln
            930                 935                 940

Gly Tyr Tyr Met Ala Gln Leu Pro Arg Asn Pro Lys Lys Ser Gly Arg
945                 950                 955                 960

Ala Ala Ser Arg Glu Val Arg Glu Gln Phe Thr Gln Ala Leu Ser Asp
                965                 970                 975

Tyr Leu Met Gln Asn Pro Glu Leu Lys Ser Arg Val Leu Arg Gly Arg
            980                 985                 990

Ser Glu Trp Glu Lys Tyr Gly Ala Gly Ile Ile His Asn Pro Pro Ser
            995                 1000                1005

Leu Phe Asp Val Pro His Lys Trp Tyr Gln Gly Ala Gln Glu Ala Ala
        1010                1015                1020

Ile Ala Thr Arg Glu Glu Leu Ala Glu Met Asp Glu Thr Leu Met Arg
1025                1030                1035                1040

Ala Arg Arg His Ser Tyr Ser Ser Phe Ser Lys Leu Leu Glu Ala Tyr
                1045                1050                1055

Leu Leu Val Lys Trp Arg Met Cys Glu Ala Arg Glu Pro Ser Val Asp
            1060                1065                1070

Leu Arg Leu Pro Leu Cys Ala Gly Ile Asp Pro Leu Asn Ser Asp Pro
        1075                1080                1085

Phe Leu Lys Met Val Ser Val Gly Pro Met Leu Gln Ser Thr Arg Lys
    1090                1095                1100

Tyr Phe Ala Gln Thr Leu Phe Met Ala Lys Thr Val Ser Gly Leu Asp
1105                1110                1115                1120

Val Asn Ala Ile Asp Ser Ala Leu Leu Arg Leu Arg Thr Leu Gly Ala
                1125                1130                1135

Asp Lys Lys Ala Leu Thr Ala Gln Leu Leu Met Val Gly Leu Gln Glu
            1140                1145                1150

Ser Glu Ala Asp Ala Leu Ala Gly Lys Ile Met Leu Gln Asp Val Asn
1155                1160                1165

Thr Val Gln Leu Ala Arg Val Val Asn Leu Ala Val Pro Asp Thr Trp
    1170                1175                1180

Met Ser Leu Asp Phe Asp Ser Met Phe Lys His His Val Lys Leu Leu
1185                1190                1195                1200

Pro Lys Asp Gly Arg His Leu Asn Thr Asp Ile Pro Pro Arg Met Gly
                1205                1210                1215

Trp Leu Arg Ala Ile Leu Arg Phe Leu Gly Ala Gly Met Val Met Thr
            1220                1225                1230

Ala Thr Gly Val Ala Val Asp Ile Tyr Leu Glu Asp Ile His Gly Gly
        1235                1240                1245

Gly Arg Ser Leu Gly Gln Arg Phe Met Thr Trp Met Arg Gln Glu Gly
    1250                1255                1260

Arg Ser Ala
1265

<210> SEQ ID NO 24
<211> LENGTH: 1196
<212> TYPE: DNA
<213> ORGANISM: Reovirus

<400> SEQUENCE: 24 gctattttg cctcttccca gacgttgtcg caatggaggt gtgcttgccc aacggtcatc      60
aggtcgtgga cttgattaac aacgcttttg aaggtcgtgt atcaatctac agcgcgcaag    120
agggatggga caaaacaatc tcagcacagc cagatatgat ggtatgtggt ggcgccgtcg    180
tttgcatgca ttgtctaggt gttgttggat ctctacaacg caagctgaag catttgcctc    240
accatagatg taatcaacag atccgtcatc aggattacgt cgatgtacag ttcgcagacc    300
gtgttactgc tcactggaag cggggtatgc tgtccttcgt tgcgcagatg cacgagatga    360
tgaatgacgt gtcgccagat gacctggatc gtgtgcgtac tgagggaggt tcactagtgg    420
agctgaaccg gcttcaggtt gacccaaatt caatgtttag atcaatacac tcaagttgga    480
cagatccttt gcaggtggtg gacgaccttg acactaagct ggatcagtac tggacagcct    540
taaacctgat gatcgactca tccgacttga tacccaactt tatgatgaga gacccatcac    600
acgcgttcaa tggtgtgaaa ctggaggag atgctcgtca aacccaattc tccaggactt    660
ttgattcgag atcgagtttg aatggggtg tgatggttta tgattactct gagctggagc    720
atgatccatc gaagggccgt gcttacagaa aggaattggt gacgccagct cgagatttcg    780
gtcactttgg attatcccat tattctaggg cgactacccc aatccttgga agatgccgg    840 ccgtattctc aggaatgttg actgggaact gtaaaatgta tccattcatt aaaggaacgg    900
ctaagctgaa gacagtgcgc aagctagtgg aggcagtcaa tcatgcttgg ggtgtcgaga    960
agattagata tgctcttggg ccaggtggca tgacgggatg gtacaatagg actatgcaac   1020 aggccccat tgtgctaact cctgctgctc tcacaatgtt cccagatacc atcaagtttg   1080
gggatttgaa ttatccagtg atgattggcg atccgatgat tcttggctaa cacccccat   1140 cttcacagcg ccgggcttga ccaacctggt gtgacgtggg acaggcttca ttcatc       1196

<210> SEQ ID NO 25
<211> LENGTH: 365
<212> TYPE: PRT
<213> ORGANISM: Reovirus

<400> SEQUENCE: 25

```
Met Glu Val Cys Leu Pro Asn Gly His Gln Val Val Asp Leu Ile Asn
1               5                   10                  15

Asn Ala Phe Glu Gly Arg Val Ser Ile Tyr Ser Ala Gln Glu Gly Trp
            20                  25                  30

Asp Lys Thr Ile Ser Ala Gln Pro Asp Met Met Val Cys Gly Gly Ala
        35                  40                  45

Val Val Cys Met His Cys Leu Gly Val Val Gly Ser Leu Gln Arg Lys
    50                  55                  60

Leu Lys His Leu Pro His His Arg Cys Asn Gln Gln Ile Arg His Gln
65                  70                  75                  80

Asp Tyr Val Asp Val Gln Phe Ala Asp Arg Val Thr Ala His Trp Lys
                85                  90                  95

Arg Gly Met Leu Ser Phe Val Ala Gln Met His Glu Met Met Asn Asp
            100                 105                 110

Val Ser Pro Asp Asp Leu Asp Arg Val Arg Thr Glu Gly Gly Ser Leu
        115                 120                 125

Val Glu Leu Asn Arg Leu Gln Val Asp Pro Asn Ser Met Phe Arg Ser
    130                 135                 140

Ile His Ser Ser Trp Thr Asp Pro Leu Gln Val Val Asp Asp Leu Asp
145                 150                 155                 160

Thr Lys Leu Asp Gln Tyr Trp Thr Ala Leu Asn Leu Met Ile Asp Ser
                165                 170                 175

Ser Asp Leu Ile Pro Asn Phe Met Met Arg Asp Pro Ser His Ala Phe
            180                 185                 190

Asn Gly Val Lys Leu Glu Gly Asp Ala Arg Gln Thr Gln Phe Ser Arg
        195                 200                 205

Thr Phe Asp Ser Arg Ser Ser Leu Glu Trp Gly Val Met Val Tyr Asp
    210                 215                 220

Tyr Ser Glu Leu Glu His Asp Pro Ser Lys Gly Arg Ala Tyr Arg Lys
225                 230                 235                 240

Glu Leu Val Thr Pro Ala Arg Asp Phe Gly His Phe Gly Leu Ser His
                245                 250                 255

Tyr Ser Arg Ala Thr Thr Pro Ile Leu Gly Lys Met Pro Ala Val Phe
            260                 265                 270

Ser Gly Met Leu Thr Gly Asn Cys Lys Met Tyr Pro Phe Ile Lys Gly
        275                 280                 285

Thr Ala Lys Leu Lys Thr Val Arg Lys Leu Val Glu Ala Val Asn His
    290                 295                 300

Ala Trp Gly Val Glu Lys Ile Arg Tyr Ala Leu Gly Pro Gly Gly Met
305                 310                 315                 320

Thr Gly Trp Tyr Asn Arg Thr Met Gln Gln Ala Pro Ile Val Leu Thr
                325                 330                 335

Pro Ala Ala Leu Thr Met Phe Pro Asp Thr Ile Lys Phe Gly Asp Leu
            340                 345                 350

Asn Tyr Pro Val Met Ile Gly Asp Pro Met Ile Leu Gly
        355                 360                 365

<210> SEQ ID NO 26
<211> LENGTH: 2203
<212> TYPE: DNA
<213> ORGANISM: Reovirus
```

<400> SEQUENCE: 26

```
gctaatctgc tgaccgttac tctgcaaaga tggggaacgc ttcctctatc gttcagacga      60
tcaacgtcac tggagatggc aatgtattta accatcagct gaaacttca tctaccgctg     120
taccatcgtt aagcttatca cctggaatgc tgaatcccgg aggggtacca tggattgctg    180
ttggagatga acatctgtg acttcaccag gcgcattacg tcgaatgacg tcaaaggaca     240
tcccggaaac ggcaataatc aacacagaca attcatcagg cgccgtgcca agcgaatcag    300
cgcttgtgcc ctacatcgat gagccgctgg tagtggttac agagcatgct attaccaact    360
tcaccaaagc tgagatggca cttgaattca atcgtgagtt ccttgacaag atgcgtgtgc    420
tgtcagtgtc accaaaatat tcggatcttc tgacctatgt tgactgctac gtcggtgtgt    480
ctgctcgtca ggctttaaac aattttcaga acaagtgcc tgtgattaca cctactaggc     540
agacgatgta tgtcgactcg atacaagcgg ccttgaaagc tttagaaaag tgggagattg    600
atctgagagt ggctcaaacg ttgctgccta cgaacgttcc gattggagaa gtctcttgtc    660
caatgcagtc ggtagtgaaa ctgctggatg atcagctgcc agatgacacg ctgatacgga    720
ggtatcccaa ggaagccgcc gtcgctttgg ctaaacgaaa cggggaata caatggatgg     780
acgtatcaga aggcaccgtg atgaacgagg ctgtcaacgc tgttgcagct agtgcactgg    840
caccttcagc atcagcccca cccttagaag agaagtcaaa gttaaccgaa caagcgatgg    900
atctcgtgac cgcggctgag cctgagataa ttgcctcact cgcgccagtt cccgcacccg    960
tgtttgccat accacctaaa ccagcagatt ataatgtgcg tactctgagg atcgacgagg   1020
ccacttggct gcgaatgatt ccaaaatcaa tgaacacacc ttttcaaatc caggtgactg    1080
ataacacagg aactaattgg catctcaatt tgagggggg gactcgtgta gtgaatctgg    1140
accaaatcgc tccgatgcgg tttgtattag atttaggggg aaagagttat aaagagacga    1200
gctgggatcc aaacggcaag aaggtcggat tcatcgtttt tcaatcgaag ataccattcg    1260
aactttggac tgctgcttca cagatcggtc aagccacggt ggttaactat gtccaactat    1320
acgctgaaga cagctcattt accgcgcagt ctatcattgc tactacctct ttggcttata    1380
actatgagcc tgagcagttg aataagactg accctgagat gaattattat cttttggcga    1440
cctttataga ctcagccgct ataacgccaa cgaatatgac acagcctgat gtttgggatg    1500
ccttgctgac gatgtcccca ctatcagctg gcgaggtgac agtgaagggt gcggtagtga    1560
gtgaagtagt ccctgcagac ttgataggta gctacactcc agaatcccta aacgcctcac    1620
ttccgaatga tgctgctaga tgcatgatcg atagagcttc gaagatagcc gaagcaatca    1680
agattgatga tgatgctgga ccagatgaat attccccaaa ctctgtacca attcaaggtc    1740
agcttgctat ctcgcaactc gaaactggat atggtgtgcg aatattcaac cctaaaggga    1800
tccttttctaa aattgcatct agggcaatgc aggctttcat tggtgacccg agcacaatca    1860
tcacgcaggc ggcgccagtg ttatcagaca agaataattg gattgcattg gcacagggag    1920
tgaaaactag tctgcgtact aaaagtctat cagcgggagt gaagactgca gtgagtaagc    1980
tgagctcatc tgagtctatc cagaattgga ctcaaggatt cttggataaa gtgtcagcgc    2040
attttccagc accaaagccc gattgtccga ctagcggaga tagtggtgaa tcgtctaatc    2100
gccgagtgaa gcgcgactca tacgcaggag tggtcaaacg tgggtacaca cgttaggccg    2160
ctcgccctgg tgacgcgggg ttaagggatg caggcaaatc atc                      2203
```

```
<210> SEQ ID NO 27
<211> LENGTH: 708
<212> TYPE: PRT
<213> ORGANISM: Reovirus

<400> SEQUENCE: 27

Met Gly Asn Ala Ser Ser Ile Val Gln Thr Ile Asn Val Thr Gly Asp
1               5                   10                  15

Gly Asn Val Phe Lys Pro Ser Ala Glu Thr Ser Ser Thr Ala Val Pro
            20                  25                  30

Ser Leu Ser Leu Ser Pro Gly Met Leu Asn Pro Gly Gly Val Pro Trp
        35                  40                  45

Ile Ala Val Gly Asp Glu Thr Ser Val Thr Ser Pro Gly Ala Leu Arg
    50                  55                  60

Arg Met Thr Ser Lys Asp Ile Pro Glu Thr Ala Ile Ile Asn Thr Asp
65                  70                  75                  80

Asn Ser Ser Gly Ala Val Pro Ser Glu Ser Ala Leu Val Pro Tyr Ile
                85                  90                  95

Asp Glu Pro Leu Val Val Val Thr Glu His Ala Ile Thr Asn Phe Thr
            100                 105                 110

Lys Ala Glu Met Ala Leu Glu Phe Asn Arg Glu Phe Leu Asp Lys Met
        115                 120                 125

Arg Val Leu Ser Val Ser Pro Lys Tyr Ser Asp Leu Leu Thr Tyr Val
130                 135                 140

Asp Cys Tyr Val Gly Val Ser Ala Arg Gln Ala Leu Asn Asn Phe Gln
145                 150                 155                 160

Lys Gln Val Pro Val Ile Thr Pro Thr Arg Gln Thr Met Tyr Val Asp
                165                 170                 175

Ser Ile Gln Ala Ala Leu Lys Ala Leu Glu Lys Trp Glu Ile Asp Leu
            180                 185                 190

Arg Val Ala Gln Thr Leu Leu Pro Thr Asn Val Pro Ile Gly Glu Val
        195                 200                 205

Ser Cys Pro Met Gln Ser Val Val Lys Leu Leu Asp Asp Gln Leu Pro
    210                 215                 220

Asp Asp Thr Leu Ile Arg Arg Tyr Pro Lys Glu Ala Ala Val Ala Leu
225                 230                 235                 240

Ala Lys Arg Asn Gly Gly Ile Gln Trp Met Asp Val Ser Glu Gly Thr
                245                 250                 255

Val Met Asn Glu Ala Val Asn Ala Ala Ser Ala Leu Ala Pro
            260                 265                 270

Ser Ala Ser Ala Pro Pro Leu Glu Glu Lys Ser Lys Leu Thr Glu Gln
        275                 280                 285

Ala Met Asp Leu Val Thr Ala Ala Glu Pro Glu Ile Ile Ala Ser Leu
    290                 295                 300

Ala Pro Val Pro Ala Pro Val Phe Ala Ile Pro Pro Lys Pro Ala Asp
305                 310                 315                 320

Tyr Asn Val Arg Thr Leu Arg Ile Asp Glu Ala Thr Trp Leu Arg Met
                325                 330                 335

Ile Pro Lys Ser Met Asn Thr Pro Phe Gln Ile Gln Val Thr Asp Asn
            340                 345                 350

Thr Gly Thr Asn Trp His Leu Asn Leu Arg Gly Gly Thr Arg Val Val
        355                 360                 365

Asn Leu Asp Gln Ile Ala Pro Met Arg Phe Val Leu Asp Leu Gly Gly
    370                 375                 380
```

```
Lys Ser Tyr Lys Glu Thr Ser Trp Asp Pro Asn Gly Lys Lys Val Gly
385                 390                 395                 400

Phe Ile Val Phe Gln Ser Lys Ile Pro Phe Glu Leu Trp Thr Ala Ala
            405                 410                 415

Ser Gln Ile Gly Gln Ala Thr Val Val Asn Tyr Val Gln Leu Tyr Ala
        420                 425                 430

Glu Asp Ser Ser Phe Thr Ala Gln Ser Ile Ile Ala Thr Thr Ser Leu
    435                 440                 445

Ala Tyr Asn Tyr Glu Pro Gln Leu Asn Lys Thr Asp Pro Glu Met
450                 455                 460

Asn Tyr Tyr Leu Leu Ala Thr Phe Ile Asp Ser Ala Ala Ile Thr Pro
465                 470                 475                 480

Thr Asn Met Thr Gln Pro Asp Val Trp Asp Ala Leu Leu Thr Met Ser
            485                 490                 495

Pro Leu Ser Ala Gly Glu Val Thr Val Lys Gly Ala Val Val Ser Glu
        500                 505                 510

Val Val Pro Ala Asp Leu Ile Gly Ser Tyr Thr Pro Glu Ser Leu Asn
    515                 520                 525

Ala Ser Leu Pro Asn Asp Ala Ala Arg Cys Met Ile Asp Arg Ala Ser
530                 535                 540

Lys Ile Ala Glu Ala Ile Lys Ile Asp Asp Ala Gly Pro Asp Glu
545                 550                 555                 560

Tyr Ser Pro Asn Ser Val Pro Ile Gln Gly Gln Leu Ala Ile Ser Gln
            565                 570                 575

Leu Glu Thr Gly Tyr Gly Val Arg Ile Phe Asn Pro Lys Gly Ile Leu
        580                 585                 590

Ser Lys Ile Ala Ser Arg Ala Met Gln Ala Phe Ile Gly Asp Pro Ser
    595                 600                 605

Thr Ile Ile Thr Gln Ala Ala Pro Val Leu Ser Asp Lys Asn Asn Trp
610                 615                 620

Ile Ala Leu Ala Gln Gly Val Lys Thr Ser Leu Arg Thr Lys Ser Leu
625                 630                 635                 640

Ser Ala Gly Val Lys Thr Ala Val Ser Lys Leu Ser Ser Ser Glu Ser
            645                 650                 655

Ile Gln Asn Trp Thr Gln Gly Phe Leu Asp Lys Val Ser Ala His Phe
        660                 665                 670

Pro Ala Pro Lys Pro Asp Cys Pro Thr Ser Gly Asp Ser Gly Glu Ser
    675                 680                 685

Ser Asn Arg Arg Val Lys Arg Asp Ser Tyr Ala Gly Val Val Lys Arg
690                 695                 700

Gly Tyr Thr Arg
705

<210> SEQ ID NO 28
<211> LENGTH: 2304
<212> TYPE: DNA
<213> ORGANISM: Reovirus

<400> SEQUENCE: 28
gctattcgcg gtcatggctt acatcgcagt tcctgcggtg gtggattcac gttcgagtga      60
ggctattgga ctgctagaat cgtttggagt agacgctggg gctgacgcga atgacgtttc     120
atatcaagat catgactatg tgttggatca gttacagtac atgttagatg gatatgaggc     180
tggtgacgtt atcgatgcac tcgtccacaa gaattggtta catcactctg tctattgctt     240
```

```
gttgccaccc aaaagtcaac tattagagta ttggaaaagt aatccttcag cgataccgga    300
caacgttgat cgtcggcttc gtaaacgact aatgctaaag aaagatctca ggaaagatga    360
tgaatacaat cagctagcgc gtgctttcaa gatatcggat gtctacgcac ctctcatctc    420
atccacgacg tcaccgatga caatgataca gaacttgaat cgaggcgaga tcgtgtacac    480
cacgacggac agggtaatag gggctagaat cttgttatat gctcctagaa agtactatgc    540
gtcaactctg tcatttacta tgactaagtg catcattccg tttggtaaag aggtgggtcg    600
tgttcctcac tctcgattta atgttggcac atttccgtca attgctaccc cgaaatgttt    660
tgtcatgagt ggggttgata ttgagtccat cccaaatgaa tttatcaagt tgttttacca    720
gcgcgtcaag agtgttcacg ctaacatact aaatgacata tctcctcaga tcgtctctga    780
catgataaac agaaagcgtc tgcgcgttca tactccatca gatcgtcgag ccgcgcagtt    840
gatgcatttg ccttaccatg ttaaacgagg agcgtctcac gtcgacgttt acaaggtgga    900
tgttgtagac atgttgttcg aggtagtgga tgtggccgat gggttgcgca acgtatctag    960
gaaactaact atgcataccg ttcctgtatg tattcttgaa atgttgggta ttgagattgc   1020
ggactattgc attcgtcaag aggatggaat gctcacagat tggttcctac ttttaaccat   1080
gctatctgat ggcttgactg atagaaggac gcattgtcaa tacttgatga atccgtcaag   1140
tgtgcctcct gatgtgatac ttaacatctc aattactgga tttataaata gacatacaat   1200
cgatgtcatg cctgacatat atgacttcgt taaacccatt ggcgctgtgc tgcctaaggg   1260
atcatttaaa tcaacaatta tgagagttct tgattcaata tcaatattag gaatccaaat   1320
catgccgcgc gcgcatgtag ttgactcaga tgaggtgggc gagcaaatgg agcctacgtt   1380
tgagcaggcg gttatggaga tatacaaagg gattgctggc gttgactcgc tggatgatct   1440
catcaagtgg gtgttgaact cggatctcat tccgcatgat gacaggcttg gtcaattatt   1500
tcaagcgttt ttgcctctcg caaaggactt attagctcca atggccagaa agttttatga   1560
taactcaatg agtgagggta gattgctaac attcgctcat gccgacagtg agttgctgaa   1620
cgcaaattat tttggtcatt tattgcgact aaaaatacca tatattacag aggttaatct   1680
gatgattcgc aagaatcgtg agggtggaga gctatttcag cttgtgttat cttatctata   1740
taaaatgtat gctactagcg cgcagcctaa atggtttgga tcattattgc gattgttaat   1800
atgtccctgg ttacatatgg agaaattaat aggagaagca gacccggcat ctacgtcggc   1860
tgaaattggg tggcatatcc ctcgtgaaca gctgatgcaa gatggatggt gtggatgtga   1920
agacggattc attccctatg ttagcatacg tgcgccaaga ctggttatag aggagttgat   1980
ggagaagaac tggggccaat atcatgccca agttattgtc actgatcagc ttgtcgtagg   2040
cgaaccgcgg agggtatctg ctaaggctgt gatcaagggt aaccacttac cagttaagtt   2100
agtttcacga tttgcatgtt tcacattgac ggcgaagtat gagatgaggc tttcgtgcgg   2160
ccatagcact ggacgtggag ctgcatacag tgcgagacta gctttccgat ctgacttggc   2220
gtgatccgtg acatgcgtag tgtgacacct gctcctaggt caatgggggt aggggcggg   2280 ctaagactac gtacgcgctt catc                                         2304
```

<210> SEQ ID NO 29
<211> LENGTH: 736
<212> TYPE: PRT
<213> ORGANISM: Reovirus

<400> SEQUENCE: 29

```
Met Ala Tyr Ile Ala Val Pro Ala Val Asp Ser Arg Ser Ser Glu
1               5                   10                  15

Ala Ile Gly Leu Leu Glu Ser Phe Gly Val Asp Ala Gly Ala Asp Ala
            20                  25                  30

Asn Asp Val Ser Tyr Gln Asp His Asp Tyr Val Leu Asp Gln Leu Gln
            35                  40                  45

Tyr Met Leu Asp Gly Tyr Glu Ala Gly Asp Val Ile Asp Ala Leu Val
        50                  55                  60

His Lys Asn Trp Leu His His Ser Val Tyr Cys Leu Leu Pro Pro Lys
65                  70                  75                  80

Ser Gln Leu Leu Glu Tyr Trp Lys Ser Asn Pro Ser Ala Ile Pro Asp
                85                  90                  95

Asn Val Asp Arg Arg Leu Arg Lys Arg Leu Met Leu Lys Lys Asp Leu
            100                 105                 110

Arg Lys Asp Asp Glu Tyr Asn Gln Leu Ala Arg Ala Phe Lys Ile Ser
            115                 120                 125

Asp Val Tyr Ala Pro Leu Ile Ser Ser Thr Thr Ser Pro Met Thr Met
130                 135                 140

Ile Gln Asn Leu Asn Arg Gly Glu Ile Val Tyr Thr Thr Thr Asp Arg
145                 150                 155                 160

Val Ile Gly Ala Arg Ile Leu Leu Tyr Ala Pro Arg Lys Tyr Tyr Ala
                165                 170                 175

Ser Thr Leu Ser Phe Thr Met Thr Lys Cys Ile Ile Pro Phe Gly Lys
            180                 185                 190

Glu Val Gly Arg Val Pro His Ser Arg Phe Asn Val Gly Thr Phe Pro
            195                 200                 205

Ser Ile Ala Thr Pro Lys Cys Phe Val Met Ser Gly Val Asp Ile Glu
210                 215                 220

Ser Ile Pro Asn Glu Phe Ile Lys Leu Phe Tyr Gln Arg Val Lys Ser
225                 230                 235                 240

Val His Ala Asn Ile Leu Asn Asp Ile Ser Pro Gln Ile Val Ser Asp
                245                 250                 255

Met Ile Asn Arg Lys Arg Leu Arg Val His Thr Pro Ser Asp Arg Arg
            260                 265                 270

Ala Ala Gln Leu Met His Leu Pro Tyr His Val Lys Arg Gly Ala Ser
            275                 280                 285

His Val Asp Val Tyr Lys Val Asp Val Asp Met Leu Phe Glu Val
290                 295                 300

Val Asp Val Ala Asp Gly Leu Arg Asn Val Ser Arg Lys Leu Thr Met
305                 310                 315                 320

His Thr Val Pro Val Cys Ile Leu Glu Met Leu Gly Ile Glu Ile Ala
                325                 330                 335

Asp Tyr Cys Ile Arg Gln Glu Asp Gly Met Leu Thr Asp Trp Phe Leu
            340                 345                 350

Leu Leu Thr Met Leu Ser Asp Gly Leu Thr Asp Arg Arg Thr His Cys
            355                 360                 365

Gln Tyr Leu Met Asn Pro Ser Ser Val Pro Pro Asp Val Ile Leu Asn
370                 375                 380

Ile Ser Ile Thr Gly Phe Ile Asn Arg His Thr Ile Asp Val Met Pro
385                 390                 395                 400

Asp Ile Tyr Asp Phe Val Lys Pro Ile Gly Ala Val Leu Pro Lys Gly
                405                 410                 415
```

```
Ser Phe Lys Ser Thr Ile Met Arg Val Leu Asp Ser Ile Ser Ile Leu
                420                 425                 430

Gly Ile Gln Ile Met Pro Arg Ala His Val Val Asp Ser Asp Glu Val
            435                 440                 445

Gly Glu Gln Met Glu Pro Thr Phe Glu Gln Ala Val Met Glu Ile Tyr
450                 455                 460

Lys Gly Ile Ala Gly Val Asp Ser Leu Asp Asp Leu Ile Lys Trp Val
465                 470                 475                 480

Leu Asn Ser Asp Leu Ile Pro His Asp Asp Arg Leu Gly Gln Leu Phe
                485                 490                 495

Gln Ala Phe Leu Pro Leu Ala Lys Asp Leu Leu Ala Pro Met Ala Arg
            500                 505                 510

Lys Phe Tyr Asp Asn Ser Met Ser Glu Gly Arg Leu Leu Thr Phe Ala
            515                 520                 525

His Ala Asp Ser Glu Leu Leu Asn Ala Asn Tyr Phe Gly His Leu Leu
530                 535                 540

Arg Leu Lys Ile Pro Tyr Ile Thr Glu Val Asn Leu Met Ile Arg Lys
545                 550                 555                 560

Asn Arg Glu Gly Gly Glu Leu Phe Gln Leu Val Leu Ser Tyr Leu Tyr
                565                 570                 575

Lys Met Tyr Ala Thr Ser Ala Gln Pro Lys Trp Phe Gly Ser Leu Leu
            580                 585                 590

Arg Leu Leu Ile Cys Pro Trp Leu His Met Glu Lys Leu Ile Gly Glu
            595                 600                 605

Ala Asp Pro Ala Ser Thr Ser Ala Glu Ile Gly Trp His Ile Pro Arg
610                 615                 620

Glu Gln Leu Met Gln Asp Gly Trp Cys Gly Cys Glu Asp Gly Phe Ile
625                 630                 635                 640

Pro Tyr Val Ser Ile Arg Ala Pro Arg Leu Val Ile Glu Glu Leu Met
                645                 650                 655

Glu Lys Asn Trp Gly Gln Tyr His Ala Gln Val Ile Val Thr Asp Gln
            660                 665                 670

Leu Val Val Gly Glu Pro Arg Arg Val Ser Ala Lys Ala Val Ile Lys
            675                 680                 685

Gly Asn His Leu Pro Val Lys Leu Val Ser Arg Phe Ala Cys Phe Thr
690                 695                 700

Leu Thr Ala Lys Tyr Glu Met Arg Leu Ser Cys Gly His Ser Thr Gly
705                 710                 715                 720

Arg Gly Ala Ala Tyr Ser Ala Arg Leu Ala Phe Arg Ser Asp Leu Ala
                725                 730                 735

<210> SEQ ID NO 30
<211> LENGTH: 418
<212> TYPE: PRT
<213> ORGANISM: Reovirus

<400> SEQUENCE: 30

Met Ala Arg Ala Ala Phe Leu Phe Lys Thr Val Gly Phe Gly Gly Leu
1               5                   10                  15

Gln Asn Val Pro Ile Asn Asp Glu Leu Ser Ser His Leu Leu Arg Ala
            20                  25                  30

Gly Asn Ser Pro Trp Gln Leu Thr Gln Phe Leu Asp Trp Ile Ser Leu
        35                  40                  45

Gly Arg Gly Leu Ala Thr Ser Ala Leu Val Pro Thr Ala Gly Ser Arg
    50                  55                  60
```

```
Tyr Tyr Gln Met Ser Cys Leu Leu Ser Gly Thr Leu Gln Ile Pro Phe
 65              70                  75                  80

Arg Pro Asn His Arg Trp Gly Asp Ile Arg Phe Leu Arg Leu Val Trp
                 85                  90                  95

Ser Ala Pro Thr Leu Asp Gly Leu Val Val Ala Pro Pro Gln Val Leu
                100             105             110

Ala Gln Pro Ala Leu Gln Ala Gln Ala Asp Arg Val Tyr Asp Cys Asp
            115             120             125

Asp Tyr Pro Phe Leu Ala Arg Asp Pro Arg Phe Lys His Arg Val Tyr
        130             135             140

Gln Gln Leu Ser Ala Val Thr Leu Leu Asn Leu Thr Gly Phe Gly Pro
145             150             155             160

Ile Ser Tyr Val Arg Val Asp Glu Asp Met Trp Ser Gly Asp Val Asn
                165             170             175

Gln Leu Leu Met Asn Tyr Phe Gly His Thr Phe Ala Glu Ile Ala Tyr
            180             185             190

Thr Leu Cys Gln Ala Ser Ala Asn Arg Pro Trp Glu Tyr Asp Gly Thr
        195             200             205

Tyr Ala Arg Met Thr Gln Ile Val Leu Ser Leu Phe Trp Leu Ser Tyr
210             215             220

Val Gly Val Ile His Gln Gln Asn Thr Tyr Arg Thr Phe Tyr Phe Gln
225             230             235             240

Cys Asn Arg Arg Gly Asp Ala Ala Glu Val Trp Ile Leu Ser Cys Ser
                245             250             255

Leu Asn His Ser Ala Gln Ile Arg Pro Gly Asn Arg Ser Leu Phe Val
            260             265             270

Met Pro Thr Ser Pro Asp Trp Asn Met Asp Val Asn Leu Ile Leu Ser
        275             280             285

Ser Thr Leu Thr Gly Cys Leu Cys Ser Gly Ser Gln Leu Pro Leu Ile
290             295             300

Asp Asn Asn Ser Val Pro Ala Val Ser Arg Asn Ile His Gly Trp Thr
305             310             315             320

Gly Arg Ala Gly Asn Gln Leu His Gly Phe Gln Val Arg Arg Met Val
                325             330             335

Thr Glu Phe Cys Asp Arg Leu Arg Arg Asp Gly Val Met Thr Gln Ala
            340             345             350

Gln Gln Asn Gln Val Glu Ala Leu Ala Asp Gln Thr Gln Gln Phe Lys
            355             360             365

Arg Asp Lys Leu Glu Thr Trp Ala Arg Glu Asp Gln Tyr Asn Gln
        370             375             380

Ala His Pro Asn Ser Thr Met Phe Arg Thr Lys Pro Phe Thr Asn Ala
385             390             395             400

Gln Trp Gly Arg Gly Asn Thr Gly Ala Thr Ser Ala Ala Ile Ala Ala
                405             410             415

Leu Ile
```